United States Patent
Getman et al.

(10) Patent No.: US 12,291,753 B2
(45) Date of Patent: May 6, 2025

(54) COMPOSITIONS AND METHODS FOR DETECTING BACTERIAL NUCLEIC ACID AND DIAGNOSING BACTERIAL VAGINOSIS

(71) Applicant: Gen-Probe Incorporated, San Diego, CA (US)

(72) Inventors: Damon Kittredge Getman, Poway, CA (US); Angela Sebring Hudson, San Diego, CA (US); Jimmykim Pham, San Diego, CA (US); Xianqun Wang, San Diego, CA (US); Caroline Clark, Oceanside, CA (US)

(73) Assignee: Gen-Probe Incorporated, San Diego, CA (US)

( * ) Notice: Subject to any disclaimer, the term of this patent is extended or adjusted under 35 U.S.C. 154(b) by 1050 days.

(21) Appl. No.: 17/182,861

(22) Filed: Feb. 23, 2021

(65) Prior Publication Data

US 2021/0198720 A1 Jul. 1, 2021

Related U.S. Application Data

(63) Continuation of application No. PCT/US2019/047854, filed on Aug. 23, 2019.

(60) Provisional application No. 62/722,627, filed on Aug. 24, 2018.

(51) Int. Cl.
*C12Q 1/689* (2018.01)

(52) U.S. Cl.
CPC ......... *C12Q 1/689* (2013.01); *C12Q 2600/16* (2013.01)

(58) Field of Classification Search
None
See application file for complete search history.

(56) References Cited

U.S. PATENT DOCUMENTS

2013/0316922 A1  11/2013  Balashov et al.
2018/0291431 A1*  10/2018  Paquette ................. C12Q 1/68

FOREIGN PATENT DOCUMENTS

| CN | 103045725 A | * | 4/2013 | |
|---|---|---|---|---|
| KR | 2017-0138481 | | 12/2017 | |
| WO | 2011103274 A1 | | 8/2011 | |
| WO | WO-2016149357 A1 | * | 9/2016 | ........... C12Q 1/6865 |
| WO | 2016172204 A1 | | 10/2016 | |

OTHER PUBLICATIONS

Shipitsyna, Elena, et al. "Composition of the vaginal microbiota in women of reproductive age-sensitive and specific molecular diagnosis of bacterial vaginosis is possible ?. " PloS one 8.4 (2013): e60670. (Year: 2013).*
Rumyantseva T, Shipitsyna E, Guschin A, Unemo M. Evaluation and subsequent optimizations of the quantitative AmpliSens Florocenosis/Bacterial vaginosis-FRT multiplex real-time PCR assay for diagnosis of bacterial vaginosis. APMIS. Dec. 2016;124(12): 1099-1108. doi: 10.1111/apm.12608. Epub Oct. 7, 2016. (Year: 2016).*
Yan et al., Combining multiple biomarkers linearly to maximize the partial area under the ROC curve. Stat Med. Feb. 20, 2018;37(4): 627-642. doi: 10.1002/sim.7535. Epub Oct. 30, 2017. PMID: 29082535; PMCID: PMC6469690. (Year: 2017).*
Rumyantseva et al., Evaluation and subsequent optimizations of the quantitative AmpliSens Florocenosis/Bacterial vaginosis-FRT multiplex real-time PCR assay for diagnosis of bacterial vaginosis. APMIS. Dec. 2016;124(12):1099-1108. doi: 10.1111/apm.12608. Epub Oct. 7, 2016. PMID: 27714844. (Year: 2016).*
Huggett et al. Differential susceptibility of PCR reactions to inhibitors: an important and unrecognised phenomenon. BMC Res Notes 1, 70 (2008). doi.org/10.1186/1756-0500-1-70 (Year: 2008).*
Amsel et al., "Nonspecific vaginitis: Diagnostic criteria and microbial and epidemiologic associations," Am. J. Med. 74 (1): 14-22 (1983).
Cartwright et al., "Comparison of Nucleic Acid Amplification Assays with BD Affirm VPIII for Diagnosis of Vaginitis in Symptomatic Women," J. Clin. Microbiol. 51(11): 3694-3699 (2013).
De Backer et al., "Quantitative determination by real-time PCR of four vaginal *Lactobacillus* species, Gerdnerella vaginalis and Atopobium vaginae indicates an inverse relationship between *L. gasseri* and *L. iners*," BMC Microbiology 7: 115 (2007) (13 pages).
Kusters et al., "A multiplex real-time PCR assay for routine diagnosis of bacterial vaginosis," European Journal of Clinical Microbiology & Infectious Diseases 34: 1779-1785 (2015).
Nugent et al., "Reliability of Diagnosing Bacterial Vaginosis Is Improved by a Standardized Method of Gram Stain Interpretation," Journal of Clinical Microbiology 29(2): 297-301 (1991).
PCT, International Search Report and Written Opinion for PCT/US2019/047854, dated Nov. 4, 2019 (17 pages).
Notice of Preliminary Rejection mailed Nov. 27, 2024, issued in corresponding Korean Application No. 10-2021-7008802, filed Aug. 23, 2019, 2 pages.

* cited by examiner

*Primary Examiner* — Aaron A Priest
*Assistant Examiner* — Tian Nmn Yu
(74) *Attorney, Agent, or Firm* — CHRISTENSEN O'CONNOR JOHNSON KINDNESS PLLC; Jeffrey E. Landes

(57) ABSTRACT

Disclosed are methods for diagnosing Bacterial Vaginosis in a subject comprising performing an assay for the detection of any one or more of *Lactobacillus* sp., Atopobium vaginae, and *Gardneralla vaginalis* in a subject sample. Also disclosed are compositions and methods for detecting *Lactobacillus* sp., Atopobium vaginae, and/or *Gardneralla vaginalis* nucleic acid in a sample.

11 Claims, No Drawings
Specification includes a Sequence Listing.

SEQUENCE LISTING

```
<160> NUMBER OF SEQ ID NOS: 261

<210> SEQ ID NO 1
<211> LENGTH: 1518
<212> TYPE: DNA
<213> ORGANISM: Lactobacillus crispatus
<300> PUBLICATION INFORMATION:
<308> DATABASE ACCESSION NUMBER: NR_041800
<309> DATABASE ENTRY DATE: 2015-02-03
<313> RELEVANT RESIDUES IN SEQ ID NO: (1)..(1518)

<400> SEQUENCE: 1
gacgaacgct ggcggcgtgc ctaatacatg caagtcgagc gagcggaact aacagattta     60
cttcggtaat gacgttagga aagcgagcgg cggatgggtg agtaacacgt ggggaacctg    120
ccccatagtc tgggatacca cttggaaaca ggtgctaata ccggataaga aagcagatcg    180
catgatcagc ttttaaaagg cggcgtaagc tgtcgctatg ggatggcccc gcggtgcatt    240
agctagttgg taaggtaaag gcttaccaag gcgatgatgc atagccgagt tgagagactg    300
atcggccaca ttgggactga gacacggccc aaactcctac gggaggcagc agtagggaat    360
```

```
cttccacaat ggacgcaagt ctgatggagc aacgccgcgt gagtgaagaa ggttttcgga    420
tcgtaaagct ctgttgttgg tgaagaagga tagaggtagt aactggcctt tatttgacgg    480
taatcaacca gaaagtcacg gctaactacg tgccagcagc cgcggtaata cgtaggtggc    540
aagcgttgtc cggatttatt gggcgtaaag cgagcgcagg cggaagaata agtctgatgt    600
gaaagccctc ggcttaaccg aggaactgca tcggaaactg ttttcttga gtgcagaaga    660 ggagagtgga actccatgtg tagcggtgga atgcgtagat atatggaaga acaccagtgg    720
cgaaggcggc tctctggtct gcaactgacg ctgaggctcg aaagcatggg tagcgaacag    780
gattagatac cctggtagtc catgccgtaa acgatgagtg ctaagtgttg ggaggtttcc    840
gcctctcagt gctgcagcta acgcattaag cactccgcct ggggagtacg accgcaaggt    900
tgaaactcaa aggaattgac gggggcccgc acaagcggtg gagcatgtgg tttaattcga    960
agcaacgcga agaaccttac caggtcttga catctagtgc catttgtaga gatacaaagt   1020
tcccttcggg gacgctaaga caggtggtgc atggctgtcg tcagctcgtg tcgtgagatg   1080
ttgggttaag tcccgcaacg agcgcaaccc ttgttattag ttgccagcat taagttgggc   1140
actctaatga gactgccggt gacaaaccgg aggaaggtgg ggatgacgtc aagtcatcat   1200
gccccttatg acctgggcta cacacgtgct acaatgggca gtacaacgag aagcgagcct   1260
gcgaaggcaa gcgaatctct gaaagctgtt ctcagttcgg actgcagtct gcaactcgac   1320
tgcacgaagc tggaatcgct agtaatcgcg gatcagcacg ccgcggtgaa tacgttcccg   1380
ggccttgtac acaccgcccg tcacaccatg ggagtctgca atgcccaaag ccggtggcct   1440
aaccttcggg aaggagccgt ctaaggcagg gcagatgact ggggtgaagt cgtaacaagg   1500
tagccgtagg agaactgc                                                 1518
```

<210> SEQ ID NO 2
<211> LENGTH: 1496
<212> TYPE: DNA
<213> ORGANISM: Lactobacillus jensenii
<300> PUBLICATION INFORMATION:
<308> DATABASE ACCESSION NUMBER: NR_025087
<309> DATABASE ENTRY DATE: 2015-02-03
<313> RELEVANT RESIDUES IN SEQ ID NO: (1)..(1496)

<400> SEQUENCE: 2

```
tgcctaatac atgcaagtcg agcgagcttg cctatagaag ttcttcggaa tggaaataga     60
tacaagctag cggcggatgg gtgagtaacg cgtgggtaac ctgcccttaa gtctgggata    120
ccatttggaa acagatgcta ataccggata aagctacttt cgcatgaaa gaagtttaaa    180 aggcggcgta agctgtcgta aaggatggac ttgcgatgca ttagctagtt ggtaaggtaa    240
cggcttacca aggctgatga tgcatagccg agttgagaga ctgatcggcc acattgggac    300
tgagacacgg cccaaactcc tacgggaggc agcagtaggg aatcttccac aatggacgaa    360
agtctgatgg agcaacgccg cgtgagtgaa gaaggttttc ggatcgtaaa gctctgttgt    420
tggtgaagaa ggatagaggt agtaactggc ctttatttga cggtaatcaa ccagaaagtc    480
acggctaact acgtgccagc agccgcggta atacgtaggt ggcaagcgtt gtccggattt    540
attgggcgta aagcgagcgc aggcggattg ataagtctga tgtgaaagcc ttcggctcaa    600
ccgaagaact gcatcagaaa ctgtcaatct tgagtgcaga agaggagagt ggaactccat    660
gtgtagcggt ggaatgcgta gatatatgga agaacaccag tggcgaaggc ggctctctgg    720
tctgtaactg acgctgaggc tcgaaagcat gggtagcgaa caggattaga taccctggta    780
gtccatgccg taaacgatga gtgctaagtg ttgggaggtt ccgcctctc agtgctgcag    840
```

```
ctaacgcatt aagcactccg cctggggagt acgaccgcaa ggttgaaact caaaggaatt      900 gacggggggcc cgcacaagcg gtggagcatg tggtttaatt cgaagcaacg cgaagaacct     960
taccaggtct tgacatcctt tgaccaccta agagattagg ttttcccttc ggggacaaag     1020
agacaggtgg tgcatggctg tcgtcagctc gtgtcgtgag atgttgggtt aagtcccgca     1080
acgagcgcaa cccttgttaa tagttgccag cattaagttg ggcactctat tgagactgcc     1140
ggtgacaaac cggaggaagg tggggatgac gtcaagtcat catgcccctt atgacctggg     1200
ctacacacgt gctacaatgg gcagtacaac gagaagcgaa cctgtgaagg caagcggatc     1260
tcttaaagct gttctcagtt cggactgtag gctgcaactc gcctacacga agctggaatc     1320
gctagtaatc gcggatcagc acgccgcggt gaatacgttc ccgggccttg tacacaccgc     1380
ccgtcacacc atgagagttt gtaacaccca aagtcggtga gtaacctttt ggagccagcc     1440
gcctaaggtg ggacagatga ttagggtgaa gtcgtaacaa ggtagccgta ggagaa         1496
```

<210> SEQ ID NO 3
<211> LENGTH: 1572
<212> TYPE: DNA
<213> ORGANISM: Lactobacillus gasseri
<300> PUBLICATION INFORMATION:
<308> DATABASE ACCESSION NUMBER: NR_041920
<309> DATABASE ENTRY DATE: 2017-10-24
<313> RELEVANT RESIDUES IN SEQ ID NO: (1)..(1572)

<400> SEQUENCE: 3

```
aaaatgagag tttgatcctg gctcaggacg aacgctggcg gcgtgcctaa tacatgcaag      60
tcgagcgagc ttgcctagat gaatttggtg cttgcaccag atgaaactag atacaagcga     120
gcggcggacg ggtgagtaac acgtgggtaa cctgcccaag agactgggat aacacctgga     180
aacagatgct aataccggat aacaacacta gacgcatgtc tagagtttaa aagatggttc     240
tgctatcact cttggatgga cctgcggtgc attagctagt tggtaaggta acggcttacc     300
aaggcaatga tgcatagccg agttgagaga ctgatcggcc acattgggac tgagacacgg     360
cccaaactcc tacgggaggc agcagtaggg aatcttccac aatggacgca agtctgatgg     420
agcaacgccg cgtgagtgaa gaagggtttc ggctcgtaaa gctctgttgg tagtgaagaa     480
agatagaggt agtaactggc ctttatttga cggtaattac ttagaaagtc acggctaact     540
acgtgccagc agccgcggta atacgtaggt ggcaagcgtt gtccggattt attgggcgta     600
aagcgagtgc aggcggttca ataagtctga tgtgaaagcc ttcggctcaa ccggagaatt     660
gcatcagaaa ctgttgaact tgagtgcaga agaggagagt ggaactccat gtgtagcggt     720
ggaatgcgta gatatatgga agaacaccag tggcgaaggc ggctctctgg tctgcaactg     780
acgctgaggc tcgaaagcat gggtagcgaa caggattaga taccctggta gtccatgccg     840
taaacgatga gtgctaagtg ttgggaggtt tccgcctctc agtgctgcag ctaacgcatt     900
aagcactccg cctggggagt acgaccgcaa ggttgaaact caaaggaatt gacggggggcc     960 cgcacaagcg gtggagcatg tggtttaatt cgaagcaacg cgaagaacct taccaggtct    1020
tgacatccag tgcaaaccta agagattagg tgttcccttc gggacgctg agacaggtgg    1080 tgcatggctg tcgtcagctc gtgtcgtgag atgttgggtt aagtcccgca acgagcgcaa    1140
cccttgtcat tagttgccat cattaagttg ggcactctaa tgagactgcc ggtgacaaac    1200
cggaggaagg tggggatgac gtcaagtcat catgcccctt atgacctggg ctacacacgt    1260
gctacaatgg acggtacaac gagaagcgaa cctgcgaagg caagcggatc tctgaaagcc    1320
```

| | |
|---|---|
| gttctcagtt cggactgtag gctgcaactc gcctacacga agctggaatc gctagtaatc | 1380 |
| gcggatcagc acgccgcggt gaatacgttc ccgggccttg tacacaccgc ccgtcacacc | 1440 |
| atgagagtct gtaacaccca agccggtggg ataacctttt ataggagtca gccgtctaag | 1500 |
| gtaggacaga tgattagggt gaagtcgtaa caaggtagcc gtaggagaac ctgcggctgg | 1560 |
| atcacctcct tt | 1572 |

<210> SEQ ID NO 4
<211> LENGTH: 1437
<212> TYPE: DNA
<213> ORGANISM: Atopobium vaginae
<300> PUBLICATION INFORMATION:
<308> DATABASE ACCESSION NUMBER: AF325325
<309> DATABASE ENTRY DATE: 2003-06-09
<313> RELEVANT RESIDUES IN SEQ ID NO: (1)..(1437)

<400> SEQUENCE: 4

| | |
|---|---|
| gatgaacgct ggcggcgcgc ctaacacatg caagtcgaac ggttaaagca tcttcggatg | 60 |
| tgtataaagt ggcgaacggc tgagtaacac gtgggcaacc tgccctttgc actgggatag | 120 |
| cctcgggaaa ccgaggttaa taccggatac tccatatttg tcgcatggcg aatatgggaa | 180 |
| agctccggcg gcaaaggatg ggcccgcggc ctgttagcta gttggtgggg tagtggccta | 240 |
| ccaaggcaat gatgggtagc cgggttgaga gaccgaccgg ccagattggg actgagacac | 300 |
| ggcccagact cctacgggag gcagcagtgg ggaatcttgc acaatgggcg aaagcctgat | 360 |
| gcagcgacgc cgcgtgcggg atgaaggcct tcggttgta aaccgctttc agcagggacg | 420 |
| aggccgcaag gtgacggtac ctgcagaaga agccccggct aactacgtgc cagcagccgc | 480 |
| ggtaatacgt aggggggcaag cgttatccgg attcattggg cgtaaagcgc gcgtaggcgg | 540 |
| tctgttaggt caggagttaa atctgggggc tcaaccccta tccgctcctg ataccggcag | 600 |
| gcttgagtct ggtaggggaa gatggaattc caagtgtagc ggtgaaatgc gcagatattt | 660 |
| ggaagaacac cggtggcgaa ggcggtcttc tgggccatga ctgacgctga ggcgcgaaag | 720 |
| ctaggggagc gaacaggatt agataccctg gtagtcctag ctgtaaacga tggacactag | 780 |
| gtgtggggag attatacttt ccgtgccgca gctaacgcat taagtgtccc gcctggggag | 840 |
| tacggtcgca agactaaaac tcaaaggaat tgacgggggc ccgcacaagc agcggagcat | 900 |
| gtggcttaat tcgaagcaac gcgaagaacc ttaccagggc ttgacattta ggtgaagcag | 960 |
| tggaaacact gtggccgaaa ggagcctaaa caggtggtgc atggctgtcg tcagctcgtg | 1020 |
| tcgtgagatg ttgggttaag tcccgcaacg agcgcaaccc ttgtcgcatg ttgccagcgg | 1080 |
| ttcggccggg cacccatgcg agaccgccgg cgttaagccg gaggaaggtg gggacgacgt | 1140 |
| caagtcatca tgccccttat gtcctgggct gcacacgtgc tacaatggcc ggcacagagg | 1200 |
| gctgctactg cgcgagcaga agcgaatccc taaagccggt cccagttcgg attggaggct | 1260 |
| gcaactcgcc tccatgaagt cggagttgct agtaatcgcg gatcagcacg ccgcggtgaa | 1320 |
| tgcgttcccg ggccttgtac acaccgcccg tcacaccacc cgagtcgtct gcacccgaag | 1380 |
| tcgtcggcct aacccgcaag ggagggaggc gccgaaggtg tggagggtaa gggggggt | 1437 |

<210> SEQ ID NO 5
<211> LENGTH: 1475
<212> TYPE: DNA
<213> ORGANISM: Gardnerella vaginalis
<220> FEATURE:
<221> NAME/KEY: misc_feature
<222> LOCATION: (60)..(60)
<223> OTHER INFORMATION: n is a, c, g, or t

```
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (916)..(916)
<223> OTHER INFORMATION: n is a, c, g, or t
<220> FEATURE:
<221> NAME/KEY: misc_feature
<222> LOCATION: (951)..(951)
<223> OTHER INFORMATION: n is a, c, g, or t
<220> FEATURE:
<221> NAME/KEY: misc_feature
<222> LOCATION: (1012)..(1012)
<223> OTHER INFORMATION: n is a, c, g, or t
<220> FEATURE:
<221> NAME/KEY: misc_feature
<222> LOCATION: (1156)..(1156)
<223> OTHER INFORMATION: n is a, c, g, or t
<220> FEATURE:
<221> NAME/KEY: misc_feature
<222> LOCATION: (1171)..(1171)
<223> OTHER INFORMATION: n is a, c, g, or t
<220> FEATURE:
<221> NAME/KEY: misc_feature
<222> LOCATION: (1277)..(1277)
<223> OTHER INFORMATION: n is a, c, g, or t
<300> PUBLICATION INFORMATION:
<308> DATABASE ACCESSION NUMBER: NR_044694
<309> DATABASE ENTRY DATE: 2017-10-24
<313> RELEVANT RESIDUES IN SEQ ID NO: (1)..(1475)

<400> SEQUENCE: 5
tttcgtggag ggttcgattc tggctcagga tgaacgctgg cggcgtgctt aacacatgcn    60
agtcgaacgg gatctgacca gcttgctggt tggtgagagt ggcgaacggg tgagtaatgc   120
gtgaccaacc tgccccatgc tccagaatag ctcttggaaa cgggtggtaa tgctggatgc   180
tccaacttga cgcatgtctt gttgggaaag tgtttagtgg catgggatgg ggtcgcgtcc   240
tatcagcttg taggcgggt aatggcccac ctaggcttcg acgggtagcc ggcctgagag   300
ggcggacggc cacattggga ctgagatacg gcccagactn ctacgggagg cagcagtggg   360
gaatattgcg caatggggga aaccctgacg cagcgacgnc gcgtgcggga tgaaggcctt   420
cgggttgtaa accgcttttg attgggagca agccttttgg gtgagtgtac ctttcgaata   480
agcgccggct aactacgtgc cagcagccgc ggtaatacgt agggcgcaag cgttatccgg   540
aattattggg cgtaaagagc ttgtaggcgg ttcgtcgcgt ctggtgtgaa agcccatcgc   600
ttaacggtgg gnttgcgccg ggtacgggcg ggctagagtg cagtagggga gactggaatt   660
ctcggtgtaa cggtggaatg tgtagatatc gggaagaaca ccaatggcga aggcaggtct   720
ctgggctgtt actgacgctg agaagcgaaa gcgtgggag cgaacaggat tagataccct   780
ggtagtccac gccgtaaacg gtggacgctg gatgtgggc ccattccacg ggttctgtgt   840
cggagctaac gcgttaagcg tcccgcctgg ggagtacggc cgcaaggcta aaactcaaag   900
aaattgacgg gggccngcac aagcggcgga gcatgcggat taattcgatg naacgcgaag   960
aaccttacct gggcttgaca tgtgcctgac gactgcagag atgtggtttc cnttcggggc  1020
aggttcacag gtggtgcatg gtcgtcgtca gctcgtgtcg tgagatgttg ggttaagtcc  1080
```

-continued

```
cgcaacgagc gcaaccctcg ccctgtgttg ccagcgggtt atgccgggaa ctcacggggg      1140
accgccgggg ttaccncgga ggaaggtggg natgacgtca gatcatcatg ccccttacgt      1200
ccagggcttc acgcatgcta caatggccag tacaacgggt tgcttcatgg tgacatggtg      1260
ctaatccctt aaaactngtc tcagttcgga tcgtagtctg caactcgact acgtgaaggc      1320
ggagtcgcta gtaatcgcga atcagcaacg tcgcggtgaa tgcgttcccg ggccttgtac      1380
acaccgcccg tcaagtcatg aaagtgggca gcacccgaag ccggtggcct aaccctttg      1440 ggatggagcc gtctaaggtg aggctcgtga ttggg                                1475
```

```
<210> SEQ ID NO 6
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (29)..(52)
<223> OTHER INFORMATION: dT3dA30 immobilized probe binding region

<400> SEQUENCE: 6
gucucucaac ucggcuaugu uuaaaaaaaa aaaaaaaaa aaaaaaaaaa aa              52
```

```
<210> SEQ ID NO 7
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 7
cgagcggaac taacag                                                     16
```

```
<210> SEQ ID NO 8
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 8
cttcggaatg gacataga                                                   18
```

```
<210> SEQ ID NO 9
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 9
tgcaccagat gaaactag                                                   18
```

```
<210> SEQ ID NO 10
<211> LENGTH: 45
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 10
```

-continued

```
aatttaatac gactcactat agggagataa gccgttacct tacca      45

<210> SEQ ID NO 11
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 11
gucugggaua ccacuugcag ac                                22

<210> SEQ ID NO 12
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 12
cagguggacu gggauaacac cug                               23

<210> SEQ ID NO 13
<211> LENGTH: 53
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (30)..(53)
<223> OTHER INFORMATION: dT3dA30 immobilized probe-binding region

<400> SEQUENCE: 13
ucucucaagc cggcuacccg tttaaaaaaa aaaaaaaaaa aaaaaaaaaa aaa    53

<210> SEQ ID NO 14
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 14
gctggatgct ccaacttg                                     18

<210> SEQ ID NO 15
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (9)..(35)

<400> SEQUENCE: 15
tgtttagtaa tttaatacga ctcactatag ggagatccca tgccactaaa ca    52

<210> SEQ ID NO 16
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 16
```

```
cgcaugucuu guugggaaug cg                                              22
```

<210> SEQ ID NO 17
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 17

```
gtctgttagg tcaggagtt                                                  19
```

<210> SEQ ID NO 18
<211> LENGTH: 45
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 18

```
aatttaatac gactcactat agggagacca tcttccccta ccaga                     45
```

<210> SEQ ID NO 19
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 19

```
cugcccuccu gauaccggca g                                               21
```

<210> SEQ ID NO 20
<211> LENGTH: 57
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (35)..(57)
<223> OTHER INFORMATION: dT3dA30 immobilized probe-binding region

<400> SEQUENCE: 20

```
cguucacuau uggucucugc auuctttaaa aaaaaaaaa aaaaaaaaa aaaaaaa          57
```

<210> SEQ ID NO 21
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 21

```
gattatatag gacgacaag                                                  19
```

<210> SEQ ID NO 22
<211> LENGTH: 49
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

```
<400> SEQUENCE: 22
aatttaatac gactcactat agggagagat gattgacttg tgattccgc        49

<210> SEQ ID NO 23
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 23
gcauggugcg aauugggaca ugc                                    23

<210> SEQ ID NO 24
<211> LENGTH: 51
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 24
aatttaatac gactcactat agggagatat caggagcgga tagggguttga g    51

<210> SEQ ID NO 25
<211> LENGTH: 57
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (35)..(57)
<223> OTHER INFORMATION: dT3dA30 immobilized probe-binding region

<400> SEQUENCE: 25
ggacuaccag gguaucuaau ccugtttaaa aaaaaaaaa aaaaaaaaa aaaaaaa  57

<210> SEQ ID NO 26
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 26 gtaggggggca agcgttatcc ggattc                                26

<210> SEQ ID NO 27
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 27
aggucaggag uuaaaucugg guccu                                  25

<210> SEQ ID NO 28
<211> LENGTH: 26
<212> TYPE: DNA
<213> ORGANISM: Artificial Sequence
<220> FEATURE:
<223> OTHER INFORMATION: Synthetic Oligonucleotide
```

```
<220> FEATURE:
<221> NAME/KEY: misc_feature
<222> LOCATION: (6)..(6)
<223> OTHER INFORMATION: n is a or g or c or t/u, unknown, or other
      (any)

<400> SEQUENCE: 28
gtaggnggca agcgttatcc ggattc                                          26

<210> SEQ ID NO 29
<211> LENGTH: 56
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (34)..(56)
<223> OTHER INFORMATION: dT3dA30 immobilized probe-binding region

<400> SEQUENCE: 29
ggcagguugg ucacgcauua cuctttaaaa aaaaaaaaaa aaaaaaaaaa aaaaaa         56

<210> SEQ ID NO 30
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 30
aggucaggag uuaaaucugg gaccu                                           25

<210> SEQ ID NO 31
<211> LENGTH: 45
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 31
aatttaatac gactcactat agggagataa gccgttacct tacca                     45

<210> SEQ ID NO 32
<211> LENGTH: 45
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 32
aatttaatac gactcactat agggagacac cacctgtgaa cctgc                     45

<210> SEQ ID NO 33
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 33
cttacctggg cttgacatgt gcctg                                           25
```

<210> SEQ ID NO 34
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 34
ccugcagaga ugugguuucg cagg                                        24

<210> SEQ ID NO 35
<211> LENGTH: 45
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 35
aatttaatac gactcactat agggagatcc catgccacta aacac                 45

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
gtaatgctgg atgctccaac                                             20

<210> SEQ ID NO 37
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 37
gacgcauguc uuguugggcg uc                                          22

<210> SEQ ID NO 38
<211> LENGTH: 55
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (33)..(55)
<223> OTHER INFORMATION: dT3dA30 immobilized probe-binding region

<400> SEQUENCE: 38
caagagcuau ucuggagcau ggtttaaaaa aaaaaaaaaa aaaaaaaaaa aaaaa       55

<210> SEQ ID NO 39
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 39
gaaacgggtg gtaatgctg                                              19

```
<210> SEQ ID NO 40
<211> LENGTH: 47
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(28)

<400> SEQUENCE: 40
aaatttaata cgactcacta tagggagacc atcccatgcc actaaac        47

<210> SEQ ID NO 41
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 41
ccaacuugac gcaugucuug uugg        24

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 42
ctggatgctc caacttgacg        20

<210> SEQ ID NO 43
<211> LENGTH: 47
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 43
aatttaatac gactcactat agggagatcg aagcctaggt gggccat        47

<210> SEQ ID NO 44
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 44
cgggaaagug uuuaguggca ucccg        25

<210> SEQ ID NO 45
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 45
tccggattca ttgggcgtaa        20
```

```
<210> SEQ ID NO 46
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 46
tatccggatt cattgggcgt aaag                                          24

<210> SEQ ID NO 47
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 47
cggattcatt gggcgtaaag cg                                            22

<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
ggucuguuag gucagagacc                                               20

<210> SEQ ID NO 49
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 49
ccuguuaggu caggaguaca gg                                            22

<210> SEQ ID NO 50
<211> LENGTH: 47
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 50
aatttaatac gactcactat agggagacgg tatcaggagc ggatagg                 47

<210> SEQ ID NO 51
<211> LENGTH: 47
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 51
aatttaatac gactcactat agggagacta ccagactcaa gcctgcc                 47
```

```
<210> SEQ ID NO 52
<211> LENGTH: 48
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (16)..(48)
<223> OTHER INFORMATION: dT3dA30 immobilized probe-binding region

<400> SEQUENCE: 52
ccgacgaccg ugcautttaa aaaaaaaaaa aaaaaaaaaa aaaaaaaa                48

<210> SEQ ID NO 53
<211> LENGTH: 48
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (16)..(48)
<223> OTHER INFORMATION: dT3dA30 immobilized probe-binding region

<400> SEQUENCE: 53
ggcugcuggc acguatttaa aaaaaaaaaa aaaaaaaaaa aaaaaaaa                48

<210> SEQ ID NO 54
<211> LENGTH: 63
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (31)..(63)
<223> OTHER INFORMATION: dT3dA30 immobilized probe-binding region

<400> SEQUENCE: 54
ccgguguucu uccaaauauc ugcgcauuuc tttaaaaaaa aaaaaaaaa aaaaaaaaaa    60 aaa                                                                63

<210> SEQ ID NO 55
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (8)..(34)

<400> SEQUENCE: 55
tggtaagaat ttaatacgac tcactatagg gagataagcc gttaccttac ca           52

<210> SEQ ID NO 56
<211> LENGTH: 51
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (19)..(51)
<223> OTHER INFORMATION: dT3dA30 immobilized probe-binding region

<400> SEQUENCE: 56
cccaccaacu agcuaacatt taaaaaaaaa aaaaaaaaaa aaaaaaaaaa a             51
```

<210> SEQ ID NO 57
<211> LENGTH: 43
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 57
aatttaatac gactcactat agggagaagc ctaggtgggc cat                43

<210> SEQ ID NO 58
<211> LENGTH: 47
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 58
aatttaatac gactcactat agggagatca gtcccaatgt ggccgtc             47

<210> SEQ ID NO 59
<211> LENGTH: 44
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 59
aatttaatac gactcactat agggagagtc ccaatgtggc cgtc                44

<210> SEQ ID NO 60
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 60
acgggtggta atgctg                                               16

<210> SEQ ID NO 61
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 61
tgctccagaa tagctcttg                                            19

<210> SEQ ID NO 62
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 62

```
tccagaatag ctcttg                                                       16

<210> SEQ ID NO 63
<211> LENGTH: 51
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (19)..(51)
<223> OTHER INFORMATION: dT3dA30 immobilized probe-binding region

<400> SEQUENCE: 63
agguugguca cgcauuactt taaaaaaaaa aaaaaaaaa aaaaaaaaaa a                  51

<210> SEQ ID NO 64
<211> LENGTH: 42
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 64
aatttaatac gactcactat agggagacat gccactaaac ac                          42

<210> SEQ ID NO 65
<211> LENGTH: 49
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (7)..(33)

<400> SEQUENCE: 65
gtttagaatt taatacgact cactataggg agatcccatg ccactaaac                   49

<210> SEQ ID NO 66
<211> LENGTH: 53
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (9)..(35)

<400> SEQUENCE: 66
gtgtttagaa tttaatacga ctcactatag ggagatccca tgccactaaa cac              53

<210> SEQ ID NO 67
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (20)..(52)
<223> OTHER INFORMATION: dT3dA30 immobilized probe-binding region

<400> SEQUENCE: 67
caacucggcu augcaucaut ttaaaaaaaa aaaaaaaaaa aaaaaaaaaa aa               52
```

<210> SEQ ID NO 68
<211> LENGTH: 51
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (19)..(51)
<223> OTHER INFORMATION: dT3dA30 immobilized probe-binding region

<400> SEQUENCE: 68
cucucaacuc ggcuaugctt taaaaaaaaa aaaaaaaaaa aaaaaaaaaa a         51

<210> SEQ ID NO 69
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (20)..(52)
<223> OTHER INFORMATION: dT3dA30 immobilized probe-binding region

<400> SEQUENCE: 69
accgucaaau aaaggccagt ttaaaaaaaa aaaaaaaaaa aaaaaaaaaa aa        52

<210> SEQ ID NO 70
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 70
aggucaggag uuaaaucugg gaccu                                      25

<210> SEQ ID NO 71
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 71
ggtgaagaaa gatagagg                                              18

<210> SEQ ID NO 72
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 72
ccguccuggc cuuuauuuga cgg                                        23

<210> SEQ ID NO 73
<211> LENGTH: 44
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

```
<400> SEQUENCE: 73
aatttaatac gactcactat agggagagtg actttctggt tgat            44

<210> SEQ ID NO 74
<211> LENGTH: 46
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 74
aatttaatac gactcactat agggagaccg tgactttcta agtaat          46

<210> SEQ ID NO 75
<211> LENGTH: 49
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (17)..(49)
<223> OTHER INFORMATION: dT3dA30 immobilized probe-binding region

<400> SEQUENCE: 75
acgcuugcca ccuacgttta aaaaaaaaa aaaaaaaaa aaaaaaaa           49

<210> SEQ ID NO 76
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 76
cggaactaac agatttac                                         18

<210> SEQ ID NO 77
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 77
cttgcaccag atgaaact                                         18

<210> SEQ ID NO 78
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 78
gcttgcacca gatgaaacta g                                     21

<210> SEQ ID NO 79
<211> LENGTH: 21
<212> TYPE: DNA
<213> ORGANISM: Artificial Sequence
<220> FEATURE:
<223> OTHER INFORMATION: Synthetic Oligonucleotide
```

```
<400> SEQUENCE: 79
gtgcttgcac cagatgaaac t                                      21

<210> SEQ ID NO 80
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 80
gtgaagaaag atagag                                            16

<210> SEQ ID NO 81
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 81
atgctggatg ctccaactt                                         19

<210> SEQ ID NO 82
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 82
ccagaagguc aggaguuaaa ucugg                                  25

<210> SEQ ID NO 83
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 83
ggucaggagu uaaaucuggg acc                                    23

<210> SEQ ID NO 84
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 84
acucccuguu aggucaggag u                                      21

<210> SEQ ID NO 85
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 85
acuccguuag gucaggagu                                         19

<210> SEQ ID NO 86
```

```
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 86
aggucaggag uuaaaucugg accu                                              24

<210> SEQ ID NO 87
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 87
ggucaggagu uaaaucuuga cc                                                22

<210> SEQ ID NO 88
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 88
ucaggaguua aaucuccuga                                                   20

<210> SEQ ID NO 89
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 89
acaaatcacc gtaccctaga gggatatcac tcagcataat ttaatgattt gt               52

<210> SEQ ID NO 90
<211> LENGTH: 53
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 90
acaaatcacc gtaccctaga gggatatcac tcagcataat ttaagtgatt tgt              53

<210> SEQ ID NO 91
<211> LENGTH: 43
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 91
aatttaatac gactcactat agggagatac ccgtcgaagc cta                         43
```

```
<210> SEQ ID NO 92
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 92
gatgctccaa cttgacg                                                    17

<210> SEQ ID NO 93
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 93
tgctccaact tgacg                                                      15

<210> SEQ ID NO 94
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 94
cgtcagatgc tccaacttga cg                                              22

<210> SEQ ID NO 95
<211> LENGTH: 44
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 95
aatttaatac gactcactat agggagactg atcatgcgat ctgc                      44

<210> SEQ ID NO 96
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 96
gacugggaua acaccugcca guc                                             23

<210> SEQ ID NO 97
<211> LENGTH: 42
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 97
aatttaatac gactcactat agggagaccg tgactttctg gt                        42
```

```
<210> SEQ ID NO 98
<211> LENGTH: 44
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 98
aatttaatac gactcactat agggagacgt gactttctaa gtaa                44

<210> SEQ ID NO 99
<211> LENGTH: 46
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 99
gatctgcgta cagttctcaa gagggatatc actcagcata atttaa              46

<210> SEQ ID NO 100
<211> LENGTH: 50
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 100
aatttaatac gactcactat agggagactt ctttcatgcg aaagtagctt          50

<210> SEQ ID NO 101
<211> LENGTH: 50
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 101
aatttaatac gactcactat agggagactt ctttcatgcg atagtagctt          50

<210> SEQ ID NO 102
<211> LENGTH: 53
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (10)..(36)

<400> SEQUENCE: 102
tgtttagtga atttaatacg actcactata gggagatccc atgccactaa aca       53

<210> SEQ ID NO 103
<211> LENGTH: 52
<212> TYPE: DNA
<213> ORGANISM: Artificial Sequence
```

```
<220> FEATURE:
<223> OTHER INFORMATION: Synthetic Oligonucleotide
<220> FEATURE:
<221> NAME/KEY: promoter
<222> LOCATION: (6)..(32)

<400> SEQUENCE: 103
ggcagaattt aatacgactc actataggga gactaccaga ctcaagcctg cc        52

<210> SEQ ID NO 104
<211> LENGTH: 53
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (7)..(33)

<400> SEQUENCE: 104
ggcaggaatt taatacgact cactataggg agactaccag actcaagcct gcc       53

<210> SEQ ID NO 105
<211> LENGTH: 54
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (8)..(34)

<400> SEQUENCE: 105
ggcaggcaat ttaatacgac tcactatagg gagactacca gactcaagcc tgcc      54

<210> SEQ ID NO 106
<211> LENGTH: 55
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (9)..(35)

<400> SEQUENCE: 106
ggcaggctaa tttaatacga ctcactatag ggagactacc agactcaagc ctgcc     55

<210> SEQ ID NO 107
<211> LENGTH: 56
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (10)..(36)

<400> SEQUENCE: 107
ggcaggctta atttaatacg actcactata gggagactac cagactcaag cctgcc    56

<210> SEQ ID NO 108
<211> LENGTH: 44
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
```

<222> LOCATION: (1)..(27)

<400> SEQUENCE: 108
aatttaatac gactcactat agggagatcc catgccacta aaca                    44

<210> SEQ ID NO 109
<211> LENGTH: 43
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 109
aatttaatac gactcactat agggagacca tcccatgcca cta                     43

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 115
ccaugucuug uugggaaagc augg                                          24

<210> SEQ ID NO 116
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 116
ccaguguuua guggcauggg augcacugg                                     29

<210> SEQ ID NO 117
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 117
gagcttgcct agatgaattt g                                        21

<210> SEQ ID NO 118
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 118
gcttgcctag atgaatttgg t                                        21

<210> SEQ ID NO 119
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 119
gagcttgcct agatgacttt g                                        21

<210> SEQ ID NO 120
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 120
gcttgcctag atgactttgg t                                        21

<210> SEQ ID NO 121
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 121
tgcttgcacc acatgaaact ag                                       22

<210> SEQ ID NO 122
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 122
cgaguaacac guggguaacc uguacucg                                 28

<210> SEQ ID NO 123
<211> LENGTH: 27
<212> TYPE: DNA
<213> ORGANISM: Artificial Sequence
<220> FEATURE:

<223> OTHER INFORMATION: Synthetic Oligonucleotide

<400> SEQUENCE: 123
cagguugagu aacacguggg uaaccug                                              27

<210> SEQ ID NO 124
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 124
cuggaaacag gugcuaauac cggauuccag                                           30

<210> SEQ ID NO 125
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 125
cugcauuagc uaguuggua a gguaugcag                                           29

<210> SEQ ID NO 126
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 126
cttcggaatg gaaataga                                                        18

<210> SEQ ID NO 127
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (13)..(13)
<223> OTHER INFORMATION: n is a or g or c or t/u, unknown, or other
      (any)

<400> SEQUENCE: 127
cttcggaatg ganataga                                                        18

<210> SEQ ID NO 128
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 128
cttcggaatg gagataga                                                        18

<210> SEQ ID NO 129
<211> LENGTH: 18
<212> TYPE: DNA
<213> ORGANISM: Artificial Sequence
<220> FEATURE:
<223> OTHER INFORMATION: Synthetic Oligonucleotide -continued

```
<400> SEQUENCE: 129
tgcaccaaat gaaactag                                                    18

<210> SEQ ID NO 130
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (8)..(8)
<223> OTHER INFORMATION: n is a or g or c or t/u, unknown, or other
      (any)

<400> SEQUENCE: 130
tgcaccanat gaaactag                                                    18

<210> SEQ ID NO 131
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 131
tgcaccatat gaaactag                                                    18

<210> SEQ ID NO 132
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 132
tcaggagtta aatctgg                                                     17

<210> SEQ ID NO 133
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 133
gttaggtcag gagttaaatc tgg                                              23

<210> SEQ ID NO 134
<211> LENGTH: 54
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (22)..(54)
<223> OTHER INFORMATION: dT3dA30 immobilized probe-binding region

<400> SEQUENCE: 134
cggccucguc ccugcugaaa gtttaaaaaa aaaaaaaaaa aaaaaaaaaa aaaa            54

<210> SEQ ID NO 135
<211> LENGTH: 61
<212> TYPE: DNA
<213> ORGANISM: Artificial Sequence
<220> FEATURE:
```

<223> OTHER INFORMATION: Synthetic Oligonucleotide
<220> FEATURE:
<221> NAME/KEY: misc_feature
<222> LOCATION: (29)..(61)
<223> OTHER INFORMATION: dT3dA30 immobilized probe-binding region

<400> SEQUENCE: 135
guaccgucac cuugcggccu cgucccugtt taaaaaaaaa aaaaaaaaaa aaaaaaaaa    60 a                                                                  61

<210> SEQ ID NO 136
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 136
auccgcuccu gaucggau                                                18

<210> SEQ ID NO 137
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 137
uauccgcucc ugauggaua                                               19

<210> SEQ ID NO 138
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 138
auccgcuccu gauacccgga u                                            21

<210> SEQ ID NO 139
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 139
cccuauccgc uccuuaggg                                               19

<210> SEQ ID NO 140
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 140
aggagcuauc cgcuccu                                                 17

<210> SEQ ID NO 141
<211> LENGTH: 25
<212> TYPE: DNA
<213> ORGANISM: Artificial Sequence
<220> FEATURE:
<223> OTHER INFORMATION: Synthetic Oligonucleotide

```
<400> SEQUENCE: 141
cgguaccuau ccgcuccuga uaccg                                          25

<210> SEQ ID NO 142
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 142
cgguacuauc cgcuccugau accg                                           24

<210> SEQ ID NO 143
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 143
cgguauaucc gcuccugaua ccg                                            23

<210> SEQ ID NO 144
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 144
cccuauccgc uccugauuag gg                                             22

<210> SEQ ID NO 145
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 145
gcuccugaua ccggcaggga gc                                             22

<210> SEQ ID NO 146
<211> LENGTH: 44
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 146
aatttaatac gactcactat agggagaatc aggagcggat aggg                     44

<210> SEQ ID NO 147
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 147
aatcttgcac aatgggcgaa a                                              21
```

<210> SEQ ID NO 148
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 148
cuugcgacga ggccgcaag                                                19

<210> SEQ ID NO 149
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 149
gcagggacga ggccgccugc                                               20

<210> SEQ ID NO 150
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 150
cuugcggacg aggccgcaag                                               20

<210> SEQ ID NO 151
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 151
ucagcaggga cgaggccgcu ga                                            22

<210> SEQ ID NO 152
<211> LENGTH: 49
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 152
aatttaatac gactcactat agggagaccg gggcttcttc tgcaggtac               49

<210> SEQ ID NO 153
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 153
gucugggaua ccacuugcag ac                                            22

<210> SEQ ID NO 154
<211> LENGTH: 28

```
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n is a or g or c or t/u, unknown, or other
      (any)
<220> FEATURE:
<221> NAME/KEY: misc_feature
<222> LOCATION: (16)..(16)
<223> OTHER INFORMATION: n is a or g or c or t/u, unknown, or other
      (any)

<400> SEQUENCE: 154
cgaguaacnc gugggnaacc uguacucg                                          28

<210> SEQ ID NO 155
<211> LENGTH: 51
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (8)..(34)

<400> SEQUENCE: 155
tgtttagaat ttaatacgac tcactatagg gagatcccat gccactaaac a               51

<210> SEQ ID NO 156
<211> LENGTH: 54
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (11)..(37)

<400> SEQUENCE: 156
tgtttagtgg aatttaatac gactcactat agggagatcc catgccacta aaca            54

<210> SEQ ID NO 157
<211> LENGTH: 55
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (12)..(38)

<400> SEQUENCE: 157
tgtttagtgg caatttaata cgactcacta tagggagatc ccatgccact aaaca            55

<210> SEQ ID NO 158
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 158
cgcaugucuu guugggaaug cg                                                22

<210> SEQ ID NO 159
<211> LENGTH: 24
```

```
<212> TYPE: DNA
<213> ORGANISM: Artificial Sequence
<220> FEATURE:
<223> OTHER INFORMATION: Synthetic Oligonucleotide

<400> SEQUENCE: 159
ccaugucuug uugggaaagc augg                                    24

<210> SEQ ID NO 160
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 160
caugucuugu ugggaaagga caug                                    24

<210> SEQ ID NO 161
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 161
acgcaugucu agaguugcgu                                         20

<210> SEQ ID NO 162
<211> LENGTH: 50
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (6)..(32)

<400> SEQUENCE: 162
tctggaattt aatacgactc actataggga gaccatcttc ccctaccaga        50

<210> SEQ ID NO 163
<211> LENGTH: 45
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 163
aatttaatac gactcactat agggagaaca tgcgtctagt gttgt             45

<210> SEQ ID NO 164
<211> LENGTH: 45
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 164
aatttaatac gactcactat agggagaaca agcgtctagt gttgt             45
```

```
<210> SEQ ID NO 165
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 165
ctttcagcag ggacgaggcc                                               20

<210> SEQ ID NO 166
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 166
ggtacctgca gaagaagc                                                 18

<210> SEQ ID NO 167
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 167
acctgcagaa gaagcccc                                                 18

<210> SEQ ID NO 168
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 168
ggtacctgca gaagaagccc cgg                                           23

<210> SEQ ID NO 169
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 169
acctgcagaa gaagccccgg                                               20

<210> SEQ ID NO 170
<211> LENGTH: 46
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 170
aatttaatac gactcactat agggagagta tcggctcaac tctctg                  46

<210> SEQ ID NO 171
<211> LENGTH: 51
<212> TYPE: DNA
<213> ORGANISM: Artificial Sequence
```

```
<220> FEATURE:
<223> OTHER INFORMATION: Synthetic Oligonucleotide
<220> FEATURE:
<221> NAME/KEY: promoter
<222> LOCATION: (6)..(32)

<400> SEQUENCE: 171
cagagaattt aatacgactc actataggga gtatcggc tcaactctct g         51

<210> SEQ ID NO 172
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 172
tgcctagatg aatttggtgc                                          20

<210> SEQ ID NO 173
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 173
tgcttgcacc aaatgaaac                                           19

<210> SEQ ID NO 174
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 174
tgcctataga agttcttc                                            18

<210> SEQ ID NO 175
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 175
ttcttcggaa tggaaa                                              16

<210> SEQ ID NO 176
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 176
cggaactaac agatttactt cg                                       22

<210> SEQ ID NO 177
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 177
```
tacttcggta atgacgt					17

<210> SEQ ID NO 178
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 178
ccaucagcga gcggcggaug g					21

<210> SEQ ID NO 179
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 179
cauccgcgag cggcggaug					19

<210> SEQ ID NO 180
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 180
gccguagaua caagcuagcg gc					22

<210> SEQ ID NO 181
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 181
gccguaggaa agcgagcggc					20

<210> SEQ ID NO 182
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 182
cugcccaaga gucuggggca g					21

<210> SEQ ID NO 183
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 183
cugcccuuua gucugggca g					21

<210> SEQ ID NO 184
<211> LENGTH: 24
<212> TYPE: DNA

```
<213> ORGANISM: Artificial Sequence
<220> FEATURE:
<223> OTHER INFORMATION: Synthetic Oligonucleotide

<400> SEQUENCE: 184
gguaucccca uagucuggga uacc                                          24

<210> SEQ ID NO 185
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 185
guuaucccaa gagacuggga uaac                                          24

<210> SEQ ID NO 186
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 186
accugcccaa gagacuggga ggu                                           23

<210> SEQ ID NO 187
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 187
ccugccccau agucugggca gg                                            22

<210> SEQ ID NO 188
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 188
accugcccca uagucuggga ggu                                           23

<210> SEQ ID NO 189
<211> LENGTH: 46
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 189
aatttaatac gactcactat agggagactt ggtaagcctt taccttt                 46

<210> SEQ ID NO 190
<211> LENGTH: 46
<212> TYPE: DNA
<213> ORGANISM: Artificial Sequence
<220> FEATURE:
<223> OTHER INFORMATION: Synthetic Oligonucleotide
<220> FEATURE:
```

```
<221> NAME/KEY: promoter
<222> LOCATION: (1)..(27)

<400> SEQUENCE: 190
aatttaatac gactcactat agggagactt ggtaagccgt taccctt          46

<210> SEQ ID NO 191
<211> LENGTH: 43
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 191
aatttaatac gactcactat agggagatag cgacagctta cgc              43

<210> SEQ ID NO 192
<211> LENGTH: 50
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 192
aatttaatac gactcactat agggagacag aaccatcttt taaactctag        50

<210> SEQ ID NO 193
<211> LENGTH: 47
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 193
aatttaatac gactcactat agggagatcc aaatggtatc ccagact           47

<210> SEQ ID NO 194
<211> LENGTH: 49
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 194
aatttaatac gactcactat agggagagtt tccaggtggt atcccagac         49

<210> SEQ ID NO 195
<211> LENGTH: 46
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 195
```
aatttaatac gactcactat agggagatcc aggtgttatc ccagtc         46

<210> SEQ ID NO 196
<211> LENGTH: 50
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 196
aatttaatac gactcactat agggagagtt tccaggtggt atcccagtct    50

<210> SEQ ID NO 197
<211> LENGTH: 46
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 197
aatttaatac gactcactat agggagagag tgatagcaga accatc        46

<210> SEQ ID NO 198
<211> LENGTH: 44
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 198
aatttaatac gactcactat agggagaagt gatagcagaa ccat          44

<210> SEQ ID NO 199
<211> LENGTH: 47
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 199
aatttaatac gactcactat agggagattt catgcgaaag tagcttt       47

<210> SEQ ID NO 200
<211> LENGTH: 47
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 200
aatttaatac gactcactat agggagaaaa gtagcttttatccggta        47

```
<210> SEQ ID NO 201
<211> LENGTH: 46
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 201
aatttaatac gactcactat agggagagct tacgccgcct tttaaa            46

<210> SEQ ID NO 202
<211> LENGTH: 43
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 202
aatttaatac gactcactat agggagaaca gcttacgccg cct               43

<210> SEQ ID NO 203
<211> LENGTH: 47
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 203
aatttaatac gactcactat agggagagct tacgccgcct tttaaaa           47

<210> SEQ ID NO 204
<211> LENGTH: 43
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 204
aatttaatac gactcactat agggagaatc tgctttctta tcc               43

<210> SEQ ID NO 205
<211> LENGTH: 44
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 205
aatttaatac gactcactat agggagattt taaaagctga tcat              44

<210> SEQ ID NO 206
<211> LENGTH: 16
<212> TYPE: DNA
<213> ORGANISM: Artificial Sequence
```

```
<220> FEATURE:
<223> OTHER INFORMATION: Synthetic Oligonucleotide

<400> SEQUENCE: 206
ggacgaggcc gcaagg                                                    16

<210> SEQ ID NO 207
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 207
agggacgagg ccgcaag                                                   17

<210> SEQ ID NO 208
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 208
taggcggtct gttaggtca                                                 19

<210> SEQ ID NO 209
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 209
cgtaggcggt ctgttag                                                   17

<210> SEQ ID NO 210
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 210
ccuauccgcu ccugauacga uagg                                           24

<210> SEQ ID NO 211
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 211
cgguauccua uccgcuccug auaccg                                         26

<210> SEQ ID NO 212
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 212
cugccgcucc ugauaccggc ag                                             22
```

<210> SEQ ID NO 213
<211> LENGTH: 46
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 213
aatttaatac gactcactat agggagaagt catggcccag aagacc        46

<210> SEQ ID NO 214
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 214
caggugcaag agacugggau aacaccug        28

<210> SEQ ID NO 215
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 215
ccaagagacu gggauaacac ucuugg        26

<210> SEQ ID NO 216
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 216
caggugagag acugggauaa caccug        26

<210> SEQ ID NO 217
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 217
cagaugcuaa uaccggauac aucug        25

<210> SEQ ID NO 218
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 218
cggauaacaa cacuagacgu auccg        25

<210> SEQ ID NO 219
<211> LENGTH: 25
<212> TYPE: DNA

```
<213> ORGANISM: Artificial Sequence
<220> FEATURE:
<223> OTHER INFORMATION: Synthetic Oligonucleotide

<400> SEQUENCE: 219
cgucuacgga uaacaacacu agacg                                          25

<210> SEQ ID NO 220
<211> LENGTH: 44
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 220
aatttaatac gactcactat agggagagta agccgttacc ttac                     44

<210> SEQ ID NO 221
<211> LENGTH: 57
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (25)..(57)
<223> OTHER INFORMATION: dT3dA30 immobilized probe-binding region

<400> SEQUENCE: 221
aagcgguuua caacccgaag gccutttaaa aaaaaaaaa aaaaaaaaa aaaaaaa         57

<210> SEQ ID NO 222
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (30)..(52)
<223> OTHER INFORMATION: dT3dA30 immobilized probe-binding region

<400> SEQUENCE: 222
uccaucagac uugcguccat ttaaaaaaaa aaaaaaaaa aaaaaaaaaa aa             52

<210> SEQ ID NO 223
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 223
ggtagtgaag aaagataga                                                 19

<210> SEQ ID NO 224
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 224
tctatctggt agtgaagaaa gataga                                         26
```

<210> SEQ ID NO 225
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 225
agtgaagaag gttttcggat                                         20

<210> SEQ ID NO 226
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 226
atccgagtga agaaggtttt cggat                                   25

<210> SEQ ID NO 227
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 227
cctctatggt gaagaaagat agagg                                   25

<210> SEQ ID NO 228
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 228
cuugcgacga ggccgcaag                                          19

<210> SEQ ID NO 229
<211> LENGTH: 48
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 229
aatttaatac gactcactat agggagatcc atcttcccct accagact          48

<210> SEQ ID NO 230
<211> LENGTH: 51
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 230
aatttaatac gactcactat agggagattc catcttcccc taccagactc a       51

```
<210> SEQ ID NO 231
<211> LENGTH: 50
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 231
aatttaatac gactcactat agggagaatt ccatcttccc ctaccagact            50

<210> SEQ ID NO 232
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 232
tgttaggtca ggagttaaat ct                                          22

<210> SEQ ID NO 233
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 233
gcuccugaua ccggcagggg agc                                         23

<210> SEQ ID NO 234
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 234
cuccugauac cggcagagga g                                           21

<210> SEQ ID NO 235
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 235
gcuccugaua ccggcaggag c                                           21

<210> SEQ ID NO 236
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 236
ugccgcuccu gauaccggca                                             20

<210> SEQ ID NO 237
<211> LENGTH: 21
<212> TYPE: DNA
<213> ORGANISM: Artificial Sequence
```

```
<220> FEATURE:
<223> OTHER INFORMATION: Synthetic Oligonucleotide

<400> SEQUENCE: 237
ugccggcucc ugauaccggc a                                              21

<210> SEQ ID NO 238
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 238
cgguauaucc gcuccugaua ccg                                            23

<210> SEQ ID NO 239
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 239
gguauuaucc gcuccugaua ccg                                            23

<210> SEQ ID NO 240
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 240
gguauuaucc gcuccugaua cc                                             22

<210> SEQ ID NO 241
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 241
cugccuccug auaccggcag                                                20

<210> SEQ ID NO 242
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 242
cgguacuauc cgcuccugau accg                                           24

<210> SEQ ID NO 243
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 243
auccgcuccu gauacccgga u                                              21
```

```
<210> SEQ ID NO 244
<211> LENGTH: 53
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (7)..(33)

<400> SEQUENCE: 244
tctggaaatt taatacgact cactataggg agaaccatct tcccctatcc aga        53

<210> SEQ ID NO 245
<211> LENGTH: 54
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (8)..(34)

<400> SEQUENCE: 245
tctggataat ttaatacgac tcactatagg gagaaccatc ttcccctatc caga        54

<210> SEQ ID NO 246
<211> LENGTH: 55
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (9)..(35)

<400> SEQUENCE: 246
tctggataaa tttaatacga ctcactatag ggagaaccat cttcccctat ccaga       55

<210> SEQ ID NO 247
<211> LENGTH: 56
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (10)..(36)

<400> SEQUENCE: 247
tctggataga atttaatacg actcactata gggagaacca tcttcccta tccaga       56

<210> SEQ ID NO 248
<211> LENGTH: 51
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (7)..(33)

<400> SEQUENCE: 248
tctggtaatt taatacgact cactataggg agaccatctt ccctaccag a            51

<210> SEQ ID NO 249
<211> LENGTH: 52
<212> TYPE: DNA
```

<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (8)..(34)

<400> SEQUENCE: 249
tctggtaaat ttaatacgac tcactatagg gagaccatct tccccctacca ga         52

<210> SEQ ID NO 250
<211> LENGTH: 53
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (9)..(35)

<400> SEQUENCE: 250
tctggtagaa tttaatacga ctcactatag ggagaccatc ttcccctacc aga        53

<210> SEQ ID NO 251
<211> LENGTH: 54
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (10)..(36)

<400> SEQUENCE: 251
tctggtagga atttaatacg actcactata gggagaccat cttcccctac caga       54

<210> SEQ ID NO 252
<211> LENGTH: 45
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 252
aatttaatac gactcactat agggagaggt atcaggagcg atag              45

<210> SEQ ID NO 253
<211> LENGTH: 44
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 253
aatttaatac gactcactat agggagaggt atcaggagcg gata              44

<210> SEQ ID NO 254
<211> LENGTH: 23
<212> TYPE: DNA
<213> ORGANISM: Artificial Sequence
<220> FEATURE:
<223> OTHER INFORMATION: Synthetic Oligonucleotide

```
<400> SEQUENCE: 254
gauccgcucc ugauacccgg auc                                        23

<210> SEQ ID NO 255
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 255
gcgguacuau ccgcuccuga uaccgc                                     26

<210> SEQ ID NO 256
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 256
cuccugauac cggcagagga g                                          21

<210> SEQ ID NO 257
<211> LENGTH: 45
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (13)..(45)
<223> OTHER INFORMATION: dT3dA30 immobilized probe-binding region

<400> SEQUENCE: 257
ucuguuaguu cctttaaaaa aaaaaaaaaa aaaaaaaaaa aaaaa                45

<210> SEQ ID NO 258
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 258
cggatgggtg agtaac                                                16

<210> SEQ ID NO 259
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 259
cacucacgca ugucuagagu g                                          21

<210> SEQ ID NO 260
<211> LENGTH: 50
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (18)..(50)
<223> OTHER INFORMATION: dT3dA30 immobilized probe-binding region
```

```
<400> SEQUENCE: 260
caugcuccgc cgcuuguttt aaaaaaaaaa aaaaaaaaaa aaaaaaaaaa                    50

<210> SEQ ID NO 261
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 261
ccugcagaga ugugguuucg cagg                                                24
```

US 12,291,753 B2

COMPOSITIONS AND METHODS FOR DETECTING BACTERIAL NUCLEIC ACID AND DIAGNOSING BACTERIAL VAGINOSIS

CROSS-REFERENCE TO RELATED APPLICATIONS

This application is a continuation of International application No. PCT/US2019/047854, filed Aug. 23, 2019, which claims the benefit of priority of U.S. Provisional Patent Application No. 62/722,627, filed Aug. 24, 2018, which is incorporated by reference herein in its entirety for all purposes.

SEQUENCE LISTING

The instant application contains a Sequence Listing which has been submitted in ASCII format via EFS-Web and is hereby incorporated by reference in its entirety. Said ASCII copy, created on Aug. 20, 2019, is named 2019 Aug. 20 01159-0039-OOPCT_Seq_List_ST25.txt and is 68 KB in size.

BACKGROUND OF THE INVENTION

According to the National Health and Nutrition Examination Survey, nearly a third of women between the age of 14 and 49 have bacterial vaginosis (BV). (See Allsworth and Peipert, Obstetrics and Gynecology 109:114-120, 2007). BV is the most common cause of vaginal discharge and a reason many women seek medical attention. It is also associated with preterm birth, low birth weight, pelvic inflammatory disease, an increase in STD infections, including HIV, and a greater risk of passing HIV on to sex partners. See Srinivasan and Fredricks, Interdisciplinary Perspectives on Infectious Diseases, Vol. 2008, Article ID 750479, 22 pages, 2008). Women with bacterial vaginosis may have symptoms including a malodorous vaginal discharge or irritation, however, as many as half of the women with diagnosable BV have no clear symptoms (see Srivinvasan and Fredricks, supra).

No single etiologic agent is known to be the cause of BV. Most researchers and the CDC consider bacterial vaginosis to be the result of a disruption to the normal bacterial flora of the vagina. Unlike common infections, this dysbiosis is not the result of an individual bacterial species. See CDC Factsheet, 2014 (BV-Fact-Sheet-March-2014.pdf, from CDC website). A dysbiosis is a disruption of the normal microbiota within a body environment such as the vagina. See Nibali et al., Journal of Oral Microbiology 6:22962, 2014.

BV is diagnosed in the clinic using the Amsel Criteria and in the laboratory using the Nugent Scoring System. The later relies on counting bacterial morphotypes with the aid of the Gram stain. In this way, the Nugent Score is a visual assessment of dysbiosis—it scores the bad bacteria against the good. See Nugent et al., Journal of Clinical Microbiology 29:297-301, 1991. The Amsel Criteria evaluates a sample for the presence of clue cells, pH, color and odor which are key symptoms associated with BV. See Amsel et al., Am. J. Med. 74:14-22, 1983. A wet mount of the sample is examined with a microscope to detect clue cells which are human epithelial cells covered with bacteria thought to predominately consist of G. vaginalis.

Molecular tests generally target multiple organisms which have strong correlations with bacterial vaginosis. Which organisms are targeted varies from test to test. In nearly all cases, high abundance anaerobic bacteria are targeted such as Atopobium, Gardnerella, and Megasphaera species.

The only FDA approved tests for BV are the BD Affirm™ VPIII Microbial Identification Test (2010) and the BD MAX™ Vaginal Panel (2016). Both the Affirm and MAX products detect G. vaginalis as the sole indicator of BV. The BD Affirm VPIII test was found to have a sensitivity of 67.6% and a specificity of 76.4% in a study by Cartwright et al. (Journal of Clinical Microbiology 51:3694-3699, 2013). The BD Affirm VIII package insert indicates that the Affirm product is 95.1% sensitive and 83.3% specific when compared to a scored gram stain method, while the BD MAX package insert indicates that the MAX product is 90.5% sensitive and 85.8% specific.

Cartwright et al., supra, used a multiplex assay for the detection of Atopobium vaginae, BVAB-2 and Megasphaera-1 for the diagnosis of BV. They measured the performance of this assay against a combination of Nugent and Amsel results in a population of 323 women (93% African-American, 7% white non-Hispanic). They reported this test was 96.9% sensitive and 92.6% specific when compared to the combination of Nugent and Amsel scores. They did not report the results of this assay relative to the Nugent Score alone.

SUMMARY OF THE INVENTION

In one aspect, the present invention provides a method for determining the presence or absence of Bacterial Vaginosis (BV) in a subject. In some embodiments, the method generally includes the following steps: (a) providing a sample from a subject suspected of having BV: (b) performing an assay for the detection of Lactobacillus sp., A. vaginae. and G. vaginalis in the sample: (c) for each of Lactobacillus sp., A. vaginae. and G. vaginalis, assigning a quantitative value based on the detection assay: (d) subtracting the Lactobacillus sp. quantitative value from the greater of the A. vaginae quantitative value and the G. vaginalis quantitative value: (e) assigning a single BV score based on step (d); and (f) determining the presence or absence of BV in the subject based on a comparison of the BV score to a cutoff value. In some embodiments, at step (c), a minimum quantitative value is imposed for Lactobacillus sp. and/or for A. vaginae and G. vaginalis. Typically, the quantitative value for each of Lactobacillus sp., A. vaginae. and G. vaginalis is standardized and/or weighted. In some variations comprising standardized quantitative values, the quantitative value for each of Lactobacillus sp., A. vaginae. and G. vaginalis is in units of log copies and standardization includes subtracting a median population value from a value determined from the detection assay. Step (d) may further include addition of an adjustment constant. In certain embodiments, step (d) further includes adding an internal control (IC) adjustment factor that compensates for sample inhibition of the detection assay, where the IC adjustment factor is based on a ratio of (i) an observed IC value generated from the detection assay to (ii) an expected IC value for the detection assay. In specific variations, the BV score is assigned using the equation BV score=$C_0+W_L$Max ($L_S$, $F_{LS}$)+$W_{GA}$Max (As, Gs, $F_{GAS}$)+$W_{IC}$ Log 2 (ICRatio), where $C_0$ is an adjustment constant: WL is a weighting constant for Lactobacillus sp.: Max ($L_S$, $F_{LS}$) is the greater of $L_S$ and $F_{LS}$, where $L_S$ is an observed standardized quantitative value for Lactobacillus sp. and $F_{LS}$ is an imposed minimum standardized quantitative value for Lactobacillus sp.: $W_{GA}$ is a weighting constant for A. vaginae and G. vaginalis: Max (As, Gs, $F_{GAS}$) is the greater of As, Gs, and F$_{GAS}$, where As is an observed standardized quantitative value for A. vaginae, Gs is an observed standardized quantitative value for G. vaginalis, and F$_{GAS}$ is an imposed minimum standardized quantitative value for A. vaginae and G. vaginalis (e.g., 0): W$_{IC}$ is an internal control (IC) weighting constant; and ICRatio is a ratio of (i) an observed internal control (IC) value generated from the detection assay to (ii) an expected IC value for the detection assay.

In some embodiments of a method for diagnosing BV as above, the assay for detection of Lactobacillus sp., A. vaginae, and G. vaginalis is a nucleic-acid-based detection assay. Particularly suitable nucleic-acid-based detection assays include amplification-based assays such as, for example, an assay comprising an isothermal amplification reaction (e.g., a transcription-mediated amplification (TMA) reaction), which may be performed in real time. In certain embodiments, the nucleic-acid-based detection assay targets the 16S IRNA of Lactobacillus sp., A. vaginae, and G. vaginalis. In particular variations, the nucleic-acid-based detection assay targets (i) a L. crispatus 16S rRNA region corresponding to a region of SEQ ID NO:1 from about nucleotide position 40 to about nucleotide position 265: (ii) a L. jensenii 16S rRNA region corresponding to a region of SEQ ID NO:2 from about nucleotide position 43 to about nucleotide position 247: (iii) a L. gasseri 16S rRNA region corresponding to a region of SEQ ID NO:3 from about nucleotide position 93 to about nucleotide position 298: (iv) a A. vaginae 16S rRNA region corresponding to a region of SEQ ID NO: 4 from about nucleotide position 540 to about nucleotide position 625; and/or (v) a G. vaginalis 16S rRNA region corresponding to a region of SEQ ID NO:5 from about nucleotide position 172 to about nucleotide position 227.

In certain embodiments of a method for diagnosing BV as above comprising a nucleic-acid-based detection assay, the assay is an amplification-based assay including the following steps:

(1) contacting the sample with first, second, third, and fourth Lactobacillus-specific amplification oligomers for amplifying a target region of a Lactobacillus sp. target nucleic acid, where (i) the first Lactobacillus-specific amplification oligomer comprises a first Lactobacillus-specific target-hybridizing sequence substantially corresponding to the nucleotide sequence of residues 28-45 of SEQ ID NO: 10: (ii) the second Lactobacillus-specific amplification oligomer comprises a second Lactobacillus-specific target-hybridizing sequence substantially corresponding to the nucleotide sequence of SEQ ID NO:7: (iii) the third Lactobacillus-specific amplification oligomer comprises a third Lactobacillus-specific target-hybridizing sequence substantially corresponding to the nucleotide sequence of SEQ ID NO:8; and (iv) the fourth Lactobacillus-specific amplification oligomer comprises a fourth Lactobacillus-specific target-hybridizing sequence substantially corresponding to the nucleotide sequence of SEQ ID NO:9:

first and second A. vaginae-specific amplification oligomers for amplifying a target region of a A. vaginae target nucleic acid, wherein (i) the first A. vaginae-specific amplification oligomer comprises a first A. vaginae-specific target-hybridizing sequence substantially corresponding to the nucleotide sequence of residues 28-45 of SEQ ID NO:18 and (ii) the second A. vaginae-specific amplification oligomer comprises a second A. vaginae-specific target-hybridizing sequence substantially corresponding to the nucleotide sequence of SEQ ID NO: 17; and first and second G. vaginalis-specific amplification oligomers for amplifying a target region of a G. vaginalis target nucleic acid, where (i) the first G. vaginalis-specific amplification oligomer comprises a first G. vaginalis-specific target-hybridizing sequence substantially corresponding to the nucleotide sequence of residues 36-52 of SEQ ID NO: 15 and (ii) the second G. vaginalis-specific amplification oligomer comprises a second G. vaginalis-specific target-hybridizing sequence substantially corresponding to the nucleotide sequence of SEQ ID NO: 14:

(2) performing an in vitro nucleic acid amplification reaction, wherein any Lactobacillus sp., A. vaginae. and G. vaginalis target nucleic acid, if present in the sample, is used as a template for generating one or more amplification products corresponding to the Lactobacillus sp., A. vaginae. and G. vaginalis target regions; and (3) detecting the presence or absence of the one or more amplification products.

In some variations of a method for diagnosing BV comprising an amplification-based detection assay as above, the first Lactobacillus-specific target-hybridizing sequence comprises the nucleotide sequence of residues 28-45 of SEQ ID NO:10; the second Lactobacillus-specific target-hybridizing sequence comprises the nucleotide sequence of SEQ ID NO:7; the third Lactobacillus-specific target-hybridizing sequence comprises the nucleotide sequence of SEQ ID NO:8; the fourth Lactobacillus-specific target-hybridizing sequence comprises the nucleotide sequence of SEQ ID NO:9; the first A. vaginae-specific target-hy bridizing sequence comprises the nucleotide sequence of residues 28-45 of SEQ ID NO: 18: the second A. vaginae-specific target-hybridizing sequence comprises the nucleotide sequence of SEQ ID NO: 17: the first G. vaginalis-specific target-hybridizing sequence comprises the nucleotide sequence of residues 36-52 of SEQ ID NO: 15; and/or the second G. vaginalis-specific target-hybridizing sequence comprises the nucleotide sequence of SEQ ID NO: 14. In some such embodiments, the first Lactobacillus-specific target-hybridizing sequence consists of the nucleotide sequence of residues 28-45 of SEQ ID NO: 10: the second Lactobacillus-specific target-hybridizing sequence consists of the nucleotide sequence of SEQ ID NO:7: the third Lactobacillus-specific target-hybridizing sequence consists of the nucleotide sequence of SEQ ID NO:8; the fourth Lactobacillus-specific target-hybridizing sequence consists of the nucleotide sequence of SEQ ID NO:9; the first A. vaginae-specific target-hybridizing sequence consists of the nucleotide sequence of residues 28-45 of SEQ ID NO: 18: the second A. vaginae-specific target-hybridizing sequence consists of the nucleotide sequence of SEQ ID NO: 17: the first G. vaginalis-specific target-hybridizing sequence consists of the nucleotide sequence of residues 36-52 of SEQ ID NO: 15; and/or the second G. vaginalis-specific target-hybridizing sequence consists of the nucleotide sequence of SEQ ID NO: 14.

In some embodiments of a method for diagnosing BV comprising an amplification-based detection assay as above, at least one of the first Lactobacillus-specific amplification oligomer, the first A. vaginae-specific amplification oligomer, and the first G. vaginalis-specific amplification oligomer is a promoter primer or promoter provider further comprising a promoter sequence located 5' to the respective target hybridizing sequence. A particularly suitable promoter sequence is a T7 promoter sequence such as, for example, a promoter sequence having the nucleotide sequence of residues 1-27 of SEQ ID NO: 10 (also shown as, e.g., residues 1-27 of SEQ ID NO: 18 or residues 9-35 of SEQ ID NO: 15). In specific variations, the first *Lactobacillus*-specific amplification oligomer comprises the nucleotide sequence of SEQ ID NO:10: the first A. vaginae-specific amplification oligomer comprises the nucleotide sequence of SEQ ID NO: 18; and/or the first *G. vaginalis*-specific amplification oligomer comprises the nucleotide sequence of residues 9-52 of SEQ ID NO: 15. In some embodiments, the first *G. vaginalis*-specific amplification oligomer comprises the nucleotide sequence of SEQ ID NO: 15.

In certain embodiments of a method for diagnosing BV comprising an amplification-based detection assay as above, the method further includes purifying the *Lactobacillus* sp., A. vaginae, and *G. vaginalis* target nucleic acids, if present, from other components in the sample before step (2). In some such embodiments, the purifying step includes contacting the sample with at least one capture probe oligomer comprising a target-hybridizing sequence covalently attached to a sequence or moiety that binds to an immobilized probe. For example, the sample may be contacted with a first capture probe oligomer comprising a target-hybridizing sequence that specifically hybridizes to a target sequence within the *Lactobacillus* sp. target nucleic acid and a second capture probe target-hybridizing sequence comprising a target-hybridizing sequence that specifically hybridizes to a target sequence within each of the A. vaginae and *G. vaginalis* target nucleic acids, where each of the first and second capture probe target-hybridizing sequences is covalently attached to the sequence or moiety that binds to the immobilized probe: in some such embodiments, the first capture probe target-hybridizing sequence specifically hybridizes to a target sequence within each of L. crispatus, L. *jensenii*, and L . . . gasseri target nucleic acid. In specific variations comprising first and second target capture probes as above, the first capture probe target-hybridizing sequence substantially corresponds to the nucleotide sequence of residues 1-19 of SEQ ID NO:6 and/or the second capture probe target-hybridizing sequence substantially corresponds to the nucleotide sequence of residues 1-20 of SEQ ID NO:13. In some embodiments, the first capture probe oligomer comprises the nucleotide sequence of SEQ ID NO:6 and/or the second capture probe oligomer comprises the nucleotide sequence of SEQ ID NO:13.

In some embodiments of a method for diagnosing BV comprising an amplification-based detection assay as above, the detecting step (3) comprises (i) contacting the one or more amplification products with a first *Lactobacillus*-specific detection probe comprising a target-hybridizing sequence that specifically hybridizes to the *Lactobacillus* sp. target region, a first A. vaginae-specific detection probe comprising a target-hybridizing sequence that specifically hybridizes to the A. vaginae target region, and a first *G. vaginalis*-specific detection probe comprising a target-hybridizing sequence that specifically hybridizes to the *G. vaginalis* target region, and (ii) detecting the presence or absence of any target-hybridized *Lactobacillus*-specific, A. vaginae-specific, and/or *G. vaginalis*-specific detection probe. In some embodiments, the first A. vaginae-specific detection probe target-hybridizing sequence substantially corresponds to the nucleotide sequence of residues 6-21 of SEQ ID NO: 19 and/or the first *G. vaginalis*-specific detection probe target-hybridizing sequence substantially corresponds to the nucleotide sequence of residues 1-18 of SEQ ID NO: 16: in more specific variations, the first A. vaginae-specific detection probe target-hybridizing sequence comprises the nucleotide sequence of residues 6-21 of SEQ ID NO: 19 and/or the first *G. vaginalis*-specific detection probe target-hybridizing sequence comprises the nucleotide sequence of residues 1-18 of SEQ ID NO:16. In some embodiments, the first *Lactobacillus*-specific detection probe target-hybridizing sequence specifically hybridizes to a target region of each of L. crispatus and L. *jensenii* target nucleic acid and the method further includes contacting the one or more amplification products with a second *Lactobacillus*-specific detection probe comprising a target-hybridizing sequence that specifically hybridizes to a target region of L. gasseri target nucleic acid: in some such embodiments, the first *Lactobacillus*-specific detection probe target-hybridizing sequence substantially corresponds to the nucleotide sequence of residues 1-17 of SEQ ID NO:11 and/or the second *Lactobacillus*-specific detection probe target-hybridizing sequence substantially corresponds to the nucleotide sequence of residues 7-23 of SEQ ID NO: 12: in more specific variations, the first *Lactobacillus*-specific detection probe target-hy bridizing sequence comprises the nucleotide sequence of residues 1-17 of SEQ ID NO: 11 and/or the second *Lactobacillus*-specific detection probe target-hybridizing sequence comprises the nucleotide sequence of residues 7-23 of SEQ ID NO: 12.

In certain embodiments of a method for diagnosing BV comprising the use of a first *Lactobacillus*-specific detection probe, a first A. vaginae-specific detection probe, and a first *G. vaginalis*-specific detection probe, each of the probes comprises a label. In some embodiments further comprising the use of a second *Lactobacillus*-specific detection probe, the second *Lactobacillus*-specific detection probe comprises a label. Particularly suitable labels include chemiluminescent and fluorescent labels.

In some embodiments of a method for diagnosing BV comprising the use of labeled detection probes as above, the detecting step (3) occurs during the amplifying step (2). In some such variations, each detection probe comprises a fluorescent label and a quencher. Particularly suitable detection probes comprising a fluorescent label and a quencher include a molecular torch, a molecular beacon, and a TaqMan detection probe.

In certain embodiments of a method for diagnosing BV comprising the use of detection probes as above, at least one of the first *Lactobacillus*-specific detection probe, the first A. vaginae-specific detection probe, and the first *G. vaginalis*-specific detection probe further comprises a non-target-hybridizing sequence. In some embodiments further comprising the use of a second *Lactobacillus*-specific detection probe, the second *Lactobacillus*-specific detection probe further comprises a non-target-hybridizing sequence. In some such variations, each of the first *Lactobacillus*-specific, first A. vaginae-specific detection probe, and first *G. vaginalis*-specific detection probes (or each of the first *Lactobacillus*-specific, second *Lactobacillus*-specific, first A. vaginae-specific, and first *G. vaginalis*-specific detection probes) is a molecular torch or a molecular beacon.

In some embodiments of a method for diagnosing BV as above, the method includes the detection of no more than ten bacterial genera associated with BV. For example, in certain variations, the method includes the detection of no more than five bacterial genera associated with BV. In a specific variation, the method does not include detection of bacterial genera associated with BV other than *Lactobacillus*, Atopobium, and *Gardnerella*.

In some embodiments of a method for diagnosing BV as above, if the presence of BV is indicated in the subject, then the method further includes administering a treatment regime for BV to the subject.

In some embodiments of a method for diagnosing BV as above, the method is a method for monitoring BV in the subject and the subject is undergoing a treatment regime for BV prior to step (a). In some such variations, if the presence of BV is indicated in the subject, then the method further includes either (i) administering the treatment regime for BV to the subject or (ii) administering a different treatment regime for BV to the subject.

In one aspect, the present invention provides a multiplex method for determining the presence or absence of each of *Lactobacillus* sp., *A. vaginae*. and *G. vaginalis* in a sample. The method generally includes the following steps:

(1) contacting a sample, the sample suspected of containing at least one of *Lactobacillus* sp., A. vaginae. and *G. vaginalis*, with (a) first, second, third, and fourth *Lactobacillus*-specific amplification oligomers for amplifying a target region of a *Lactobacillus* sp. target nucleic acid, where (i) the first *Lactobacillus*-specific amplification oligomer comprises a first *Lactobacillus*-specific target-hybridizing sequence substantially corresponding to the nucleotide sequence of residues 28-45 of SEQ ID NO: 10; (ii) the second *Lactobacillus*-specific amplification oligomer comprises a second *Lactobacillus*-specific target-hybridizing sequence substantially corresponding to the nucleotide sequence of SEQ ID NO:7; (iii) the third *Lactobacillus*-specific amplification oligomer comprises a third *Lactobacillus*-specific target-hybridizing sequence substantially corresponding to the nucleotide sequence of SEQ ID NO:8; and (iv) the fourth *Lactobacillus*-specific amplification oligomer comprises a fourth *Lactobacillus*-specific target-hybridizing sequence substantially corresponding to the nucleotide sequence of SEQ ID NO:9;

(b) first and second A. vaginae-specific amplification oligomers for amplifying a target region of a A. vaginae target nucleic acid, where (i) the first A. vaginae-specific amplification oligomer comprises a first A. vaginae-specific target-hybridizing sequence substantially corresponding to the nucleotide sequence of residues 28-45 of SEQ ID NO: 18 and (ii) the second A. vaginae-specific amplification oligomer comprises a second A. vaginae-specific target-hybridizing sequence substantially corresponding to the nucleotide sequence of SEQ ID NO: 17; and (c) first and second *G. vaginalis*-specific amplification oligomers for amplifying a target region of a *G. vaginalis* target nucleic acid, where (i) the first *G. vaginalis*-specific amplification oligomer comprises a first *G. vaginalis*-specific target-hybridizing sequence substantially corresponding to the nucleotide sequence of residues 36-52 of SEQ ID NO: 15 and (ii) the second *G. vaginalis*-specific amplification oligomer comprises a second *G. vaginalis*-specific target-hybridizing sequence substantially corresponding to the nucleotide sequence of SEQ ID NO:14;

(2) performing an in vitro nucleic acid amplification reaction, where any *Lactobacillus* sp., A. vaginae. and *G. vaginalis* target nucleic acid, if present in the sample, is used as a template for generating one or more amplification products corresponding to the *Lactobacillus* sp., A. vaginae. and *G. vaginalis* target regions; and (3) detecting the presence or absence of the one or more amplification products, thereby determining the presence or absence of *Lactobacillus* sp., A. vaginae. and *G. vaginalis* in the sample.

In some variations of a multiplex method as above, the first *Lactobacillus*-specific target-hybridizing sequence comprises the nucleotide sequence of residues 28-45 of SEQ ID NO: 10; the second *Lactobacillus*-specific target-hybridizing sequence comprises the nucleotide sequence of SEQ ID NO:7: the third *Lactobacillus*-specific target-hybridizing sequence comprises the nucleotide sequence of SEQ ID NO:8: the fourth *Lactobacillus*-specific target-hybridizing sequence comprises the nucleotide sequence of SEQ ID NO:9; the first A. vaginae-specific target-hybridizing sequence comprises the nucleotide sequence of residues 28-45 of SEQ ID NO: 18: the second A. vaginae-specific target-hybridizing sequence comprises the nucleotide sequence of SEQ ID NO: 17: the first *G. vaginalis*-specific target-hybridizing sequence comprises the nucleotide sequence of residues 36-52 of SEQ ID NO:15; and/or the second *G. vaginalis*-specific target-hybridizing sequence comprises the nucleotide sequence of SEQ ID NO: 14. In some such embodiments, the first *Lactobacillus*-specific target-hybridizing sequence consists of the nucleotide sequence of residues 28-45 of SEQ ID NO: 10: the second *Lactobacillus*-specific target-hybridizing sequence consists of the nucleotide sequence of SEQ ID NO:7: the third *Lactobacillus*-specific target-hybridizing sequence consists of the nucleotide sequence of SEQ ID NO:8: the fourth *Lactobacillus*-specific target-hybridizing sequence consists of the nucleotide sequence of SEQ ID NO:9; the first A. vaginae-specific target-hybridizing sequence consists of the nucleotide sequence of residues 28-45 of SEQ ID NO: 18: the second A. vaginae-specific target-hybridizing sequence consists of the nucleotide sequence of SEQ ID NO: 17: the first *G. vaginalis*-specific target-hybridizing sequence consists of the nucleotide sequence of residues 36-52 of SEQ ID NO: 15; and/or the second *G. vaginalis*-specific target-hybridizing sequence consists of the nucleotide sequence of SEQ ID NO:14.

In some embodiments of a multiplex method as above, at least one of the first *Lactobacillus*-specific amplification oligomer, the first A. vaginae-specific amplification oligomer, and the first *G. vaginalis*-specific amplification oligomer is a promoter primer or promoter provider further comprising a promoter sequence located 5' to the respective target hybridizing sequence. A particularly suitable promoter sequence is a T7 promoter sequence such as, for example, a promoter sequence having the nucleotide sequence of residues 1-27 of SEQ ID NO:10 (also shown as, e.g., residues 1-27 of SEQ ID NO: 18 or residues 9-35 of SEQ ID NO: 15). In specific variations, the first *Lactobacillus*-specific amplification oligomer comprises the nucleotide sequence of SEQ ID NO: 10: the first A. vaginae-specific amplification oligomer comprises the nucleotide sequence of SEQ ID NO: 18; and/or the first *G. vaginalis*-specific amplification oligomer comprises the nucleotide sequence of residues 9-52 of SEQ ID NO:15. In some embodiments, the first *G. vaginalis*-specific amplification oligomer comprises the nucleotide sequence of SEQ ID NO: 15.

In certain embodiments of a multiplex method as above, the method further includes purifying the *Lactobacillus* sp., A. vaginae, and *G. vaginalis* target nucleic acids, if present, from other components in the sample before step (2). In some such embodiments, the purifying step includes contacting the sample with at least one capture probe oligomer comprising a target-hybridizing sequence covalently attached to a sequence or moiety that binds to an immobilized probe. For example, the sample may be contacted with a first capture probe oligomer comprising a target-hybridizing sequence that specifically hybridizes to a target sequence within the *Lactobacillus* sp. target nucleic acid and a second capture probe target-hybridizing sequence comprising a target-hybridizing sequence that specifically hybridizes to a target sequence within each of the A. vaginae and *G. vaginalis* target nucleic acids, where each of the first and second capture probe target-hybridizing sequences is covalently attached to the sequence or moiety that binds to the immobilized probe: in some such embodiments, the first capture probe target-hybridizing sequence specifically hybridizes to a target sequence within each of L. crispatus, L. jensenii, and L. gasseri target nucleic acid. In specific variations comprising first and second target capture probes as above, the first capture probe target-hybridizing sequence substantially corresponds to the nucleotide sequence of residues 1-19 of SEQ ID NO:6 and/or the second capture probe target-hybridizing sequence substantially corresponds to the nucleotide sequence of residues 1-20 of SEQ ID NO:13. In some embodiments, the first capture probe oligomer comprises the nucleotide sequence of SEQ ID NO:6 and/or the second capture probe oligomer comprises the nucleotide sequence of SEQ ID NO: 13.

In some embodiments of a multiplex method as above, the detecting step (3) comprises (i) contacting the one or more amplification products with a first *Lactobacillus*-specific detection probe comprising a target-hybridizing sequence that specifically hybridizes to the *Lactobacillus* sp. target region, a first A. vaginae-specific detection probe comprising a target-hybridizing sequence that specifically hybridizes to the A. vaginae target region, and a first *G. vaginalis*-specific detection probe comprising a target-hybridizing sequence that specifically hybridizes to the *G. vaginalis* target region, and (ii) detecting the presence or absence of any target-hybridized *Lactobacillus*-specific, A. vaginae-specific, and/or *G. vaginalis*-specific detection probe. In some embodiments, the first A. vaginae-specific detection probe target-hybridizing sequence substantially corresponds to the nucleotide sequence of residues 6-21 of SEQ ID NO: 19 and/or the first *G. vaginalis*-specific detection probe target-hybridizing sequence substantially corresponds to the nucleotide sequence of residues 1-18 of SEQ ID NO: 16: in more specific variations, the first A. vaginae-specific detection probe target-hybridizing sequence comprises the nucleotide sequence of residues 6-21 of SEQ ID NO:19 and/or the first *G. vaginalis*-specific detection probe target-hybridizing sequence comprises the nucleotide sequence of residues 1-18 of SEQ ID NO:16. In some embodiments, the first *Lactobacillus*-specific detection probe target-hybridizing sequence specifically hybridizes to a target region of each of L. crispatus and L. *jensenii* target nucleic acid and the method further includes contacting the one or more amplification products with a second *Lactobacillus*-specific detection probe comprising a target-hybridizing sequence that specifically hybridizes to a target region of L. gasseri target nucleic acid: in some such embodiments, the first *Lactobacillus*-specific detection probe target-hybridizing sequence substantially corresponds to the nucleotide sequence of residues 1-17 of SEQ ID NO:11 and/or the second *Lactobacillus*-specific detection probe target-hybridizing sequence substantially corresponds to the nucleotide sequence of residues 7-23 of SEQ ID NO: 12: in more specific variations, the first *Lactobacillus*-specific detection probe target-hybridizing sequence comprises the nucleotide sequence of residues 1-17 of SEQ ID NO: 11 and/or the second *Lactobacillus*-specific detection probe target-hybridizing sequence comprises the nucleotide sequence of residues 7-23 of SEQ ID NO: 12.

In certain embodiments of a multiplex method comprising the use of a first *Lactobacillus*-specific detection probe, a first A. vaginae-specific detection probe, and a first *G. vaginalis*-specific detection probe, each of the probes comprises a label. In some embodiments further comprising the use of a second *Lactobacillus*-specific detection probe, the second *Lactobacillus*-specific detection probe comprises a label. Particularly suitable labels include chemiluminescent and fluorescent labels.

In some embodiments of a multiplex method comprising the use of labeled detection probes as above, the detecting step (3) occurs during the amplifying step (2). In some such variations, each detection probe comprises a fluorescent label and a quencher. Particularly suitable detection probes comprising a fluorescent label and a quencher include a molecular torch, a molecular beacon, and a TaqMan detection probe.

In certain embodiments of a multiplex method comprising the use of detection probes as above, at least one of the first *Lactobacillus*-specific detection probe, the first A. vaginae-specific detection probe, and the first *G. vaginalis*-specific detection probe further comprises a non-target-hybridizing sequence. In some embodiments further comprising the use of a second *Lactobacillus*-specific detection probe, the second *Lactobacillus*-specific detection probe further comprises a non-target-hybridizing sequence. In some such variations, each of the first *Lactobacillus*-specific, first A. vaginae-specific detection probe, and first *G. vaginalis*-specific detection probes (or each of the first *Lactobacillus*-specific, second *Lactobacillus*-specific, first A. vaginae-specific, and first *G. vaginalis*-specific detection probes) is a molecular torch or a molecular beacon.

In some embodiments of a multiplex method as above, the amplification reaction at step (2) is an isothermal amplification reaction. In particular variations, the isothermal amplification reaction is a transcription-mediated amplification (TMA) reaction. In certain embodiments, the isothermal amplification reaction is a real-time amplification reaction.

In another aspect, the present invention provides a composition or a kit for determining the presence or absence of each of *Lactobacillus* sp., A. vaginae. and *G. vaginalis* in a sample. The composition or kit generally includes the following oligomers (a) first, second, third, and fourth *Lactobacillus*-specific amplification oligomers for amplifying a target region of a *Lactobacillus* sp. target nucleic acid, where (i) the first *Lactobacillus*-specific amplification oligomer comprises a first *Lactobacillus*-specific target-hybridizing sequence substantially corresponding to the nucleotide sequence of residues 28-45 of SEQ ID NO:10; (ii) the second *Lactobacillus*-specific amplification oligomer comprises a second *Lactobacillus*-specific target-hybridizing sequence substantially corresponding to the nucleotide sequence of SEQ ID NO:7: (iii) the third *Lactobacillus*-specific amplification oligomer comprises a third *Lactobacillus*-specific target-hybridizing sequence substantially corresponding to the nucleotide sequence of SEQ ID NO:8; and (iv) the fourth *Lactobacillus*-specific amplification oligomer comprises a fourth *Lactobacillus*-specific target-hybridizing sequence substantially corresponding to the nucleotide sequence of SEQ ID NO:9:

(b) first and second A. vaginae-specific amplification oligomers for amplifying a target region of a A. vaginae target nucleic acid, where (i) the first A. vaginae-specific amplification oligomer comprises a first A. vaginae-specific target-hybridizing sequence substantially corresponding to the nucleotide sequence of residues 28-45 of SEQ ID NO: 18 and (ii) the second A. vaginae-specific amplification oligomer comprises a second A. vaginae-specific target-hybridizing sequence substantially corresponding to the nucleotide sequence of SEQ ID NO: 17; and (c) first and second G. vaginalis-specific amplification oligomers for amplifying a target region of a G. vaginalis target nucleic acid, where (i) the first G. vaginalis-specific amplification oligomer comprises a first G. vaginalis-specific target-hybridizing sequence substantially corresponding to the nucleotide sequence of residues 36-52 of SEQ ID NO:15 and (ii) the second G. vaginalis-specific amplification oligomer comprises a second G. vaginalis-specific target-hybridizing sequence substantially corresponding to the nucleotide sequence of SEQ ID NO: 14.

In some variations of a composition or kit as above, the first Lactobacillus-specific target-hybridizing sequence comprises the nucleotide sequence of residues 28-45 of SEQ ID NO:10; the second Lactobacillus-specific target-hybridizing sequence comprises the nucleotide sequence of SEQ ID NO:7: the third Lactobacillus-specific target-hybridizing sequence comprises the nucleotide sequence of SEQ ID NO:8: the fourth Lactobacillus-specific target-hybridizing sequence comprises the nucleotide sequence of SEQ ID NO:9; the first A. vaginae-specific target-hybridizing sequence comprises the nucleotide sequence of residues 28-45 of SEQ ID NO: 18: the second A. vaginae-specific target-hybridizing sequence comprises the nucleotide sequence of SEQ ID NO:17: the first G. vaginalis-specific target-hybridizing sequence comprises the nucleotide sequence of residues 36-52 of SEQ ID NO:15; and/or the second G. vaginalis-specific target-hybridizing sequence comprises the nucleotide sequence of SEQ ID NO:14. In some such embodiments, the first Lactobacillus-specific target-hybridizing sequence consists of the nucleotide sequence of residues 28-45 of SEQ ID NO: 10: the second Lactobacillus-specific target-hybridizing sequence consists of the nucleotide sequence of SEQ ID NO:7: the third Lactobacillus-specific target-hy bridizing sequence consists of the nucleotide sequence of SEQ ID NO:8: the fourth Lactobacillus-specific target-hybridizing sequence consists of the nucleotide sequence of SEQ ID NO:9; the first A. vaginae-specific target-hybridizing sequence consists of the nucleotide sequence of residues 28-45 of SEQ ID NO: 18: the second A. vaginae-specific target-hybridizing sequence consists of the nucleotide sequence of SEQ ID NO: 17: the first G. vaginalis-specific target-hybridizing sequence consists of the nucleotide sequence of residues 36-52 of SEQ ID NO: 15; and/or the second G. vaginalis-specific target-hybridizing sequence consists of the nucleotide sequence of SEQ ID NO: 14.

In some embodiments of a composition or kit as above, at least one of the first Lactobacillus-specific amplification oligomer, the first A. vaginae-specific amplification oligomer, and the first G. vaginalis-specific amplification oligomer is a promoter primer or promoter provider further comprising a promoter sequence located 5' to the respective target hybridizing sequence. A particularly suitable promoter sequence is a T7 promoter sequence such as, for example, a promoter sequence having the nucleotide sequence of residues 1-27 of SEQ ID NO:10 (also shown as, e.g., residues 1-27 of SEQ ID NO:18 or residues 9-35 of SEQ ID NO: 15). In specific variations, the first Lactobacillus-specific amplification oligomer comprises the nucleotide sequence of SEQ ID NO: 10: the first A. vaginae-specific amplification oligomer comprises the nucleotide sequence of SEQ ID NO:18; and/or the first G. vaginalis-specific amplification oligomer comprises the nucleotide sequence of residues 9-52 of SEQ ID NO: 15. In some embodiments, the first G. vaginalis-specific amplification oligomer comprises the nucleotide sequence of SEQ ID NO: 15.

In certain embodiments of a composition or a kit as above, the composition or kit further includes at least one capture probe oligomer comprising a target-hybridizing sequence covalently attached to a sequence or moiety that binds to an immobilized probe. For example, the composition or kit may include a first capture probe oligomer comprising a target-hybridizing sequence that specifically hybridizes to a target sequence within the Lactobacillus sp. target nucleic acid and a second capture probe target-hybridizing sequence comprising a target-hybridizing sequence that specifically hybridizes to a target sequence within each of the A. vaginae and G. vaginalis target nucleic acids, where each of the first and second capture probe target-hybridizing sequences is covalently attached to the sequence or moiety that binds to the immobilized probe: in some such embodiments, the first capture probe target-hybridizing sequence specifically hybridizes to a target sequence within each of L. crispatus, L. jensenii, and L. gasseri target nucleic acid. In specific variations comprising first and second target capture probes as above, the first capture probe target-hybridizing sequence substantially corresponds to the nucleotide sequence of residues 1-19 of SEQ ID NO: 6 and/or the second capture probe target-hybridizing sequence substantially corresponds to the nucleotide sequence of residues 1-20 of SEQ ID NO:13. In some embodiments, the first capture probe oligomer comprises the nucleotide sequence of SEQ ID NO:6 and/or the second capture probe oligomer comprises the nucleotide sequence of SEQ ID NO:13.

In some embodiments of a composition or kit as above, the composition or kit further includes a first Lactobacillus-specific detection probe comprising a target-hybridizing sequence that specifically hybridizes to the Lactobacillus sp. target region, a first A. vaginae-specific detection probe comprising a target-hybridizing sequence that specifically hybridizes to the A. vaginae target region, and a first G. vaginalis-specific detection probe comprising a target-hybridizing sequence that specifically hybridizes to the G. vaginalis target region. In some embodiments, the first A. vaginae-specific detection probe target-hybridizing sequence substantially corresponds to the nucleotide sequence of residues 6-21 of SEQ ID NO:19 and/or the first G. vaginalis-specific detection probe target-hybridizing sequence substantially corresponds to the nucleotide sequence of residues 1-18 of SEQ ID NO: 16: in more specific variations, the first A. vaginae-specific detection probe target-hybridizing sequence comprises the nucleotide sequence of residues 6-21 of SEQ ID NO: 19 and/or the first G. vaginalis-specific detection probe target-hybridizing sequence comprises the nucleotide sequence of residues 1-18 of SEQ ID NO: 16. In some embodiments, the first Lactobacillus-specific detection probe target-hybridizing sequence specifically hybridizes to a target region of each of L. crispatus and L. jensenii target nucleic acid and the composition or kit further includes a second Lactobacillus-specific detection probe comprising a target-hybridizing sequence that specifically hybridizes to a target region of L. gasseri target nucleic acid: in some such embodiments, the first *Lactobacillus*-specific detection probe target-hybridizing sequence substantially corresponds to the nucleotide sequence of residues 1-17 of SEQ ID NO: 11 and/or the second *Lactobacillus*-specific detection probe target-hybridizing sequence substantially corresponds to the nucleotide sequence of residues 7-23 of SEQ ID NO: 12: in more specific variations, the first *Lactobacillus*-specific detection probe target-hybridizing sequence comprises the nucleotide sequence of residues 1-17 of SEQ ID NO: 11 and/or the second *Lactobacillus*-specific detection probe target-hybridizing sequence comprises the nucleotide sequence of residues 7-23 of SEQ ID NO: 12.

In certain embodiments of a composition or kit comprising a first *Lactobacillus*-specific detection probe, a first A. vaginae-specific detection probe, and a first *G. vaginalis*-specific detection probe, each of the probes comprises a label. In some embodiments further comprising a second *Lactobacillus*-specific detection probe, the second *Lactobacillus*-specific detection probe comprises a label. Particularly suitable labels include chemiluminescent and fluorescent labels. In some variations, each detection probe comprises a fluorescent label and a quencher: particularly suitable detection probes comprising a fluorescent label and a quencher include a molecular torch, a molecular beacon, and a TaqMan detection probe.

In certain embodiments of a composition or kit comprising detection probes as above, at least one of the first *Lactobacillus*-specific detection probe, the first A. vaginae-specific detection probe, and the first *G. vaginalis*-specific detection probe further comprises a non-target-hybridizing sequence. In some embodiments further comprising a second *Lactobacillus*-specific detection probe, the second *Lactobacillus*-specific detection probe further comprises a non-target-hybridizing sequence. In some such variations, each of the first *Lactobacillus*-specific, first A. vaginae-specific detection probe, and first *G. vaginalis*-specific detection probes (or each of the first *Lactobacillus*-specific, second *Lactobacillus*-specific, first A. vaginae-specific, and first *G. vaginalis*-specific detection probes) is a molecular torch or a molecular beacon.

In yet another aspect, the present invention provides a method for determining the presence or absence of *Lactobacillus* sp. in a sample. The method generally includes the following steps:

(1) contacting a sample, the sample suspected of containing *Lactobacillus* sp., with first, second, third, and fourth amplification oligomers for amplifying a target region of a *Lactobacillus* sp. target nucleic acid, where (i) the first amplification oligomer comprises a first target-hybridizing sequence substantially corresponding to the nucleotide sequence of residues 28-45 of SEQ ID NO:10; (ii) the amplification oligomer comprises a second target-hybridizing sequence substantially corresponding to the nucleotide sequence of SEQ ID NO:7: (iii) the third amplification oligomer comprises a third target-hybridizing sequence substantially corresponding to the nucleotide sequence of SEQ ID NO:8; and (iv) the fourth amplification oligomer comprises a fourth target-hybridizing sequence substantially corresponding to the nucleotide sequence of SEQ ID NO:9:

(2) performing an in vitro nucleic acid amplification reaction, where any *Lactobacillus* sp. target nucleic acid, if present in the sample, is used as a template for generating one or more amplification products corresponding to the *Lactobacillus* sp. target region; and (3) detecting the presence or absence of the one or more amplification products, thereby determining the presence or absence of *Lactobacillus* sp. in the sample.

In some variations of a method for detecting *Lactobacillus* sp. as above, the first *Lactobacillus*-specific target-hybridizing sequence comprises the nucleotide sequence of residues 28-45 of SEQ ID NO: 10; the second *Lactobacillus*-specific target-hy bridizing sequence comprises the nucleotide sequence of SEQ ID NO:7: the third *Lactobacillus*-specific target-hybridizing sequence comprises the nucleotide sequence of SEQ ID NO:8; and/or the fourth target-hybridizing sequence comprises the nucleotide sequence of SEQ ID NO: 9. In some such embodiments, the first target-hybridizing sequence consists of the nucleotide sequence of residues 28-45 of SEQ ID NO: 10: the second target-hybridizing sequence consists of the nucleotide sequence of SEQ ID NO: 7; the third target-hy bridizing sequence consists of the nucleotide sequence of SEQ ID NO:8; and/or the fourth target-hybridizing sequence consists of the nucleotide sequence of SEQ ID NO:9.

In some embodiments of a method for detecting *Lactobacillus* sp. as above, the first amplification oligomer is a promoter primer or promoter provider further comprising a promoter sequence located 5' to the respective target hybridizing sequence. A particularly suitable promoter sequence is a T7 promoter sequence such as, for example, a promoter sequence having the nucleotide sequence of residues 1-27 of SEQ ID NO: 10. In a specific variation, the first amplification oligomer comprises the nucleotide sequence of SEQ ID NO: 10.

In certain embodiments of a method for detecting *Lactobacillus* sp. as above, the method further includes purifying the *Lactobacillus* sp. target nucleic acid, if present, from other components in the sample before step (2). In some such embodiments, the purifying step includes contacting the sample with at least one capture probe oligomer comprising a target-hybridizing sequence covalently attached to a sequence or moiety that binds to an immobilized probe, where the capture probe target-hybridizing sequence specifically hybridizes to a target sequence within the *Lactobacillus* sp. target nucleic acid. In some embodiments, the capture probe target-hybridizing sequence specifically hybridizes to a target sequence within each of L. crispatus, L. jensenii, and L. gasseri target nucleic acid: in some such variations, the first capture probe target-hybridizing sequence substantially corresponds to the nucleotide sequence of residues 1-19 of SEQ ID NO:6: in more specific embodiments, the capture probe oligomer comprises the nucleotide sequence of SEQ ID NO: 6.

In some embodiments of a method for detecting *Lactobacillus* sp. as above, the detecting step (3) includes (i) contacting the one or more amplification products with a first detection probe comprising a target-hybridizing sequence that specifically hy bridizes to the *Lactobacillus* sp. target region, and detecting the presence or absence of any target-hybridized detection probe. In some embodiments, the first detection probe target-hybridizing sequence specifically hybridizes to a target region of each of L. crispatus and L. jensenii target nucleic acid and the method further includes contacting the one or more amplification products with a second detection probe comprising a target-hybridizing sequence that specifically hybridizes to a target region of L. gasseri target nucleic acid: in some such embodiments, the first detection probe target-hybridizing sequence substantially corresponds to the nucleotide sequence of residues 1-17 of SEQ ID NO: 11 and/or the second detection probe target-hybridizing sequence substantially corresponds to the nucleotide sequence of residues 7-23 of SEQ ID NO: 12: in more specific variations, the first detection probe target-hybridizing sequence comprises the nucleotide sequence of residues 1-17 of SEQ ID NO: 11 and/or the second detection probe target-hybridizing sequence comprises the nucleotide sequence of residues 7-23 of SEQ ID NO: 12.

In certain embodiments of a method for detecting *Lactobacillus* sp. as above, where the method includes the use of a first detection probe, the first detection probe comprises a label. In some embodiments further including contacting the one or more amplification oligomers with a second detection probe, the second detection probe comprises a label. Particularly suitable labels include chemiluminescent and fluorescent labels.

In some embodiments of a method for detecting *Lactobacillus* sp. and comprising the use of labeled detection probe(s) as above, the detecting step (3) occurs during the amplifying step (2). In some such variations, each detection probe comprises a fluorescent label and a quencher. Particularly suitable detection probes comprising a fluorescent label and a quencher include a molecular torch, a molecular beacon, and a TaqMan detection probe.

In certain embodiments of a method for detecting *Lactobacillus* sp. and comprising the use of detection probe(s) as above, the first detection probe further comprises a non-target-hybridizing sequence. In some embodiments further comprising the use of a second detection probe, the second detection probe further comprises a non-target-hybridizing sequence. In some such variations, the first detection probe (or each of the first and second detection probes) is a molecular torch or a molecular beacon.

In yet another aspect, the present invention provides a method for determining the presence or absence of A. vaginae in a sample. The method generally includes the following steps:
  (1) contacting a sample, the sample suspected of containing A. vaginae, with first and second amplification oligomers for amplifying a target region of a A. vaginae target nucleic acid, where (i) the first amplification oligomer comprises a first target-hybridizing sequence substantially corresponding to the nucleotide sequence of residues 28-45 of SEQ ID NO:18 and (ii) the second amplification oligomer comprises a second target-hybridizing sequence substantially corresponding to the nucleotide sequence of SEQ ID NO: 17;
  (2) performing an in vitro nucleic acid amplification reaction, where any A. vaginae target nucleic acid, if present in the sample, is used as a template for generating one or more amplification products corresponding to the A. vaginae target region; and
  (3) detecting the presence or absence of the one or more amplification products, thereby determining the presence or absence of A. vaginae in the sample.

In some variations of a method for detecting A. vaginae as above, the first target-hybridizing sequence comprises the nucleotide sequence of residues 28-45 of SEQ ID NO: 18 and/or the second target-hybridizing sequence comprises the nucleotide sequence of SEQ ID NO:17. In some such embodiments, the first target-hybridizing sequence consists of the nucleotide sequence of residues 28-45 of SEQ ID NO: 18 and/or the second target-hybridizing sequence consists of the nucleotide sequence of SEQ ID NO:17.

In some embodiments of a method for detecting A. vaginae as above, the first amplification oligomer is a promoter primer or promoter provider further comprising a promoter sequence located 5' to the respective target hybridizing sequence. A particularly suitable promoter sequence is a T7 promoter sequence such as, for example, a promoter sequence having the nucleotide sequence of residues 1-27 of SEQ ID NO: 18. In a specific variation, the first amplification oligomer comprises the nucleotide sequence of SEQ ID NO: 18.

In certain embodiments of a method for detecting A. vaginae as above, the method further includes purifying the A. vaginae target nucleic acid, if present, from other components in the sample before step (2). In some such embodiments, the purifying step comprises contacting the sample with at least one capture probe oligomer comprising a target-hybridizing sequence covalently attached to a sequence or moiety that binds to an immobilized probe, where the capture probe target-hybridizing sequence specifically hybridizes to a target sequence within the A. vaginae target nucleic acid. In some embodiments, the capture probe target-hybridizing sequence substantially corresponds to the nucleotide sequence of residues 1-20 of SEQ ID NO: 13. In more specific variations, the capture probe oligomer comprises the nucleotide sequence of SEQ ID NO: 13.

In some embodiments of a method for detecting A. vaginae as above, the detecting step (3) includes contacting the one or more amplification products with a detection probe comprising a target-hybridizing sequence that specifically hybridizes to the A. vaginae target region, and detecting the presence or absence of any target-hybridized detection probe. In some embodiments, the detection probe target-hybridizing sequence substantially corresponds to the nucleotide sequence of residues 6-21 of SEQ ID NO:19. In more specific variations, the detection probe target-hybridizing sequence comprises the nucleotide sequence of residues 6-21 of SEQ ID NO: 19.

In certain embodiments of a method for detecting A. vaginae as above, where the method includes the use of a detection probe, the detection probe comprises a label. Particularly suitable labels include fluorescent and chemiluminescent labels.

In some embodiments of a method for detecting A. vaginae as above and comprising the use of a labeled detection probe as above, the detecting step (3) occurs during the amplifying step (2). In some such variations, the detection probe comprises a fluorescent label and a quencher. Particularly suitable detection probes comprising a fluorescent label and a quencher include a molecular torch, a molecular beacon, and a TaqMan detection probe.

In certain embodiments of a method for detecting A. vaginae and comprising the use of a detection probe as above, the detection probe further comprises a non-target-hybridizing sequence. In some such variations, the detection probe is a molecular torch or a molecular beacon.

In still another aspect, the present invention provides a method for determining the presence or absence of G. vaginalis in a sample. The method generally includes the following steps:
  (1) contacting a sample, the sample suspected of containing G. vaginalis first and second amplification oligomers for amplifying a target region of a G. vaginalis target nucleic acid, wherein (i) the first amplification oligomer comprises a first target-hybridizing sequence substantially corresponding to the nucleotide sequence of residues 36-52 of SEQ ID NO: 15 and (ii) the second amplification oligomer comprises a second target-hybridizing sequence substantially corresponding to the nucleotide sequence of SEQ ID NO:14:

(2) performing an in vitro nucleic acid amplification reaction, wherein any *G. vaginalis* target nucleic acid, if present in the sample, is used as a template for generating one or more amplification products corresponding to the *G. vaginalis* target region; and (3) detecting the presence or absence of the one or more amplification products, thereby determining the presence or absence of *G. vaginalis* in the sample.

In some variations of a method for detecting *G. vaginalis* as above, the first target-hybridizing sequence comprises the nucleotide sequence of residues 36-52 of SEQ ID NO: 15 and/or the second target-hybridizing sequence comprises the nucleotide sequence of SEQ ID NO:14. In some such embodiments, the first target-hybridizing sequence consists of the nucleotide sequence of residues 36-52 of SEQ ID NO:15 and/or the second target-hybridizing sequence consists of the nucleotide sequence of SEQ ID NO: 14.

In some embodiments of a method for detecting *G. vaginalis* as above, the first amplification oligomer is a promoter primer or promoter provider further comprising a promoter sequence located 5' to the respective target hybridizing sequence. A particularly suitable promoter sequence is a T7 promoter sequence such as, for example, a promoter sequence having the nucleotide sequence of residues 9-36 of SEQ ID NO:15. In specific variations, the first amplification oligomer comprises the nucleotide sequence of 9-52 of SEQ ID NO: 15: in some such embodiments, the first amplification oligomer comprises the nucleotide sequence of SEQ ID NO: 15.

In certain embodiments of a method for detecting *G. vaginalis* as above, the method further includes purifying the *G. vaginalis* target nucleic acid, if present, from other components in the sample before step (2). In some such embodiments, the purifying step comprises contacting the sample with at least one capture probe oligomer comprising a target-hybridizing sequence covalently attached to a sequence or moiety that binds to an immobilized probe, where the capture probe target-hybridizing sequence specifically hybridizes to a target sequence within the *G. vaginalis* target nucleic acid. In some embodiments, the capture probe target-hybridizing sequence substantially corresponds to the nucleotide sequence of residues 1-20 of SEQ ID NO: 13. In more specific variations, the capture probe oligomer comprises the nucleotide sequence of SEQ ID NO: 13.

In some embodiments of a method for detecting *G. vaginalis* as above, the detecting step (3) includes contacting the one or more amplification products with a detection probe comprising a target-hybridizing sequence that specifically hybridizes to the *G. vaginalis* target region, and detecting the presence or absence of any target-hybridized detection probe. In some embodiments, the detection probe target-hybridizing sequence substantially corresponds to the nucleotide sequence of residues 1-18 of SEQ ID NO:16. In more specific variations, the detection probe target-hybridizing sequence comprises the nucleotide sequence of residues 1-18 of SEQ ID NO:16.

In certain embodiments of a method for detecting *G. vaginalis* as above, where the method includes the use of a detection probe, the detection probe comprises a label. Particularly suitable labels include fluorescent and chemiluminescent labels.

In some embodiments of a method for detecting *G. vaginalis* as above and comprising the use of a labeled detection probe as above, the detecting step (3) occurs during the amplifying step (2). In some such variations, the detection probe comprises a fluorescent label and a quencher. Particularly suitable detection probes comprising a fluorescent label and a quencher include a molecular torch, a molecular beacon, and a TaqMan detection probe.

In certain embodiments of a method for detecting *G. vaginalis* and comprising the use of a detection probe as above, the detection probe further comprises a non-target-hybridizing sequence. In some such variations, the detection probe is a molecular torch or a molecular beacon.

In some embodiments of a method for detecting *Lactobacillus* sp., *A. vaginae*, or *G. vaginalis* as above, the amplification reaction at step (2) is an isothermal amplification reaction. In particular variations, the isothermal amplification reaction is a transcription-mediated amplification (TMA) reaction. In certain embodiments, the isothermal amplification reaction is a real-time amplification reaction.

These and other aspects of the invention will become evident upon reference to the following detailed description of the invention. Additional disclosed embodiments are as follows.

Embodiment 1 is a multiplex method for determining the presence or absence of each of *Lactobacillus* sp., *A. vaginae*. and *G. vaginalis* in a sample, the method comprising:

(1) contacting a sample, said sample suspected of containing at least one of *Lactobacillus* sp., *A. vaginae*. and *G. vaginalis*, with (a) first, second, third, and fourth *Lactobacillus*-specific amplification oligomers for amplifying a target region of a *Lactobacillus* sp. target nucleic acid, wherein (i) the first *Lactobacillus*-specific amplification oligomer comprises a first *Lactobacillus*-specific target-hybridizing sequence substantially corresponding to the nucleotide sequence of residues 28-45 of SEQ ID NO:10; (ii) the second *Lactobacillus*-specific amplification oligomer comprises a second *Lactobacillus*-specific target-hybridizing sequence substantially corresponding to the nucleotide sequence of SEQ ID NO:7: (iii) the third *Lactobacillus*-specific amplification oligomer comprises a third *Lactobacillus*-specific target-hybridizing sequence substantially corresponding to the nucleotide sequence of SEQ ID NO:8; and (iv) the fourth *Lactobacillus*-specific amplification oligomer comprises a fourth *Lactobacillus*-specific target-hybridizing sequence substantially corresponding to the nucleotide sequence of SEQ ID NO:9:

(b) first and second *A. vaginae*-specific amplification oligomers for amplifying a target region of a *A. vaginae* target nucleic acid, wherein (i) the first *A. vaginae*-specific amplification oligomer comprises a first *A. vaginae*-specific target-hybridizing sequence substantially corresponding to the nucleotide sequence of residues 28-45 of SEQ ID NO: 18 and (ii) the second *A. vaginae*-specific amplification oligomer comprises a second *A. vaginae*-specific target-hybridizing sequence substantially corresponding to the nucleotide sequence of SEQ ID NO: 17; and (c) first and second *G. vaginalis*-specific amplification oligomers for amplifying a target region of a *G. vaginalis* target nucleic acid, wherein (i) the first *G. vaginalis*-specific amplification oligomer comprises a first *G. vaginalis*-specific target-hybridizing sequence substantially corresponding to the nucleotide sequence of residues 36-52 of SEQ ID NO:15 and (ii) the second *G. vaginalis*-specific amplification oligomer comprises a second *G. vaginalis*-specific target-hybridizing sequence substantially corresponding to the nucleotide sequence of SEQ ID NO:14:
(2) performing an in vitro nucleic acid amplification reaction, wherein any *Lactobacillus* sp., A. vaginae. and *G. vaginalis* target nucleic acid, if present in the sample, is used as a template for generating one or more amplification products corresponding to the *Lactobacillus* sp., A. vaginae. and *G. vaginalis* target regions; and
(3) detecting the presence or absence of the one or more amplification products, thereby determining the presence or absence of *Lactobacillus* sp., A. vaginae. and *G. vaginalis* in the sample.

Embodiment 2 is the method of embodiment 1, wherein
(1) the first *Lactobacillus*-specific target-hybridizing sequence comprises the nucleotide sequence of residues 28-45 of SEQ ID NO:10;
(2) the second *Lactobacillus*-specific target-hybridizing sequence comprises the nucleotide sequence of SEQ ID NO:7:
(3) the third *Lactobacillus*-specific target-hybridizing sequence comprises the nucleotide sequence of SEQ ID NO:8;
(4) the fourth *Lactobacillus*-specific target-hybridizing sequence comprises the nucleotide sequence of SEQ ID NO:9;
(5) the first A. vaginae-specific target-hybridizing sequence comprises the nucleotide sequence of residues 28-45 of SEQ ID NO: 18;
(6) the second A. vaginae-specific target-hybridizing sequence comprises the nucleotide sequence of SEQ ID NO: 17;
(7) the first *G. vaginalis*-specific target-hybridizing sequence comprises the nucleotide sequence of residues 36-52 of SEQ ID NO: 15; and/or
(8) the second *G. vaginalis*-specific target-hybridizing sequence comprises the nucleotide sequence of SEQ ID NO: 14.

Embodiment 3 is the method of embodiment 1 or 2, wherein
(1) the first *Lactobacillus*-specific target-hybridizing sequence consists of the nucleotide sequence of residues 28-45 of SEQ ID NO:10;
(2) the second *Lactobacillus*-specific target-hybridizing sequence consists of the nucleotide sequence of SEQ ID NO:7:
(3) the third *Lactobacillus*-specific target-hybridizing sequence consists of the nucleotide sequence of SEQ ID NO:8:
(4) the fourth *Lactobacillus*-specific target-hybridizing sequence consists of the nucleotide sequence of SEQ ID NO:9:
(5) the first A. vaginae-specific target-hybridizing sequence consists of the nucleotide sequence of residues 28-45 of SEQ ID NO:18;
(6) the second A. vaginae-specific target-hybridizing sequence consists of the nucleotide sequence of SEQ ID NO: 17;
(7) the first *G. vaginalis*-specific target-hybridizing sequence consists of the nucleotide sequence of residues 36-52 of SEQ ID NO:15; and/or
(8) the second *G. vaginalis*-specific target-hybridizing sequence consists of the nucleotide sequence of SEQ ID NO: 14.

Embodiment 4 is the method of any one of embodiments 1 to 3, wherein at least one of the first *Lactobacillus*-specific amplification oligomer, the first A. vaginae-specific amplification oligomer, and the first *G. vaginalis*-specific amplification oligomer is a promoter primer or promoter provider further comprising a promoter sequence located 5' to the respective target hybridizing sequence.

Embodiment 5 is the method of embodiment 4, wherein the promoter sequence is a T7 promoter sequence.

Embodiment 6 is the method of embodiment 5, wherein the promoter sequence has the nucleotide sequence of residues 1-27 of SEQ ID NO: 10.

Embodiment 7 is the method of embodiment 4, wherein
the first *Lactobacillus*-specific amplification oligomer comprises the nucleotide sequence of SEQ ID NO:10;
the first A. vaginae-specific amplification oligomer comprises the nucleotide sequence of SEQ ID NO: 18; and/or
the first *G. vaginalis*-specific amplification oligomer comprises the nucleotide sequence of residues 9-52 of SEQ ID NO: 15.

Embodiment 8 is the method of embodiment 7, wherein the first *G. vaginalis*-specific amplification oligomer comprises the nucleotide sequence of SEQ ID NO: 15.

Embodiment 9 is the method of any one of embodiments 1 to 8, further comprising purifying the *Lactobacillus* sp., A. vaginae, and *G. vaginalis* target nucleic acids, if present, from other components in the sample before step (2).

Embodiment 10 is the method of embodiment 9, wherein the purifying step comprises contacting the sample with at least one capture probe oligomer comprising a target-hybridizing sequence covalently attached to a sequence or moiety that binds to an immobilized probe.

Embodiment 11 is the method of embodiment 10, wherein the sample is contacted with first and second capture probe oligomers,
wherein the first capture probe oligomer comprises a target-hybridizing sequence that specifically hybridizes to a target sequence within the *Lactobacillus* sp. target nucleic acid and the second capture probe target-hybridizing sequence comprises a target-hybridizing sequence that specifically hybridizes to a target sequence within each of the A. vaginae and *G. vaginalis* target nucleic acids, and wherein each of the first and second capture probe target-hybridizing sequences is covalently attached to the sequence or moiety that binds to the immobilized probe.

Embodiment 12 is the method of embodiment 11, wherein the first capture probe target-hybridizing sequence specifically hybridizes to a target sequence within each of L. crispatus, L. *jensenii*, and L. gasseri target nucleic acid.

Embodiment 13 is the method of embodiment 12, wherein the first capture probe target-hybridizing sequence substantially corresponds to the nucleotide sequence of residues 1-19 of SEQ ID NO:6.

Embodiment 14 is the method of embodiment 12 or 13, wherein the second capture probe target-hybridizing sequence substantially corresponds to the nucleotide sequence of residues 1-20 of SEQ ID NO:13.

Embodiment 15 is the method of embodiment 14, wherein
the first capture probe oligomer comprises the nucleotide sequence of SEQ ID NO:6, and/or
the second capture probe oligomer comprises the nucleotide sequence of SEQ ID NO: 13.

Embodiment 16 is the method of any one of embodiments 1 to 15, wherein the detecting step (3) comprises contacting the one or more amplification products with a first *Lactobacillus*-specific detection probe comprising a target-hybridizing sequence that specifically hybridizes to the *Lactobacillus* sp. target region, a first A. vaginae-specific detection probe comprising a target-hybridizing sequence that specifically hybridizes to the A. vaginae target region, and a first *G. vaginalis*-specific detection probe comprising a target-hybridizing sequence that specifically hybridizes to the *G. vaginalis* target region, and detecting the presence or absence of any target-hybridized *Lactobacillus*-specific, A. vaginae-specific, and/or *G. vaginalis*-specific detection probe.

Embodiment 17 is the method of embodiment 16, wherein the first A. vaginae-specific detection probe target-hybridizing sequence substantially corresponds to the nucleotide sequence of residues 6-21 of SEQ ID NO: 19, and/or the first *G. vaginalis*-specific detection probe target-hybridizing sequence substantially corresponds to the nucleotide sequence of residues 1-18 of SEQ ID NO: 16.

Embodiment 18 is the method of embodiment 17, wherein the first A. vaginae-specific detection probe target-hybridizing sequence comprises the nucleotide sequence of residues 6-21 of SEQ ID NO: 19, and/or the first *G. vaginalis*-specific detection probe target-hybridizing sequence comprises the nucleotide sequence of residues 1-18 of SEQ ID NO: 16.

Embodiment 19 is the method of any one of embodiments 16 to 18, wherein the first *Lactobacillus*-specific detection probe target-hybridizing sequence specifically hybridizes to a target region of each of L. crispatus and L. *jensenii* target nucleic acid, and wherein the method further comprises contacting the one or more amplification products with a second *Lactobacillus*-specific detection probe comprising a target-hybridizing sequence that specifically hybridizes to a target region of L. gasseri target nucleic acid.

Embodiment 20 is the method of embodiment 19, wherein the first *Lactobacillus*-specific detection probe target-hybridizing sequence substantially corresponds to the nucleotide sequence of residues 1-17 of SEQ ID NO: 11, and/or the second *Lactobacillus*-specific detection probe target-hybridizing sequence substantially corresponds to the nucleotide sequence of residues 7-23 of SEQ ID NO: 12.

Embodiment 21 is the method of embodiment 20, wherein the first *Lactobacillus*-specific detection probe target-hybridizing sequence comprises the nucleotide sequence of residues 1-17 of SEQ ID NO: 11, and/or the second *Lactobacillus*-specific detection probe target-hybridizing sequence comprises the nucleotide sequence of residues 7-23 of SEQ ID NO:12.

Embodiment 22 is the method of any one of embodiments 16 to 18, wherein each of the first *Lactobacillus*-specific detection probe, the first A. vaginae-specific detection probe, and the first *G. vaginalis*-specific detection probe comprises a label.

Embodiment 23 is the method of any one of embodiments 19 to 21, wherein each of the first *Lactobacillus*-specific detection probe, the second *Lactobacillus*-specific detection probe, the first A. vaginae-specific detection probe, and the first *G. vaginalis*-specific detection probe comprises a label.

Embodiment 24 is the method of embodiment 22 or 23, wherein the label is a chemiluminescent label or a fluorescent label.

Embodiment 25 is the method of embodiment 22 or 23, wherein the detecting step (3) occurs during the amplifying step (2).

Embodiment 26 is the method of embodiment 25, wherein each detection probe comprises a fluorescent label and a quencher.

Embodiment 27 is the method of embodiment 26, wherein each detection probe is a molecular torch, a molecular beacon, or a TaqMan detection probe.

Embodiment 28 is the method of any one of embodiments 16 to 18, wherein at least one of the first *Lactobacillus*-specific detection probe, the first A. vaginae-specific detection probe, and the first *G. vaginalis*-specific detection probe further comprises a non-target-hybridizing sequence.

Embodiment 29 is the method of embodiment 28, wherein each of the first *Lactobacillus*-specific detection probe, the first A. vaginae-specific detection probe, and the first *G. vaginalis*-specific detection probe is a molecular torch or a molecular beacon.

Embodiment 30 is the method of any one of embodiments 19 to 21, wherein at least one of the first *Lactobacillus*-specific detection probe, the second *Lactobacillus*-specific detection probe, the first A. vaginae-specific detection probe, and the first *G. vaginalis*-specific detection probe further comprises a non-target-hybridizing sequence.

Embodiment 31 is the method of embodiment 30, wherein each of the first *Lactobacillus*-specific detection probe, the second *Lactobacillus*-specific detection probe, the first A. vaginae-specific detection probe, and the first *G. vaginalis*-specific detection probe is a molecular torch or a molecular beacon.

Embodiment 32 is the method of any one of embodiments 1 to 31, wherein the amplification reaction at step (2) is an isothermal amplification reaction.

Embodiment 33 is the method of embodiment 32, wherein the amplification reaction is a transcription-mediated amplification (TMA) reaction.

Embodiment 34 is the method of embodiment 32 or 33, wherein the amplification reaction is a real-time amplification reaction.

Embodiment 35 is a composition or a kit for determining the presence or absence of each of *Lactobacillus* sp., A. vaginae. and *G. vaginalis* in a sample, the composition or kit comprising:

(a) first, second, third, and fourth *Lactobacillus*-specific amplification oligomers for amplifying a target region of a *Lactobacillus* sp. target nucleic acid, wherein (i) the first *Lactobacillus*-specific amplification oligomer comprises a first *Lactobacillus*-specific target-hybridizing sequence substantially corresponding to the nucleotide sequence of residues 28-45 of SEQ ID NO:10; (ii) the second *Lactobacillus*-specific amplification oligomer comprises a second *Lactobacillus*-specific target-hybridizing sequence substantially corresponding to the nucleotide sequence of SEQ ID NO:7; (iii) the third *Lactobacillus*-specific amplification oligomer comprises a third *Lactobacillus*-specific target-hybridizing sequence substantially corresponding to the nucleotide sequence of SEQ ID NO:8; and (iv) the fourth *Lactobacillus*-specific amplification oligomer comprises a fourth *Lactobacillus*-specific target-hybridizing sequence substantially corresponding to the nucleotide sequence of SEQ ID NO:9:

(b) first and second A. vaginae-specific amplification oligomers for amplifying a target region of a A. vaginae target nucleic acid, wherein (i) the first A. vaginae-specific amplification oligomer comprises a first A. vaginae-specific target-hybridizing sequence substantially corresponding to the nucleotide sequence of residues 28-45 of SEQ ID NO:18 and (ii) the second A.

vaginae-specific amplification oligomer comprises a second A. vaginae-specific target-hybridizing sequence substantially corresponding to the nucleotide sequence of SEQ ID NO: 17; and (c) first and second *G. vaginalis*-specific amplification oligomers for amplifying a target region of a *G. vaginalis* target nucleic acid, wherein (i) the first *G. vaginalis*-specific amplification oligomer comprises a first *G. vaginalis*-specific target-hybridizing sequence substantially corresponding to the nucleotide sequence of residues 36-52 of SEQ ID NO:15 and (ii) the second *G. vaginalis*-specific amplification oligomer comprises a second *G. vaginalis*-specific target-hybridizing sequence substantially corresponding to the nucleotide sequence of SEQ ID NO: 14.

Embodiment 36 is the composition or a kit of embodiment 35, wherein
the first *Lactobacillus*-specific target-hybridizing sequence comprises the nucleotide sequence of residues 28-45 of SEQ ID NO:10:
the second *Lactobacillus*-specific target-hybridizing sequence comprises the nucleotide sequence of SEQ ID NO:7:
the third *Lactobacillus*-specific target-hybridizing sequence comprises the nucleotide sequence of SEQ ID NO:8:
the fourth *Lactobacillus*-specific target-hybridizing sequence comprises the nucleotide sequence of SEQ ID NO:9:
the first A. vaginae-specific target-hybridizing sequence comprises the nucleotide sequence of residues 28-45 of SEQ ID NO: 18:
the second A. vaginae-specific target-hybridizing sequence comprises the nucleotide sequence of SEQ ID NO: 17;
the first *G. vaginalis*-specific target-hybridizing sequence comprises the nucleotide sequence of residues 36-52 of SEQ ID NO: 15; and/or
the second *G. vaginalis*-specific target-hybridizing sequence comprises the nucleotide sequence of SEQ ID NO:14.

Embodiment 37 is the composition or a kit of embodiment 35 or 36, wherein the first *Lactobacillus*-specific target-hybridizing sequence consists of the nucleotide sequence of residues 28-45 of SEQ ID NO:10;
the second *Lactobacillus*-specific target-hybridizing sequence consists of the nucleotide sequence of SEQ ID NO:7;
the third *Lactobacillus*-specific target-hybridizing sequence consists of the nucleotide sequence of SEQ ID NO:8;
the fourth *Lactobacillus*-specific target-hybridizing sequence consists of the nucleotide sequence of SEQ ID NO:9;
the first A. vaginae-specific target-hybridizing sequence consists of the nucleotide sequence of residues 28-45 of SEQ ID NO:18:
the second A. vaginae-specific target-hybridizing sequence consists of the nucleotide sequence of SEQ ID NO:17;
the first *G. vaginalis*-specific target-hybridizing sequence consists of the nucleotide sequence of residues 36-52 of SEQ ID NO:15; and/or
the second *G. vaginalis*-specific target-hybridizing sequence consists of the nucleotide sequence of SEQ ID NO: 14.

Embodiment 38 is the composition or a kit of any one of embodiments 35 to 37, wherein
at least one of the first *Lactobacillus*-specific amplification oligomer, the first A. vaginae-specific amplification oligomer, and the first *G. vaginalis*-specific amplification oligomer is a promoter primer or promoter provider further comprising a promoter sequence located 5' to the respective target hybridizing sequence.

Embodiment 39 is the composition or a kit of embodiment 38, wherein the promoter sequence is a T7 promoter sequence.

Embodiment 40 is the composition or a kit of embodiment 39, wherein the promoter sequence has the nucleotide sequence of residues 1-27 of SEQ ID NO:10.

Embodiment 41 is the composition or a kit of embodiment 38, wherein the first *Lactobacillus*-specific amplification oligomer comprises the nucleotide sequence of SEQ ID NO: 10;
the first A. vaginae-specific amplification oligomer comprises the nucleotide sequence of SEQ ID NO: 18; and/or
the first *G. vaginalis*-specific amplification oligomer comprises the nucleotide sequence of residues 9-52 of SEQ ID NO:15.

Embodiment 42 is the composition or a kit of embodiment 41, wherein the first *G. vaginalis*-specific amplification oligomer comprises the nucleotide sequence of SEQ ID NO: 15.

Embodiment 43 is the composition or a kit of any one of embodiments 35 to 42, further comprising at least one capture probe oligomer comprising a target-hybridizing sequence covalently attached to a sequence or moiety that binds to an immobilized probe.

Embodiment 44 is the composition or a kit of embodiment 43, wherein the composition or kit comprises first and second capture probe oligomers,
wherein the first capture probe oligomer comprises a target-hybridizing sequence that specifically hybridizes to a target sequence within the *Lactobacillus* sp. target nucleic acid and the second capture probe target-hybridizing sequence comprises a target-hybridizing sequence that specifically hybridizes to a target sequence within each of the A. vaginae and *G. vaginalis* target nucleic acids, and
wherein each of the first and second capture probe target-hybridizing sequences is covalently attached to the sequence or moiety that binds to the immobilized probe.

Embodiment 45 is the composition or a kit of embodiment 44, wherein the first capture probe target-hybridizing sequence specifically hybridizes to a target sequence within each of L. crispatus, L. *jensenii*, and L. gasseri target nucleic acid.

Embodiment 46 is the composition or a kit of embodiment 45, wherein
the first capture probe target-hybridizing sequence substantially corresponds to the nucleotide sequence of residues 1-19 of SEQ ID NO:6.

Embodiment 47 is the composition or a kit of embodiment 45 or 46, wherein
the second capture probe target-hybridizing sequence substantially corresponds to the nucleotide sequence of residues 1-20 of SEQ ID NO: 13.

Embodiment 48 is the composition or a kit of embodiment 47, wherein
the first capture probe oligomer comprises the nucleotide sequence of SEQ ID NO:6, and/or the second capture probe oligomer comprises the nucleotide sequence of SEQ ID NO: 13.

Embodiment 49 is the composition or a kit of any one of embodiments 35 to 48, further comprising a first *Lactobacillus*-specific detection probe comprising a target-hybridizing sequence that specifically hybridizes to the *Lactobacillus* sp. target region, a first A. vaginae-specific detection probe comprising a target-hybridizing sequence that specifically hybridizes to the A. vaginae target region, and a first *G. vaginalis*-specific detection probe comprising a target-hybridizing sequence that specifically hybridizes to the *G. vaginalis* target region.

Embodiment 50 is the composition or a kit of embodiment 49, wherein the first A. vaginae-specific detection probe target-hybridizing sequence substantially corresponds to the nucleotide sequence of residues 6-21 of SEQ ID NO: 19, and/or the first *G. vaginalis*-specific detection probe target-hybridizing sequence substantially corresponds to the nucleotide sequence of residues 1-18 of SEQ ID NO: 16.

Embodiment 51 is the composition or a kit of embodiment 50, wherein
the first A. vaginae-specific detection probe target-hybridizing sequence comprises the nucleotide sequence of residues 6-21 of SEQ ID NO: 19, and/or
the first *G. vaginalis*-specific detection probe target-hybridizing sequence comprises the nucleotide sequence of residues 1-18 of SEQ ID NO:16.

Embodiment 52 is the composition or a kit of any one of embodiments 49 to 51, wherein the first *Lactobacillus*-specific detection probe target-hybridizing sequence specifically hybridizes to a target region of each of L. crispatus and L. *jensenii* target nucleic acid, and
wherein the composition or kit further comprises a second *Lactobacillus*-specific detection probe comprising a target-hybridizing sequence that specifically hybridizes to a target region of L. gasseri target nucleic acid.

Embodiment 53 is the composition or a kit of embodiment 52, wherein
the first *Lactobacillus*-specific detection probe target-hybridizing sequence substantially corresponds to the nucleotide sequence of residues 1-17 of SEQ ID NO: 11, and/or
the second *Lactobacillus*-specific detection probe target-hybridizing sequence substantially corresponds to the nucleotide sequence of residues 7-23 of SEQ ID NO: 12.

Embodiment 54 is the composition or a kit of embodiment 53, wherein the first *Lactobacillus*-specific detection probe target-hybridizing sequence comprises the nucleotide sequence of residues 1-17 of SEQ ID NO: 11, and/or the second *Lactobacillus*-specific detection probe target-hybridizing sequence comprises the nucleotide sequence of residues 7-23 of SEQ ID NO: 12.

Embodiment 55 is the composition or a kit of any one of embodiments 49 to 51, wherein each of the first *Lactobacillus*-specific detection probe, the first A. vaginae-specific detection probe, and the first *G. vaginalis*-specific detection probe comprises a label.

Embodiment 56 is the composition or a kit of any one of embodiments 52 to 54, wherein each of the first *Lactobacillus*-specific detection probe, the second *Lactobacillus*-specific detection probe, the first A. vaginae-specific detection probe, and the first *G. vaginalis*-specific detection probe comprises a label.

Embodiment 57 is the composition or a kit of embodiment 55 or 56, wherein the label is a chemiluminescent label or a fluorescent label.

Embodiment 58 is the composition or a kit of embodiment 55 or 56, wherein each detection probe comprises a fluorescent label and a quencher.

Embodiment 59 is the composition or a kit of embodiment 58, wherein each detection probe is a molecular torch, a molecular beacon, or a TaqMan detection probe.

Embodiment 60 is the composition or a kit of any one of embodiments 49 to 51, wherein at least one of the first *Lactobacillus*-specific detection probe, the first A. vaginae-specific detection probe, and the first *G. vaginalis*-specific detection probe further comprises a non-target-hybridizing sequence.

Embodiment 61 is the composition or a kit of embodiment 60, wherein each of the first *Lactobacillus*-specific detection probe, the first A. vaginae-specific detection probe, and the first *G. vaginalis*-specific detection probe is a molecular torch or a molecular beacon.

Embodiment 62 is the composition or a kit of any one of embodiments 52 to 54, wherein at least one of the first *Lactobacillus*-specific detection probe, the second *Lactobacillus*-specific detection probe, the first A. vaginae-specific detection probe, and the first *G. vaginalis*-specific detection probe further comprises a non-target-hybridizing sequence.

Embodiment 63 is the composition or a kit of embodiment 62, wherein each of the first *Lactobacillus*-specific detection probe, the second *Lactobacillus*-specific detection probe, the first A. vaginae-specific detection probe, and the first *G. vaginalis*-specific detection probe is a molecular torch or a molecular beacon.

Embodiment 64 is a method for determining the presence or absence of Bacterial Vaginosis (BV) in a subject, the method comprising:
(a) providing a sample from a subject suspected of having BV:
(b) performing an assay for the detection of *Lactobacillus* sp., A. vaginae. and *G. vaginalis* in the sample:
(c) for each of *Lactobacillus* sp., A. vaginae. and *G. vaginalis*, assigning a quantitative value based on the detection assay:
(d) subtracting the *Lactobacillus* sp. quantitative value from the greater of the A. vaginae quantitative value and the *G. vaginalis* quantitative value:
(e) assigning a single BV score based on step (d); and
(f) determining the presence or absence of BV in the subject based on a comparison of the BV score to a cutoff value.

Embodiment 65 is the method of embodiment 64, wherein a minimum quantitative value is imposed for *Lactobacillus* sp. at step (c).

Embodiment 66 is the method of embodiment 64 or 65, wherein a minimum quantitative value is imposed for A. vaginae and *G. vaginalis* at step (c).

Embodiment 67 is the method of any one of embodiments 64 to 66, wherein the quantitative value for each of *Lactobacillus* sp., A. vaginae. and *G. vaginalis* is standardized.

Embodiment 68 is the method of embodiment 67, wherein the quantitative value for each of *Lactobacillus* sp., A. vaginae. and *G. vaginalis* is in units of log copies and standardization comprises subtracting a median population value from a value determined from the detection assay.

Embodiment 69 is the method of any one of embodiments 64 to 68, wherein the quantitative value for each of *Lactobacillus* sp., A. vaginae, and *G. vaginalis* is weighted.

Embodiment 70 is the method of any one of embodiments 64 to 69, wherein step (d) further comprises adding an adjustment constant.

Embodiment 71 is the method of any one of embodiments 64 to 69, wherein step (d) further comprises adding an internal control (IC) adjustment factor that compensates for sample inhibition of the detection assay, wherein the IC adjustment factor is based on a ratio of (i) an observed IC value generated from the detection assay to (ii) an expected IC value for the detection assay.

Embodiment 72 is the method of embodiment 64, wherein the BV score is assigned using the equation $$BV\ score = C_0 + W_L \text{Max}(L_S, F_{LS}) + W_{GA} \text{Max}(As, Gs, F_{GAS}) + W_{IC} \text{Log}\ 2(\text{ICRatio}),$$

wherein
$C_0$ is an adjustment constant:
WL is a weighting constant for *Lactobacillus* sp.:
Max ($L_S$, $F_{LS}$) is the greater of $L_S$ and $F_{LS}$, wherein $L_S$ is an observed standardized quantitative value for *Lactobacillus* sp. and $F_{LS}$ is an imposed minimum standardized quantitative value for *Lactobacillus* sp.:
$W_{GA}$ is a weighting constant for A. vaginae and G. vaginalis;
Max (As, Gs, $F_{GAS}$) is the greater of As, Gs, and $F_{GAS}$, wherein As is an observed standardized quantitative value for A. vaginae, Gs is an observed standardized quantitative value for G. vaginalis, and $F_{GAS}$ is an imposed minimum standardized quantitative value for A. vaginae and G. vaginalis:
$W_{IC}$ is an internal control (IC) weighting constant; and
ICRatio is a ratio of (i) an observed internal control (IC) value generated from the detection assay to (ii) an expected IC value for the detection assay.

Embodiment 73 is the method of embodiment 72, wherein $F_{GAS}$ is 0.

Embodiment 74 is the method of any one of embodiments 64 to 73, wherein the assay for detection of *Lactobacillus* sp., A. vaginae. and, G. vaginalis is a nucleic-acid-based detection assay.

Embodiment 75 is the method of embodiment 74, wherein the nucleic-acid-based detection assay targets the 16S rRNA of *Lactobacillus* sp., A. vaginae. and G. vaginalis.

Embodiment 76 is the method of embodiment 75, wherein the nucleic-acid-based detection assay targets
(a) a L. crispatus 16S rRNA region corresponding to a region of SEQ ID NO:1 from about nucleotide position 40 to about nucleotide position 265;
(b) a L. jensenii 16S rRNA region corresponding to a region of SEQ ID NO:2 from about nucleotide position 43 to about nucleotide position 247:
(c) a L. gasseri 16S rRNA region corresponding to a region of SEQ ID NO:3 from about nucleotide position 93 to about nucleotide position 298;
(d) a A. vaginae 16S rRNA region corresponding to a region of SEQ ID NO:4 from about nucleotide position 540 to about nucleotide position 625; and/or
(e) a G. vaginalis 16S rRNA region corresponding to a region of SEQ ID NO:5 from about nucleotide position 172 to about nucleotide position 227.

Embodiment 77 is the method of any one of embodiments 74 to 76, wherein the nucleic-acid-based detection assay is an amplification-based assay.

Embodiment 78 is the method of embodiment 77, wherein the amplification-based assay comprises an isothermal amplification reaction.

Embodiment 79 is the method of embodiment 78, wherein the amplification reaction is a transcription-mediated amplification (TMA) reaction.

Embodiment 80 is the method of embodiment 78 or 79, wherein the amplification reaction is a real-time amplification reaction.

Embodiment 81 is the method of embodiment 79, wherein the nucleic-acid-based detection assay is an amplification-based assay comprising
(1) contacting the sample with
first, second, third, and fourth *Lactobacillus*-specific amplification oligomers for amplifying a target region of a *Lactobacillus* sp. target nucleic acid, wherein (i) the first *Lactobacillus*-specific amplification oligomer comprises a first *Lactobacillus*-specific target-hybridizing sequence substantially corresponding to the nucleotide sequence of residues 28-45 of SEQ ID NO:10; (ii) the second *Lactobacillus*-specific amplification oligomer comprises a second *Lactobacillus*-specific target-hybridizing sequence substantially corresponding to the nucleotide sequence of SEQ ID NO:7: (iii) the third *Lactobacillus*-specific amplification oligomer comprises a third *Lactobacillus*-specific target-hybridizing sequence substantially corresponding to the nucleotide sequence of SEQ ID NO:8; and (iv) the fourth *Lactobacillus*-specific amplification oligomer comprises a fourth *Lactobacillus*-specific target-hybridizing sequence substantially corresponding to the nucleotide sequence of SEQ ID NO:9: first and second A. vaginae-specific amplification oligomers for amplifying a target region of a A. vaginae target nucleic acid, wherein (i) the first A. vaginae-specific amplification oligomer comprises a first A. vaginae-specific target-hybridizing sequence substantially corresponding to the nucleotide sequence of residues 28-45 of SEQ ID NO:18 and (ii) the second A. vaginae-specific amplification oligomer comprises a second A. vaginae-specific target-hybridizing sequence substantially corresponding to the nucleotide sequence of SEQ ID NO: 17; and
first and second G. vaginalis-specific amplification oligomers for amplifying a target region of a G. vaginalis target nucleic acid, wherein (i) the first G. vaginalis-specific amplification oligomer comprises a first G. vaginalis-specific target-hybridizing sequence substantially corresponding to the nucleotide sequence of residues 36-52 of SEQ ID NO:15 and (ii) the second G. vaginalis-specific amplification oligomer comprises a second G. vaginalis-specific target-hybridizing sequence substantially corresponding to the nucleotide sequence of SEQ ID NO:14;
(2) performing an in vitro nucleic acid amplification reaction, wherein any *Lactobacillus* sp., A. vaginae. and G. vaginalis target nucleic acid, if present in the sample, is used as a template for generating one or more amplification products corresponding to the *Lactobacillus* sp., A. vaginae. and G. vaginalis target regions; and
(3) detecting the presence or absence of the one or more amplification products.

Embodiment 82 is the method of embodiment 81, wherein
the first *Lactobacillus*-specific target-hybridizing sequence comprises the nucleotide sequence of residues 28-45 of SEQ ID NO:10:
the second *Lactobacillus*-specific target-hybridizing sequence comprises the nucleotide sequence of SEQ ID NO:7;
the third *Lactobacillus*-specific target-hybridizing sequence comprises the nucleotide sequence of SEQ ID NO:8;

the fourth *Lactobacillus*-specific target-hybridizing sequence comprises the nucleotide sequence of SEQ ID NO:9;

the first A. vaginae-specific target-hybridizing sequence comprises the nucleotide sequence of residues 28-45 of SEQ ID NO: 18:

the second A. vaginae-specific target-hybridizing sequence comprises the nucleotide sequence of SEQ ID NO: 17;

the first *G. vaginalis*-specific target-hybridizing sequence comprises the nucleotide sequence of residues 36-52 of SEQ ID NO: 15; and/or the second *G. vaginalis*-specific target-hybridizing sequence comprises the nucleotide sequence of SEQ ID NO: 14.

Embodiment 83 is the method of embodiment 81 or 82, wherein the first *Lactobacillus*-specific target-hybridizing sequence consists of the nucleotide sequence of residues 28-45 of SEQ ID NO: 10:

the second *Lactobacillus*-specific target-hybridizing sequence consists of the nucleotide sequence of SEQ ID NO:7;

the third *Lactobacillus*-specific target-hybridizing sequence consists of the nucleotide sequence of SEQ ID NO:8:

the fourth *Lactobacillus*-specific target-hybridizing sequence consists of the nucleotide sequence of SEQ ID NO:9;

the first A. vaginae-specific target-hybridizing sequence consists of the nucleotide sequence of residues 28-45 of SEQ ID NO: 18:

the second A. vaginae-specific target-hybridizing sequence consists of the nucleotide sequence of SEQ ID NO: 17;

the first *G. vaginalis*-specific target-hybridizing sequence consists of the nucleotide sequence of residues 36-52 of SEQ ID NO: 15; and/or the second *G. vaginalis*-specific target-hybridizing sequence consists of the nucleotide sequence of SEQ ID NO: 14.

Embodiment 84 is the method of any one of embodiments 81 to 83, wherein at least one of the first *Lactobacillus*-specific amplification oligomer, the first A. vaginae-specific amplification oligomer, and the first *G. vaginalis*-specific amplification oligomer is a promoter primer or promoter provider further comprising a promoter sequence located 5' to the respective target hybridizing sequence.

Embodiment 85 is the method of embodiment 84, wherein the promoter sequence is a T7 promoter sequence.

Embodiment 86 is the method of embodiment 85, wherein the promoter sequence has the nucleotide sequence of residues 1-27 of SEQ ID NO: 10.

Embodiment 87 is the method of embodiment 84, wherein the first *Lactobacillus*-specific amplification oligomer comprises the nucleotide sequence of SEQ ID NO: 10;

the first A. vaginae-specific amplification oligomer comprises the nucleotide sequence of SEQ ID NO: 18; and/or the first *G. vaginalis*-specific amplification oligomer comprises the nucleotide sequence of residues 9-52 of SEQ ID NO:15.

Embodiment 88 is the method of embodiment 87, wherein the first *G. vaginalis*-specific amplification oligomer comprises the nucleotide sequence of SEQ ID NO: 15.

Embodiment 89 is the method of any one of embodiments 81 to 88, further comprising purifying the *Lactobacillus* sp., A. vaginae, and *G. vaginalis* target nucleic acids, if present, from other components in the sample before step (2).

Embodiment 90 is the method of embodiment 89, wherein the purifying step comprises contacting the sample with at least one capture probe oligomer comprising a target-hybridizing sequence covalently attached to a sequence or moiety that binds to an immobilized probe.

Embodiment 91 is the method of embodiment 90, wherein the sample is contacted with first and second capture probe oligomers, wherein the first capture probe oligomer comprises a target-hybridizing sequence that specifically hybridizes to a target sequence within the *Lactobacillus* sp. target nucleic acid and the second capture probe target-hybridizing sequence comprises a target-hybridizing sequence that specifically hybridizes to a target sequence within each of the A. vaginae and *G. vaginalis* target nucleic acids, and wherein each of the first and second capture probe target-hybridizing sequences is covalently attached to the sequence or moiety that binds to the immobilized probe.

Embodiment 92 is the method of embodiment 91, wherein the first capture probe target-hybridizing sequence specifically hybridizes to a target sequence within each of L. crispatus, L. *jensenii*, and L. gasseri target nucleic acid.

Embodiment 93 is the method of embodiment 92, wherein the first capture probe target-hybridizing sequence substantially corresponds to the nucleotide sequence of residues 1-19 of SEQ ID NO:6.

Embodiment 94 is the method of embodiment 92 or 93, wherein the second capture probe target-hybridizing sequence substantially corresponds to the nucleotide sequence of residues 1-20 of SEQ ID NO:13.

Embodiment 95 is the method of embodiment 94, wherein the first capture probe oligomer comprises the nucleotide sequence of SEQ ID NO:6, and/or the second capture probe oligomer comprises the nucleotide sequence of SEQ ID NO: 13.

Embodiment 96 is the method of any one of embodiments 81 to 95, wherein the detecting step (3) comprises contacting the one or more amplification products with a first *Lactobacillus*-specific detection probe comprising a target-hybridizing sequence that specifically hybridizes to the *Lactobacillus* sp. target region, a first A. vaginae-specific detection probe comprising a target-hybridizing sequence that specifically hybridizes to the A. vaginae target region, and a first *G. vaginalis*-specific detection probe comprising a target-hybridizing sequence that specifically hybridizes to the *G. vaginalis* target region, and detecting the presence or absence of any target-hybridized *Lactobacillus*-specific, A. vaginae-specific, and/or *G. vaginalis*-specific detection probe.

Embodiment 97 is the method of embodiment 96, wherein the first A. vaginae-specific detection probe target-hybridizing sequence substantially corresponds to the nucleotide sequence of residues 6-21 of SEQ ID NO: 19, and/or the first *G. vaginalis*-specific detection probe target-hybridizing sequence substantially corresponds to the nucleotide sequence of residues 1-18 of SEQ ID NO: 16.

Embodiment 98 is the method of embodiment 97, wherein the first A. vaginae-specific detection probe target-hybridizing sequence comprises the nucleotide sequence of residues 6-21 of SEQ ID NO:19, and/or the first *G. vaginalis*-specific detection probe target-hybridizing sequence comprises the nucleotide sequence of residues 1-18 of SEQ ID NO: 16.

Embodiment 99 is the method of any one of embodiments 96 to 98, wherein the first *Lactobacillus*-specific detection probe target-hybridizing sequence specifically hybridizes to a target region of each of L. crispatus and L. *jensenii* target nucleic acid, and
wherein the method further comprises contacting the one or more amplification products with a second *Lactobacillus*-specific detection probe comprising a target-hybridizing sequence that specifically hybridizes to a target region of L. gasseri target nucleic acid.

Embodiment 100 is the method of embodiment 99, wherein
the first *Lactobacillus*-specific detection probe target-hybridizing sequence substantially corresponds to the nucleotide sequence of residues 1-17 of SEQ ID NO: 11, and/or
the second *Lactobacillus*-specific detection probe target-hybridizing sequence substantially corresponds to the nucleotide sequence of residues 7-23 of SEQ ID NO: 12.

Embodiment 101 is the method of embodiment 100, wherein
the first *Lactobacillus*-specific detection probe target-hybridizing sequence comprises the nucleotide sequence of residues 1-17 of SEQ ID NO: 11, and/or the second *Lactobacillus*-specific detection probe target-hybridizing sequence comprises the nucleotide sequence of residues 7-23 of SEQ ID NO: 12.

Embodiment 102 is the method of any one of embodiments 96 to 98, wherein each of the first *Lactobacillus*-specific detection probe, the first A. vaginae-specific detection probe, and the first *G. vaginalis*-specific detection probe comprises a label.

Embodiment 103 is the method of any one of embodiments 99 to 101, wherein each of the first *Lactobacillus*-specific detection probe, the second *Lactobacillus*-specific detection probe, the first A. vaginae-specific detection probe, and the first *G. vaginalis*-specific detection probe comprises a label.

Embodiment 104 is the method of embodiment 102 or 103, wherein the label is a chemiluminescent label or a fluorescent label.

Embodiment 105 is the method of embodiment 102 or 103, wherein the detecting step (3) occurs during the amplifying step (2).

Embodiment 106 is the method of embodiment 105, wherein each detection probe comprises a fluorescent label and a quencher.

Embodiment 107 is the method of embodiment 106, wherein each detection probe is a molecular torch, a molecular beacon, or a TaqMan detection probe.

Embodiment 108 is the method of any one of embodiments 96 to 98, wherein at least one of the first *Lactobacillus*-specific detection probe, the first A. vaginae-specific detection probe, and the first *G. vaginalis*-specific detection probe further comprises a non-target-hybridizing sequence.

Embodiment 109 is the method of embodiment 108, wherein each of the first *Lactobacillus*-specific detection probe, the first A. vaginae-specific detection probe, and the first *G. vaginalis*-specific detection probe is a molecular torch or a molecular beacon.

Embodiment 110 is the method of any one of embodiments 99 to 101, wherein at least one of the first *Lactobacillus*-specific detection probe, the second *Lactobacillus*-specific detection probe, the first A. vaginae-specific detection probe, and the first *G. vaginalis*-specific detection probe further comprises a non-target-hybridizing sequence.

Embodiment 111 is the method of embodiment 110, wherein each of the first *Lactobacillus*-specific detection probe, the second *Lactobacillus*-specific detection probe, the first A. vaginae-specific detection probe, and the first *G. vaginalis*-specific detection probe is a molecular torch or a molecular beacon.

Embodiment 112 is the method of any one of embodiments 81 to 111, wherein the amplification reaction at step (2) is an isothermal amplification reaction.

Embodiment 113 is the method of embodiment 112, wherein the amplification reaction is a transcription-mediated amplification (TMA) reaction.

Embodiment 114 is the method of embodiment 112 or 113, wherein the amplification reaction is a real-time amplification reaction.

Embodiment 115 is the method of any one of embodiments 64 to 114, wherein the method comprises the detection of no more than ten bacterial genera associated with BV.

Embodiment 116 is the method of any one of embodiments 64 to 114, wherein the method comprises the detection of no more than five bacterial genera associated with BV.

Embodiment 117 is the method of any one of embodiments 64 to 114, wherein the method does not include detection of bacterial genera associated with BV other than *Lactobacillus*, Atopobium, and *Gardnerella*.

Embodiment 118 is the method of any one of embodiments 64 to 117, wherein if the presence of BV is indicated in the subject, then the method further comprises administering a treatment regime for BV to the subject.

Embodiment 119 is the method of any one of embodiments 64 to 117, wherein the method is a method for monitoring BV in the subject and the subject is undergoing a treatment regime for BV prior to step (a).

Embodiment 120 is the method of embodiment 119, wherein if the presence of BV is indicated in the subject, then the method further comprises either (i) administering the treatment regime for BV to the subject or (ii) administering a different treatment regime for BV to the subject.

Embodiment 121 is a method for determining the presence or absence of *Lactobacillus* sp. in a sample, the method comprising:
(1) contacting a sample, said sample suspected of containing *Lactobacillus* sp., with first, second, third, and fourth amplification oligomers for amplifying a target region of a *Lactobacillus* sp. target nucleic acid, wherein (i) the first amplification oligomer comprises a first target-hybridizing sequence substantially corresponding to the nucleotide sequence of residues 28-45 of SEQ ID NO:10; (ii) the amplification oligomer comprises a second target-hybridizing sequence substantially corresponding to the nucleotide sequence of SEQ ID NO:7: (iii) the third amplification oligomer comprises a third target-hybridizing sequence substantially corresponding to the nucleotide sequence of SEQ ID NO:8; and (iv) the fourth amplification oligomer comprises a fourth target-hybridizing sequence substantially corresponding to the nucleotide sequence of SEQ ID NO:9;
(2) performing an in vitro nucleic acid amplification reaction, wherein any *Lactobacillus* sp. target nucleic acid, if present in the sample, is used as a template for generating one or more amplification products corresponding to the *Lactobacillus* sp. target region; and (3) detecting the presence or absence of the one or more amplification products, thereby determining the presence or absence of *Lactobacillus* sp. in the sample.

Embodiment 122 is the method of embodiment 121, wherein
the first target-hybridizing sequence comprises the nucleotide sequence of residues 28-45 of SEQ ID NO: 10;
the second target-hybridizing sequence comprises the nucleotide sequence of SEQ ID NO: 7:
the third target-hybridizing sequence comprises the nucleotide sequence of SEQ ID NO: 8; and/or
the fourth target-hybridizing sequence comprises the nucleotide sequence of SEQ ID NO: 9.

Embodiment 123 is the method of embodiment 122, wherein
the first target-hybridizing sequence consists of the nucleotide sequence of residues 28-45 of SEQ ID NO:10;
the second target-hybridizing sequence consists of the nucleotide sequence of SEQ ID NO: 7:
the third target-hybridizing sequence consists of the nucleotide sequence of SEQ ID NO: 8; and/or
the fourth target-hybridizing sequence consists of the nucleotide sequence of SEQ ID NO: 9.

Embodiment 124 is the method of any one of embodiments 121 to 123, wherein the first amplification oligomer is a promoter primer or promoter provider further comprising a promoter sequence located 5' to the respective target hybridizing sequence.

Embodiment 125 is the method of embodiment 124, wherein the promoter sequence is a T7 promoter sequence.

Embodiment 126 is the method of embodiment 125, wherein the promoter sequence has the nucleotide sequence of residues 1-27 of SEQ ID NO: 10.

Embodiment 127 is the method of embodiment 124, wherein
the first amplification oligomer comprises the nucleotide sequence of SEQ ID NO: 10.

Embodiment 128 is the method of any one of embodiments 121 to 127, further comprising purifying the *Lactobacillus* sp. target nucleic acid, if present, from other components in the sample before step (2).

Embodiment 129 is the method of embodiment 128, wherein the purifying step comprises contacting the sample with at least one capture probe oligomer comprising a target-hybridizing sequence covalently attached to a sequence or moiety that binds to an immobilized probe, wherein the capture probe target-hybridizing sequence specifically hybridizes to a target sequence within the *Lactobacillus* sp. target nucleic acid.

Embodiment 130 is the method of embodiment 129, wherein the capture probe target-hybridizing sequence specifically hybridizes to a target sequence within each of L. crispatus, L. jensenii, and L. gasseri target nucleic acid.

Embodiment 131 is the method of embodiment 130, wherein
the first capture probe target-hybridizing sequence substantially corresponds to the nucleotide sequence of residues 1-19 of SEQ ID NO:6.

Embodiment 132 is the method of embodiment 131, wherein the capture probe oligomer comprises the nucleotide sequence of SEQ ID NO:6.

Embodiment 133 is the method of any one of embodiments 121 to 132, wherein the detecting step (3) comprises contacting the one or more amplification products with a first detection probe comprising a target-hybridizing sequence that specifically hybridizes to the *Lactobacillus* sp. target region, and detecting the presence or absence of any target-hybridized detection probe.

Embodiment 134 is the method of embodiment 133, wherein the first detection probe target-hybridizing sequence specifically hybridizes to a target region of each of L. crispatus and L. jensenii target nucleic acid, and
wherein the method further comprises contacting the one or more amplification products with a second detection probe comprising a target-hybridizing sequence that specifically hybridizes to a target region of L. gasseri target nucleic acid.

Embodiment 135 is the method of embodiment 134, wherein
the first detection probe target-hybridizing sequence substantially corresponds to the nucleotide sequence of residues 1-17 of SEQ ID NO: 11, and/or
the second detection probe target-hybridizing sequence substantially corresponds to the nucleotide sequence of residues 7-23 of SEQ ID NO: 12.

Embodiment 136 is the method of embodiment 135, wherein
the first detection probe target-hybridizing sequence comprises the nucleotide sequence of residues 1-17 of SEQ ID NO: 11, and/or
the second detection probe target-hybridizing sequence comprises the nucleotide sequence of residues 7-23 of SEQ ID NO:12.

Embodiment 137 is the method of embodiment 133, wherein the first detection probe comprises a label.

Embodiment 138 is the method of embodiment 137, wherein the label is a chemiluminescent label or a fluorescent label.

Embodiment 139 is the method of embodiment 137, wherein the detecting step (3) occurs during the amplifying step (2).

Embodiment 140 is the method of embodiment 139, wherein the detection probe comprises a fluorescent label and a quencher.

Embodiment 141 is the method of embodiment 140, wherein the detection probe is a molecular torch, a molecular beacon, or a TaqMan detection probe.

Embodiment 142 is the method of any one of embodiments 134 to 136, wherein each of the first and second *Lactobacillus*-specific detection probes comprises a label Embodiment 143 is the method of embodiment 142, wherein the label is a chemiluminescent label or a fluorescent label.

Embodiment 144 is the method of embodiment 142, wherein the detecting step (3) occurs during the amplifying step (2).

Embodiment 145 is the method of embodiment 144, wherein each detection probe comprises a fluorescent label and a quencher.

Embodiment 146 is the method of embodiment 145, wherein each detection probe is a molecular torch, a molecular beacon, or a TaqMan detection probe.

Embodiment 147 is the method of embodiment 133, wherein the first detection probe further comprises a non-target-hybridizing sequence.

Embodiment 148 is the method of embodiment 147, wherein the first detection probe is a molecular torch or a molecular beacon.

Embodiment 149 is the method of any one of embodiments 134 to 136, wherein at least one of the first and second detection probes further comprises a non-target-hybridizing sequence.

Embodiment 150 is the method of embodiment 149, wherein each of the first and second detection probes is a molecular torch or a molecular beacon.

Embodiment 151 is a method for determining the presence or absence of A. vaginae in a sample, the method comprising:
(1) contacting a sample, said sample suspected of containing A. vaginae, with first and second amplification oligomers for amplifying a target region of a A. vaginae target nucleic acid, wherein (i) the first amplification oligomer comprises a first target-hybridizing sequence substantially corresponding to the nucleotide sequence of residues 28-45 of SEQ ID NO:18 and (ii) the second amplification oligomer comprises a second target-hybridizing sequence substantially corresponding to the nucleotide sequence of SEQ ID NO:17;
(2) performing an in vitro nucleic acid amplification reaction, wherein any A. vaginae target nucleic acid, if present in the sample, is used as a template for generating one or more amplification products corresponding to the A. vaginae target region; and
(3) detecting the presence or absence of the one or more amplification products, thereby determining the presence or absence of A. vaginae in the sample.

Embodiment 152 is the method of embodiment 151, wherein
the first target-hybridizing sequence comprises the nucleotide sequence of residues 28-45 of SEQ ID NO: 18; and/or
the second target-hybridizing sequence comprises the nucleotide sequence of SEQ ID NO: 17.

Embodiment 153 is the method of embodiment 151 or 152, wherein
the first target-hybridizing sequence consists of the nucleotide sequence of residues 28-45 of SEQ ID NO: 18; and/or
the second target-hybridizing sequence consists of the nucleotide sequence of SEQ ID NO: 17.

Embodiment 154 is the method of any one of embodiments 151 to 153, wherein the first amplification oligomer is a promoter primer or promoter provider further comprising a promoter sequence located 5' to the respective target hybridizing sequence.

Embodiment 155 is the method of embodiment 154, wherein the promoter sequence is a T7 promoter sequence.

Embodiment 156 is the method of embodiment 155, wherein the promoter sequence has the nucleotide sequence of residues 1-27 of SEQ ID NO: 18.

Embodiment 157 is the method of embodiment 154, wherein the first amplification oligomer comprises the nucleotide sequence of SEQ ID NO: 18.

Embodiment 158 is the method of any one of embodiments 151 to 157, further comprising purifying the A. vaginae target nucleic acid, if present, from other components in the sample before step (2).

Embodiment 159 is the method of embodiment 158, wherein the purifying step comprises contacting the sample with at least one capture probe oligomer comprising a target-hybridizing sequence covalently attached to a sequence or moiety that binds to an immobilized probe, wherein the capture probe target-hybridizing sequence specifically hybridizes to a target sequence within the A. vaginae target nucleic acid.

Embodiment 160 is the method of embodiment 159, wherein the capture probe target-hybridizing sequence substantially corresponds to the nucleotide sequence of residues 1-20 of SEQ ID NO:13.

Embodiment 161 is the method of embodiment 160, wherein the capture probe oligomer comprises the nucleotide sequence of SEQ ID NO: 13.

Embodiment 162 is the method of any one of embodiments 151 to 161, wherein the detecting step (3) comprises contacting the one or more amplification products with a detection probe comprising a target-hybridizing sequence that specifically hybridizes to the A. vaginae target region, and
detecting the presence or absence of any target-hybridized detection probe.

Embodiment 163 is the method of embodiment 162, wherein the detection probe target-hybridizing sequence substantially corresponds to the nucleotide sequence of residues 6-21 of SEQ ID NO: 19.

Embodiment 164 is the method of embodiment 163, wherein the detection probe target-hybridizing sequence comprises the nucleotide sequence of residues 6-21 of SEQ ID NO: 19.

Embodiment 165 is the method of any one of embodiments 162 to 164, wherein the detection probe comprises a label.

Embodiment 166 is the method of embodiment 165, wherein the label is a chemiluminescent label or a fluorescent label.

Embodiment 167 is the method of embodiment 165, wherein the detecting step (3) occurs during the amplifying step (2).

Embodiment 168 is the method of embodiment 167, wherein the detection probe comprises a fluorescent label and a quencher.

Embodiment 169 is the method of embodiment 168, wherein the detection probe is a molecular torch, a molecular beacon, or a TaqMan detection probe.

Embodiment 170 is the method of any one of embodiments 162 to 164, wherein the detection probe further comprises a non-target-hybridizing sequence.

Embodiment 171 is the method of embodiment 170, wherein the detection probe is a molecular torch or a molecular beacon.

Embodiment 172 is a method for determining the presence or absence of G. vaginalis in a sample, the method comprising:
(1) contacting a sample, said sample suspected of containing G. vaginalis, with first and second amplification oligomers for amplifying a target region of a G. vaginalis target nucleic acid, wherein (i) the first amplification oligomer comprises a first target-hybridizing sequence substantially corresponding to the nucleotide sequence of residues 36-52 of SEQ ID NO:15 and (ii) the second amplification oligomer comprises a second target-hybridizing sequence substantially corresponding to the nucleotide sequence of SEQ ID NO: 14:
(2) performing an in vitro nucleic acid amplification reaction, wherein any G. vaginalis target nucleic acid, if present in the sample, is used as a template for generating one or more amplification products corresponding to the G. vaginalis target region; and
(3) detecting the presence or absence of the one or more amplification products, thereby determining the presence or absence of G. vaginalis in the sample.

Embodiment 173 is the method of embodiment 172, wherein
the first target-hybridizing sequence comprises the nucleotide sequence of residues 36-52 of SEQ ID NO: 15; and/or the second target-hybridizing sequence comprises the nucleotide sequence of SEQ ID NO: 14.

Embodiment 174 is the method of embodiment 172 or 173, wherein
the first target-hybridizing sequence consists of the nucleotide sequence of residues 36-52 of SEQ ID NO: 15; and/or the second target-hybridizing sequence consists of the nucleotide sequence of SEQ ID NO: 14.

Embodiment 175 is the method of any one of embodiments 172 to 174, wherein the first amplification oligomer is a promoter primer or promoter provider further comprising a promoter sequence located 5' to the respective target hybridizing sequence.

Embodiment 176 is the method of embodiment 175, wherein the promoter sequence is a T7 promoter sequence.

Embodiment 177 is the method of embodiment 176, wherein the promoter sequence has the nucleotide sequence of residues 9-36 of SEQ ID NO: 15.

Embodiment 178 is the method of embodiment 175, wherein the first amplification oligomer comprises the nucleotide sequence of residues 9-52 of SEQ ID NO: 15.

Embodiment 179 is the method of embodiment 178, wherein the first amplification oligomer comprises the nucleotide sequence of SEQ ID NO:15.

Embodiment 180 is the method of any one of embodiments 172 to 179, further comprising purifying the *G. vaginalis* target nucleic acid, if present, from other components in the sample before step (2).

Embodiment 181 is the method of embodiment 180, wherein the purifying step comprises contacting the sample with at least one capture probe oligomer comprising a target-hybridizing sequence covalently attached to a sequence or moiety that binds to an immobilized probe, wherein the capture probe target-hybridizing sequence specifically hybridizes to a target sequence within the *G. vaginalis* target nucleic acid.

Embodiment 182 is the method of embodiment 181, wherein the capture probe target-hybridizing sequence substantially corresponds to the nucleotide sequence of residues 1-20 of SEQ ID NO: 13.

Embodiment 183 is the method of embodiment 182, wherein the capture probe oligomer comprises the nucleotide sequence of SEQ ID NO:13.

Embodiment 184 is the method of any one of embodiments 172 to 183, wherein the detecting step (3) comprises contacting the one or more amplification products with a detection probe comprising a target-hybridizing sequence that specifically hybridizes to the *G. vaginalis* target region, and detecting the presence or absence of any target-hybridized detection probe.

Embodiment 185 is the method of embodiment 184, wherein the detection probe target-hybridizing sequence substantially corresponds to the nucleotide sequence of residues 1-18 of SEQ ID NO: 16.

Embodiment 186 is the method of embodiment 185, wherein the detection probe target-hybridizing sequence comprises the nucleotide sequence of residues 1-18 of SEQ ID NO:16.

Embodiment 187 is the method of any one of embodiments 184 to 186, wherein the detection probe comprises a label.

Embodiment 188 is the method of embodiment 187, wherein the label is a chemiluminescent label or a fluorescent label.

Embodiment 189 is the method of embodiment 187, wherein the detecting step (3) occurs during the amplifying step (2).

Embodiment 190 is the method of embodiment 189, wherein each detection probe comprises a fluorescent label and a quencher.

Embodiment 191 is the method of embodiment 190, wherein each detection probe is a molecular torch, a molecular beacon, or a TaqMan detection probe.

Embodiment 192 is the method of any one of embodiments 184 to 186, wherein the detection probe further comprises a non-target-hybridizing sequence.

Embodiment 193 is the method of embodiment 192, wherein the detection probe is a molecular torch or a molecular beacon.

Embodiment 194 is the method of any one of embodiments 121 to 193, wherein the amplification reaction at step (2) is an isothermal amplification reaction.

Embodiment 195 is the method of embodiment 194, wherein the amplification reaction is a transcription-mediated amplification (TMA) reaction.

Embodiment 196 is the method of embodiment 194 or 195, wherein the amplification reaction is a real-time amplification reaction.

Definitions

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise.

The conjunction "or" is to be interpreted in the inclusive sense, i.e., as equivalent to "and/or," unless the inclusive sense would be unreasonable in the context.

The term "about" indicates insubstantial variation in a quantity of a component of a composition not having any significant effect on the activity or stability of the composition. In some embodiments, "about" encompasses variation within 10%, 5%, 2%, 1%, or 0.5% of a stated value.

All ranges are to be interpreted as encompassing the endpoints in the absence of express exclusions such as "not including the endpoints": thus, for example, "within 10-15" includes the values 10 and 15 as well as all integer and (where possible) non-integer values between the endpoints, e.g., 11, 11.5, 12 and one third, 4x, etc.

The terms "comprise," "comprises," "comprising," "contain," "contains," "containing," "include," "includes," and "including" are not intended to be limiting.

"Sample" includes any specimen that may contain *Lactobacillus* sp., Atopobium vaginae. or *Gardnerella vaginalis* or components thereof, such as nucleic acids or fragments of nucleic acids. Samples include "biological samples" which include any tissue or material derived from a living or dead human that may contain *Lactobacillus* sp., Atopobium vaginae. or *Gardnerella vaginalis* or components thereof (e.g., a target nucleic acid derived therefrom), including, e.g., vaginal swab samples, cervical brush samples, respiratory tissue or exudates such as bronchoscopy, bronchoalveolar lavage (BAL) or lung biopsy, sputum, saliva, peripheral blood, plasma, serum, lymph node, gastrointestinal tissue, feces, urine, semen or other body fluids or materials. The biological sample may be treated to physically or mechanically disrupt tissue or cell structure, thus releasing intracellular components into a solution which may further contain enzymes, buffers, salts, detergents and the like, which are used to prepare, using standard methods, a biological sample for analysis. Also, samples may include processed samples, such as those obtained from passing samples over or through a filtering device, or following centrifugation, or by adherence to a medium, matrix, or support.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see PCT No. WO 95/32305), phosphorothioate linkages, methylphosphonate linkages, or combinations thereof. Sugar moieties of the nucleic acid may be either ribose or deoxyribose, or similar compounds having known substitutions, e.g., 2' methoxy substitutions and 2' halide substitutions (e.g., 2'-F). Nitrogenous bases may be conventional bases (A, G, C, T, U), analogs thereof (e.g., inosine, 5-methylisocytosine, isoguanine: The Biochemistry of the Nucleic Acids 5-36, Adams et al., ed., 11th ed., 1992, Abraham et al., 2007, BioTechniques 43:617-24), which include derivatives of purine or pyrimidine bases (e.g., N+-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, 06-methylguanine, 4-thio-pyrimidines, 4-amino-pyrimidines, 4-dimethylhydrazine-pyrimidines, and 0+-alkyl-pyrimidines, and pyrazolo-compounds, such as unsubstituted or 3-substituted pyrazolo[3,4-d]pyrimidine: U.S. Pat. Nos. 5,378,825, 6,949,367 and PCT No. WO 93/13121). Nucleic acids may include "abasic" residues in which the backbone does not include a nitrogenous base for one or more residues (U.S. Pat. No. 5,585,481). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., Biochemistry 43:13233-41, 2004). Nucleic acids may include modified bases to alter the function or behavior of the nucleic acid, e.g., addition of a 3-terminal dideoxynucleotide to block additional nucleotides from being added to the nucleic acid. Synthetic methods for making nucleic acids in vitro are well-known in the art although nucleic acids may be purified from natural sources using routine techniques.

The term "polynucleotide," as used herein, denotes a nucleic acid chain. Throughout this application, nucleic acids are designated by the 5'-terminus to the 3'-terminus. Standard nucleic acids, e.g., DNA and RNA, are typically synthesized "5'-to-3"," i.e., by the addition of nucleotides to the 3'-terminus of a growing nucleic acid.

A "nucleotide," as used herein, is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me).

A "nucleic-acid-based detection assay," as used herein, is an assay for the detection of a target sequence within a target nucleic acid and utilizing one more oligonucleotides that specifically hybridize to the target sequence.

In certain embodiments in accordance with the present invention, a nucleic-acid-based detection assay is an "amplification-based assay," i.e., an assay that utilizes one or more steps for amplifying a nucleic acid target sequence. Various amplification methods for use in detection assays are known in the art, several of which are summarized further herein. For the sake of clarity, an amplification-based assay may include one or more steps that do not amplify a target sequence, such as, for example, steps used in non-amplification-based assay methods (e.g., a hybridization assay or a cleavage-based assay).

In other embodiments, a nucleic-acid-based detection assay is a "non-amplification-based assay," i.e., an assay that does not rely on any step for amplifying a nucleic acid target sequence. For the sake of clarity, a nucleic-acid-based detection assay that includes a reaction for extension of a primer in the absence of any corresponding downstream amplification oligomer (e.g., extension of a primer by a reverse transcriptase to generate an RNA: DNA duplex followed by an RNase digestion of the RNA, resulting in a single-stranded cDNA complementary to an RNA target but without generating copies of the cDNA) is understood to be a non-amplification-based assay.

An exemplary non-amplification-based assay is a "cleavage-based assay," which is an assay that relies on the specific cleavage, by a flap endonuclease, of a linear duplex cleavage structure formed by the specific hybridization of overlapping oligonucleotides to a target nucleic acid. In these assays, a probe oligonucleotide containing a non-target-hybridizing flap region is cleaved in an overlap-dependent manner by the flap endonuclease to release a cleavage product that is then detected. The principles of cleavage-based assays are well-known in the art, and exemplary assays are described in, for example, Lyamichev et al. (Nat. Biotechnol. 17:292-296, 1999), Ryan et al. (Mol. Diagn. 4:135-144, 1999), Allawi et al. (J. Clin. Microbiol. 44:3443-3447, 2006), U.S. Pat. Nos. 5,846,717 & 6,706,471 to Brow et al., and U.S. Pat. No. 5,614,402 to Dahlberg et al. Cleavage-based assays include, e.g., the commercially available Invader® assays (Hologic, Inc., Madison, WI).

A "target nucleic acid," as used herein, is a nucleic acid comprising a target sequence to be detected. Target nucleic acids may be DNA or RNA as described herein, and may be either single-stranded or double-stranded. The target nucleic acid may include other sequences besides the target sequence.

By "isolated" it is meant that a sample containing a target nucleic acid is taken from its natural milieu, but the term does not connote any degree of purification.

The term "target sequence," as used herein, refers to the particular nucleotide sequence of a target nucleic acid that is to be detected. The "target sequence" includes the complexing sequences to which oligonucleotides (e.g., probe oligonucleotide, priming oligonucleotides and/or promoter oligonucleotides) complex during a detection process (e.g., an amplification-based detection assay such as, for example, TMA or PCR, or a non-amplification-based detection assay such as, for example, a cleavage-based assay). Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands. In choosing a target sequence, the skilled artisan will understand that a "unique" sequence should be chosen so as to distinguish between unrelated or closely related target nucleic acids.

"Target-hybridizing sequence" is used herein to refer to the portion of an oligomer that is configured to hybridize with a target nucleic acid sequence. Preferably, the target-hybridizing sequences are configured to specifically hybridize with a target nucleic acid sequence. Target-hybridizing sequences may be 100% complementary to the portion of the target sequence to which they are configured to hybridize, but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid is a plurality strains within a species, such as would be the case for an oligomer configured to hybridize to the various strains of *Lactobacillus*. It is understood that other reasons exist for configuring a target-hybridizing sequence to have less than 100% complementarity to a target nucleic acid.

The term "targets a sequence," as used herein in reference to a region of *Lactobacillus* sp., *A. vaginae*. or *G. vaginalis* nucleic acid, refers to a process whereby an oligonucleotide hybridizes to the target sequence in a manner that allows for detection as described herein. In one embodiment, the oligonucleotide is complementary with the targeted *Lactobacillus* sp., *A. vaginae*. or *G. vaginalis* nucleic acid sequence and contains no mismatches. In another embodiment, the oligonucleotide is complementary but contains 1, 2, 3, 4, or 5 mismatches with the targeted *Lactobacillus* sp., *A. vaginae*. or *G. vaginalis* nucleic acid sequence. Preferably, the oligonucleotide that hybridizes to the target nucleic acid sequence includes at least 10 to as many as 50 nucleotides complementary to the target sequence. It is understood that at least 10 and as many as 50 is an inclusive range such that 10, 50 and each whole number there between are included. Preferably, the oligomer specifically hybridizes to the target sequence.

The term "configured to" denotes an actual arrangement of the polynucleotide sequence configuration of a referenced oligonucleotide target-hybridizing sequence. For example, oligonucleotides that are configured to specifically hybridize to a target sequence have a polynucleotide sequence that specifically hybridizes to the referenced sequence under stringent hybridization conditions.

The term "configured to specifically hybridize to" as used herein means that the target-hybridizing region of an oligonucleotide is designed to have a polynucleotide sequence that could target a sequence of the referenced *Lactobacillus* sp., *A. vaginae*. or *G. vaginalis* target region. Such an oligonucleotide is not limited to targeting that sequence only, but is rather useful as a composition, in a kit or in a method for targeting a *Lactobacillus* sp., *A. vaginae*. or *G. vaginalis* target nucleic acid. The oligonucleotide is designed to function as a component of an assay for detection of *Lactobacillus* sp., *A. vaginae*. or *G. vaginalis* from a sample, and therefore is designed to target *Lactobacillus* sp., *A. vaginae*. or *G. vaginalis* in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined. The term "configured to" denotes an actual arrangement of the polynucleotide sequence configuration of the oligonucleotide target-hybridizing sequence.

The term "fragment," as used herein in reference to an *Lactobacillus* sp., *A. vaginae*. or *G. vaginalis* targeted nucleic acid, refers to a piece of contiguous nucleic acid. In certain embodiments, the fragment includes contiguous nucleotides from an *Lactobacillus* sp., *A. vaginae*. or *G. vaginalis* 16S ribosomal RNA, wherein the number of 16S contiguous nucleotides in the fragment are less than that for the entire 16S.

The term "region," as used herein, refers to a portion of a nucleic acid wherein said portion is smaller than the entire nucleic acid. For example, when the nucleic acid in reference is an oligonucleotide promoter primer, the term "region" may be used refer to the smaller promoter portion of the entire oligonucleotide. Similarly, and also as example only, when the nucleic acid is a 16S ribosomal RNA, the term "region" may be used to refer to a smaller area of the nucleic acid, wherein the smaller area is targeted by one or more oligonucleotides of the invention. As another non-limiting example, when the nucleic acid in reference is an amplicon, the term region may be used to refer to the smaller nucleotide sequence identified for hybridization by the target-hybridizing sequence of a probe.

The interchangeable terms "oligomer," "oligo," and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources or may be synthesized using any of a variety of well-known enzymatic or chemical methods. The term oligonucleotide does not denote any particular function to the reagent: rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase: it may function as a primer and provide a promoter if it contains a sequence recognized by an RNA polymerase and allows for transcription (e.g., a T7 Primer); and it may function to detect a target nucleic acid if it is capable of hybridizing to the target nucleic acid, or an amplicon thereof, and further provides a detectible moiety (e.g., an acridinium-ester compound).

As used herein, an oligonucleotide "substantially corresponding to" a specified reference nucleic acid sequence means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from a reference sequence and still hybridize to the same target nucleic acid sequence. It is also understood that a first nucleic acid corresponding to a second nucleic acid includes the RNA and DNA thereof and includes the complements thereof, unless the context clearly dictates otherwise. This variation from the nucleic acid may be stated in terms of a percentage of identical bases within the sequence or the percentage of perfectly complementary bases between the probe or primer and its target sequence. Thus, in certain embodiments, an oligonucleotide "substantially corresponds" to a reference nucleic acid sequence if these percentages of base identity or complementarity are from 100% to about 80%. In preferred embodiments, the percentage is from 100% to about 85%. In more preferred embodiments, this percentage is from 100% to about 90%; in other preferred embodiments, this percentage is from 100% to about 95%. Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

An "amplification oligomer" is an oligomer, at least the 3'-end of which is complementary to a target nucleic acid, and which hybridizes to a target nucleic acid, or its complement, and participates in a nucleic acid amplification reaction. An example of an amplification oligomer is a "primer" that hybridizes to a target nucleic acid and contains a 3" OH end that is extended by a polymerase in an amplification process. Another example of an amplification oligomer is an oligomer that is not extended by a polymerase (e.g., because it has a 3' blocked end) but participates in or facilitates amplification. For example, the 5' region of an amplification oligonucleotide may include a promoter sequence that is non-complementary to the target nucleic acid (which may be referred to as a "promoter primer" or "promoter provider"). Those skilled in the art will understand that an amplification oligomer that functions as a primer may be modified to include a 5' promoter sequence, and thus function as a promoter primer. Incorporating a 3' blocked end further modifies the promoter primer, which is now capable of hybridizing to a target nucleic acid and providing an upstream promoter sequence that serves to initiate transcription, but does not provide a primer for oligo extension. Such a modified oligo is referred to herein as a "promoter provider" oligomer. Size ranges for amplification oligonucleotides include those that are about 10 to about 70 nt long (not including any promoter sequence or poly-A tails) and contain at least about 10 contiguous bases, or even at least 12 contiguous bases that are complementary to a region of the target nucleic acid sequence (or a complementary strand thereof). The contiguous bases are at least 80%, or at least 90%, or completely complementary to the target sequence to which the amplification oligomer binds. An amplification oligomer may optionally include modified nucleotides or analogs, or additional nucleotides that participate in an amplification reaction but are not complementary to or contained in the target nucleic acid, or template sequence. For example, an amplification oligomer may contain additional nucleotides at its 5' end, complementary to its 3' end, for the purpose forming hairpins to modulate priming efficiency (e.g., a promoter primer may contain additional nucleotides upstream of the promoter sequence for this purpose). It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24 & 25).

As used herein, a "promoter" is a specific nucleic acid sequence that is recognized by a DNA-dependent RNA polymerase ("transcriptase") as a signal to bind to the nucleic acid and begin the transcription of RNA at a specific site.

As used herein, a "promoter provider" or "provider" refers to an oligonucleotide comprising first and second regions, and which is modified to prevent the initiation of DNA synthesis from its 3'-terminus. The "first region" of a promoter provider oligonucleotide comprises a base sequence which hybridizes to a DNA template, where the hybridizing sequence is situated 3", but not necessarily adjacent to, a promoter region. The hybridizing portion of a promoter oligonucleotide is typically at least 10 nucleotides in length, and may extend up to 50 or more nucleotides in length. The "second region" comprises a promoter sequence for an RNA polymerase. A promoter oligonucleotide is engineered so that it is incapable of being extended by an RNA- or DNA-dependent DNA polymerase, e.g., reverse transcriptase, preferably comprising a blocking moiety at its 3'-terminus as described above. As referred to herein, a "T7 Provider" is a blocked promoter provider oligonucleotide that provides an oligonucleotide sequence that is recognized by T7 RNA polymerase.

"Amplification" refers to any known procedure for obtaining multiple copies of a target nucleic acid sequence or its complement or fragments thereof. The multiple copies may be referred to as amplicons or amplification products. Known amplification methods include both thermal cycling and isothermal amplification methods. In some embodiments, isothermal amplification methods are preferred. Replicase-mediated amplification, polymerase chain reaction (PCR), ligase chain reaction (LCR), strand-displacement amplification (SDA), and transcription-mediated or transcription-associated amplification are non-limiting examples of nucleic acid amplification methods. Replicase-mediated amplification uses self-replicating RNA molecules, and a replicase such as QB-replicase (e.g., U.S. Pat. No. 4,786,600). PCR amplification uses a DNA polymerase, pairs of primers, and thermal cycling to synthesize multiple copies of two complementary strands of dsDNA or from a cDNA (e.g., U.S. Pat. Nos. 4,683,195, 4,683,202, and 4,800, 159). LCR amplification uses four or more different oligonucleotides to amplify a target and its complementary strand by using multiple cycles of hybridization, ligation, and denaturation (e.g., U.S. Pat. Nos. 5,427,930 and 5,516,663). SDA uses a primer that contains a recognition site for a restriction endonuclease and an endonuclease that nicks one strand of a hemimodified DNA duplex that includes the target sequence, whereby amplification occurs in a series of primer extension and strand displacement steps (e.g., U.S. Pat. Nos. 5,422,252: 5,547,861; and 5,648,211). Preferred embodiments use an amplification method suitable for the amplification of RNA target nucleic acids, such as transcription-mediated amplification (TMA) or NASBA, but it will be apparent to persons of ordinary skill in the art that oligomers disclosed herein may be readily used as primers in other amplification methods.

"Transcription-associated amplification," also referred to herein as "transcription-mediated amplification" (TMA), refers to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. TMA methods are embodiments of amplification methods used for amplifying and detecting target sequences as described herein. Variations of transcription-associated amplification are well-known in the art as previously disclosed in detail (e.g., US Pat. Nos. 4,868,105; 5,124,246; 5,130,238; 5,399,491; 5,437,990; 5,554,516; and 7,374,885; and PCT Pub. Nos. WO 88/01302, WO 88/10315, and WO 95/03430). The person of ordinary skill in the art will appreciate that the disclosed compositions may be used in amplification methods based on extension of oligomer sequences by a polymerase.

As used herein, the term "real-time TMA" refers to transcription-mediated amplification ("TMA") of target nucleic acid that is monitored by real-time detection means.

The term "amplicon," which is used interchangeably with "amplification product," refers to the nucleic acid molecule generated during an amplification procedure that is complementary or homologous to a sequence contained within the target sequence. These terms can be used to refer to a single strand amplification product, a double strand amplification product or one of the strands of a double strand amplification product.

"Probe," "detection probe," "detection oligonucleotide," and "detection probe oligomer" are used interchangeably herein to refer to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Probes may be DNA, RNA, analogs thereof or combinations thereof and they may be labeled or unlabeled. A probe's "target sequence" generally refers to a smaller nucleic acid sequence within a larger nucleic acid sequence that hybridizes specifically to at least a portion of a probe oligomer by standard base pairing. A probe may comprise target-specific sequences and other sequences that contribute to the three-dimensional conformation of the probe (e.g., U.S. Pat. Nos. 5,118,801; 5,312,728; 6,849,412; 6,835,542; 6,534,274; and 6,361,945; and US Pub. No. 20060068417). In a preferred embodiment, the detection probe comprises a 2' methoxy backbone which can result in a higher signal being obtained.

The term "TaqManR probe" refers to detection oligonucleotides that contain a fluorescent dye, typically on the 5' base, and a non-fluorescent quenching dye (quencher), typically on the 3' base. When irradiated, the excited fluorescent dye transfers energy to the nearby quenching dye molecule rather than fluorescing, resulting in a non-fluorescent substrate. During amplification, the exonuclease activity of the polymerase cleaves the TaqMan probe to separate the fluorophore from the quencher, thereby allowing an unquenched signal to be emitted from the fluorophore as an indicator of amplification.

As used herein, a "label" refers to a moiety or compound joined directly or indirectly to a probe that is detected or leads to a detectable signal. Direct labelling can occur through bonds or interactions that link the label to the probe, including covalent bonds or non-covalent interactions, e.g., hydrogen bonds, hydrophobic and ionic interactions, or formation of chelates or coordination complexes. Indirect labelling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (e.g., U.S. Pat. Nos. 5,283,174, 5,656,207, and 5,658,737). Labels include chemiluminescent compounds, e.g., acridinium ester ("AE") compounds that include standard AE and derivatives (e.g., U.S. Pat. Nos. 5,656,207, 5,658,737, and 5,639,604). Synthesis and methods of attaching labels to nucleic acids and detecting labels are well known (e.g., Sambrook et al., Molecular Cloning. A Laboratory Manual, 2nd ed. (Cold Spring Harbor Laboratory Press, Cold Spring Harbor, NY, 1989), Chapter 10; U.S. Pat. Nos. 5,658,737, 5,656,207, 5,547,842, 5,283,174, and 4,581,333). More than one label, and more than one type of label, may be present on a particular probe, or detection may use a mixture of probes in which each probe is labeled with a compound that produces a detectable signal (e.g., U.S. Pat. Nos. 6,180,340 and 6,350,579).

As used herein, structures referred to as "molecular torches" are designed to include distinct regions of self-complementarity ("the closing domain") which are connected by a joining region ("the target binding domain") and which hybridize to one another under predetermined hybridization assay conditions. All or part of the nucleotide sequences comprising target closing domains may also function as target binding domains. Thus, target closing sequences can include, target binding sequences, non-target binding sequences, and combinations thereof.

"Capture probe," "capture oligonucleotide." "target capture oligonucleotide," and "capture probe oligomer" are used interchangeably herein to refer to a nucleic acid oligomer that specifically hybridizes to a target sequence in a target nucleic acid by standard base pairing and joins to a binding partner on an immobilized probe to capture the target nucleic acid to a support. One example of a capture oligomer includes an oligonucleotide comprising two binding regions: a target hybridizing sequence and an immobilized probe-binding region. A variation of this example, the two regions may be present on two different oligomers joined together by one or more linkers. Another embodiment of a capture oligomer the target hybridizing sequence is a sequence that includes random or non-random poly-GU, poly-GT, or poly U sequences to bind non-specifically to a target nucleic acid and link it to an immobilized probe on a support (see. e.g., PCT Pub No. WO 2008/016988). The immobilized probe binding region can be a nucleic acid sequence, referred to as a tail. Tails include a substantially homopolymeric tail of about 10 to 40 nucleotides (e.g., Aio to A40), or of about 14 to 33 nt (e.g., T3A14 to T3A30), that bind to a complementary immobilized sequence attached to the support particle or support matrix. Thus, a non-limiting example of preferred nucleic acid tails can in some embodiments include To4A1040 sequences. Another example of a capture oligomer comprises two regions, a target hybridizing sequence and a binding pair member that is not a nucleic acid sequence.

As used herein, an "immobilized oligonucleotide," "immobilized probe" or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size+ 5%), to which an immobilized probe is joined directly (via covalent linkage, chelation, or ionic interaction), or indirectly (via one or more linkers), where the linkage or interaction between the probe and support is stable during hybridization conditions.

DESCRIPTION OF THE INVENTION

The present invention is generally directed to methods and compositions for determining the presence or absence of select bacterial organisms in a sample. In some embodiments, the present invention provides methods and compositions for diagnosing Bacterial Vaginosis (BV) in a subject. In other, non-mutually exclusive embodiments, the present invention provides methods for the detection of any one or more of *Lactobacillus* sp., A. vaginae, and *G. vaginalis* in a sample, where the method includes performing amplification-based detection of a 16S rRNA target nucleic acid from one or more of *Lactobacillus* sp., A. vaginae, and *G. vaginalis*. The present invention further provides compositions (including reaction mixtures) and kits comprising a combination of oligomers for detecting any one or more of *Lactobacillus* sp., A. vaginae, and *G. vaginalis*. The oligomer combination generally includes at least two amplification oligomers for detecting one or more of *Lactobacillus* sp., A. vaginae, and *G. vaginalis* in a sample, and may further include one or more additional oligomers as described herein for performing amplification-based detection of *Lactobacillus* sp., A. vaginae, and *G. vaginalis* such as, e.g., a capture probe and/or a detection probe.

The methods for diagnosing BV generally include detecting the presence or absence of one or more of *Lactobacillus* sp., A. vaginae, and *G. vaginalis* in a sample from a subject suspected of having BV. In particular, an assay is performed for the specific detection in the sample of each of *Lactobacillus* sp., A. vaginae, and *G. vaginalis*. Based on the results of the detection assay, a quantitative value is assigned for each of *Lactobacillus* sp., A. vaginae, and *G. vaginalis*, and a single BV score is then determined using these quantitative values. The presence or absence of BV is then determined based on a comparison of the BV score to a cutoff value, which is typically predetermined. Generally, if a BV score above the cutoff value indicates a BV positive state and quantitative values are in units of LogCopies, then BV score determination includes subtracting the *Lactobacillus* sp. quantitative value from the greater of the A. vaginae and the *G. vaginalis* values. Determination of the cutoff value may be based on predictive modeling using results from a cohort of clinical specimens. A cutoff value could be selected in order to maximize agreement or target a rate of clinical sensitivity or specificity relative to the BV patient infected status as established by a clinical reference method (e.g., Nugent score with intermediates resolved by Amsel's criteria). In some embodiments, a minimum quatitative value is imposed for *Lactobacillus* sp. and/or for A. vaginae and *G. vaginalis*, whereby if a quantitative value measured by the detection assay is less than the respective imposed minimum value, the minimum value is used as the quantitative value for determining the BV score.

Quatitative values for *Lactobacillus* sp., A. vaginae, and/or *G. vaginalis* may also be standardized and/or weighted. For example, standardization may be used to balance the likelihood of each of the A. vaginae and *G. vaginalis* quantitative values participating in the BV score calculation, since the BV score determination utilizes only the maximum of these two values and observed *G. vaginalis* concentrations trend higher that A. vaginae concentrations in a population of clinical specimens. In some variations, standardization includes adjusting a quantitative value measured by the detection assay by a population statistic such as, e.g., a population median value (for example, dividing a concentration in units of copies by a population median or, where the quantitative data are in units of log copies, subtracting the median log copies value). Weighting can be used to influence the impact of changes in the value of a term (e.g., *Lactobacillus* sp. quantitative value, A.vaginae or G.vaginalis quantitative value, or the quantitative value of another term in the prediction formula) on the value of the score. A higher weight could increase the impact of changes in a term's value on the score, while a lower rate can decrease this impact.

An equation for calculation of the BV score may further include additional terms. In some variations, calculation of the BV score further include adding or subtracting an adjustment constant to adjust for a desired cutoff value (e.g., a cutoff value of zero). In some variations, calculation of the BV score further includes adding an internal control (IC) adjustment factor, which may be used to compensate for sample inhibition in the detection assay. Particularly suitable IC adjustment factors are based on a ratio of an observed IC value generated from the detection assay to an expected IC value for the detection assay.

In specific variations of a method for diagnosing BV, the BV score is assigned using the following equation:

BV score=$C_0$+$W_L$Max ($L_S$, $F_{LS}$)+$W_{GA}$Max (As, Gs, $F_{GAS}$)+$W_{IC}$ Log 2 (ICRatio), where the equation elements are as described in Table 1.

TABLE 1

| Equation Element | Description |
|---|---|
| $C_0$ | Adjustment constant |
| $W_L$ | Weighting constant for *Lactobacillus* sp. |
| Max($L_S$, $F_{LS}$) | Greater of $L_S$ and $F_{LS}$ |
| $L_S$ | Observed quantitative value for *Lactobacillus* sp. (standardized) |
| $F_{LS}$ | Imposed minimum quantitative value for *Lactobacillus* sp. (standardized) |
| $W_{GA}$ | Weighting constant for *A. vaginae* and *G. vaginalis* |
| Max($A_S$, $G_S$, $F_{GAS}$) | Greater of $A_S$, $G_S$, and $F_{GAS}$ |
| $A_S$ | Observed quantitative value for *A. vaginae* (standardized) |
| $G_S$ | Observed quantitative value for *G. vaginalis* (standardized) |

TABLE 1-continued

| Equation Element | Description |
| --- | --- |
| $F_{GAS}$ | Imposed minimum quantitative value for *A. vaginae* and *G. vaginalis* (standardized) |
| $W_{IC}$ | Internal control (IC) weighting constant |
| ICRatio | Ratio of an observed internal control (IC) value generated from the detection assay to an expected IC value for the detection assay |

In some specific embodiments of a method for diagnosing BV in which the BV score is determined by the above equation, the imposed minimum value for the A. vaginalis/ G. vaginalis term (FGA) is set to zero (0) prior to standardization.

While *Lactobacillus* sp., A. vaginae, and *G. vaginalis* may be detected using any suitable method, it is presently preferred that these bacteria are detected using a nucleic-acid-based detection assay. Nucleic-acid-based detection assays in accordance with the present invention generally utilize oligonucleotides that specifically hybridize to a target nucleic acid of *Lactobacillus* sp., A. vaginae, or *G. vaginalis* with minimal cross-reactivity to other nucleic acids suspected of being in a sample. Accordingly, oligonucleotides for nucleic-acid-based detection of the select species of *Lactobacillus* sp., A. vaginae, or *G. vaginalis* will have minimal cross-reactivity to species within other bacterial genera, including, for example, *Trichomonas* sp.: *Trichomonas vaginalis*: *Candida* sp.: Bacterium from the order Clostridiales: *Clostridium*-like sp.: *Eggerthella* sp.: Enterobacteria: *Peptostreptococcus* micros: *Aerococcus christensenii*: Leptotrichia amnionii: Peptoniphilus sp.: Dialister sp.: *Mycoplasma hominis*: Sneathia sanguinegens: Anaerococcus tetradius: Mobiluncus sp.: Mobiluncus hominis: Megasphaera sp.: *Prevotella* sp.: Leptotrichia sanguinegens; and *Finegoldia magna*. In one aspect, a nucleic-acid-based detection assay in accordance with the present invention further includes components for detecting one of more of these organisms, or other bacterial genera associated with BV.

In particular embodiments, a nucleic-acid-based detection assay targets the 16S rRNA of *Lactobacillus* sp., A. vaginae, and/or G. vaginalis, or a gene encoding the 16S rRNA. Particularly suitable target regions of the 16S rRNA or the encoding gene are (i) a L. crispatus 16S rRNA region corresponding to a region of SEQ ID NO: 1 from about nucleotide position 40 to about nucleotide position 265: (ii) a L. jensenii 16S IRNA region corresponding to a region of SEQ ID NO:2 from about nucleotide position 43 to about nucleotide position 247: (iii) a L. gasseri 16S rRNA region corresponding to a region of SEQ ID NO: 3 from about nucleotide position 93 to about nucleotide position 298: (iv) a A. vaginae 16S IRNA region corresponding to a region of SEQ ID NO:4 from about nucleotide position 540 to about nucleotide position 625; and (v) a G. vaginalis 16S rRNA region corresponding to a region of SEQ ID NO:5 from about nucleotide position 172 to about nucleotide position 227. In specific variations of a nucleic-acid-based detection assay targeting a 16S rRNA region as above, (a) a *Lactobacillus*-specific oligonucleotide includes a target-hybridizing region comprising a sequence substantially corresponding to the sequence of SEQ ID NO:7, a sequence substantially corresponding to the sequence of SEQ ID NO:8, a sequence substantially corresponding to the sequence of SEQ ID NO:9, a sequence substantially corresponding to the sequence of residues 28-45 of SEQ ID NO: 10, a sequence substantially corresponding to the sequence of residues 1-17 of SEQ ID NO: 11, or a sequence substantially corresponding to the sequence of residues 7-23 of SEQ ID NO: 12: (b) a A. vaginae-specific oligonucleotide includes a target-hybridizing region comprising a sequence substantially corresponding to the sequence of SEQ ID NO: 17, a sequence substantially corresponding to the sequence of residues 28-45 of SEQ ID NO: 18, or a sequence substantially corresponding to the sequence of residues 6-21 of SEQ ID NO: 19, and/or (c) a G. vaginalis-specific oligonucleotide includes a target-hybridizing region comprising a sequence substantially corresponding to the sequence of SEQ ID NO: 14, a sequence substantially corresponding to the sequence of residues 36-52 of SEQ ID NO: 15, or a sequence substantially corresponding to the sequence of residues 1-18 of SEQ ID NO: 16. In some such embodiments, (a) a *Lactobacillus*-specific oligonucleotide includes a target-hybridizing region comprising or consisting of the sequence of SEQ ID NO:7, the sequence of SEQ ID NO:8, the sequence of SEQ ID NO:9, the sequence of residues 28-45 of SEQ ID NO: 10, the sequence of residues 1-17 of SEQ ID NO: 11, or the sequence of residues 7-23 of SEQ ID NO: 12: (b) a A. vaginae-specific oligonucleotide includes a target-hybridizing region comprising or consisting of the sequence of SEQ ID NO: 17, the sequence of residues 28-45 of SEQ ID NO: 18, or the sequence of residues 6-21 of SEQ ID NO: 19, and/or (c) a G. vaginalis-specific oligonucleotide includes a target-hybridizing region comprising or consisting of the sequence of SEQ ID NO: 14, the sequence of residues 36-52 of SEQ ID NO: 15, or the sequence of residues 1-18 of SEQ ID NO: 16. In certain embodiments, a nucleic-acid-based detection assay utilizes at least two or three *Lactobacillus*-specific oligonucleotides, at least two or three A. vaginae-specific oligonucleotides, and/or at least two or three G. vaginalis-specific oligonucleotides, which may be oligonucleotides selected from those specified above.

In some embodiments of a method comprising the use of a nucleic-acid-base detection assay, an amplification-based assay is used to detect *Lactobacillus* sp., A. vaginae, and/or G. vaginalis. Such variations generally include amplifying a target sequence within a bacterial target nucleic acid utilizing an in vitro nucleic acid amplification reaction and detecting the amplified product by, for example, specifically hybridizing the amplified product with a nucleic acid detection probe that provides a signal to indicate the presence of a bacterial target in the sample. The amplification step includes contacting the sample with two or more amplification oligomers specific for a target sequence in a target nucleic acid (e.g., a target sequence in a 16S rRNA) to produce an amplified product if the target nucleic acid is present in the sample. Amplification synthesizes additional copies of the target sequence or its complement such as, e.g., by using at least one nucleic acid polymerase to extend the sequence from an amplification oligomer (a primer) using a template strand. One embodiment for detecting the amplified product uses a hybridizing step that includes contacting the amplified product with at least one probe specific for a sequence amplified by the selected amplification oligomers, e.g., a sequence contained in the target sequence flanked by a pair of selected amplification oligomers. Suitable amplification methods include, for example, replicase-mediated amplification, polymerase chain reaction (PCR), ligase chain reaction (LCR), strand-displacement amplification (SDA), and transcription-mediated or transcription-associated amplification (TMA). Such amplification methods are well-known in the art (see. e.g., discussion of amplification methods in Definitions section, supra) and are readily used in accordance with the methods of the present invention.

For example, some amplification methods that use TMA amplification include the following steps. Briefly, the target nucleic acid that contains the sequence to be amplified is provided as single stranded nucleic acid (e.g., ssRNA or ssDNA). Those skilled in the art will appreciate that conventional melting of double stranded nucleic acid (e.g., dsDNA) may be used to provide single-stranded target nucleic acids. A promoter primer binds specifically to the target nucleic acid at its target sequence and a reverse transcriptase (RT) extends the 3" end of the promoter primer using the target strand as a template to create a cDNA copy of the target sequence strand, resulting in an RNA: DNA duplex. An RNase digests the RNA strand of the RNA: DNA duplex and a second primer binds specifically to its target sequence, which is located on the cDNA strand downstream from the promoter primer end. RT synthesizes a new DNA strand by extending the 3' end of the second primer using the first cDNA template to create a dsDNA that contains a functional promoter sequence. An RNA polymerase specific for the promoter sequence then initiates transcription to produce RNA transcripts that are about 100 to 1000 amplified copies ("amplicons") of the initial target strand in the reaction. Amplification continues when the second primer binds specifically to its target sequence in each of the amplicons and RT creates a DNA copy from the amplicon RNA template to produce an RNA: DNA duplex. RNase in the reaction mixture digests the amplicon RNA from the RNA: DNA duplex and the promoter primer binds specifically to its complementary sequence in the newly synthesized DNA. RT extends the 3' end of the promoter primer to create a dsDNA that contains a functional promoter to which the RNA polymerase binds to transcribe additional amplicons that are complementary to the target strand. The autocatalytic cycles of making more amplicon copies repeat during the course of the reaction resulting in about a billion-fold amplification of the target nucleic acid present in the sample. The amplified products may be detected in real-time during amplification, or at the end of the amplification reaction by using a probe that binds specifically to a target sequence contained in the amplified products. Detection of a signal resulting from the bound probes indicates the presence of the target nucleic acid in the sample.

In some embodiments, the method utilizes a "reverse" TMA reaction. In such variations, the initial or "forward" amplification oligomer is a priming oligonucleotide that hybridizes to the target nucleic acid in the vicinity of the 3'-end of the target region. A reverse transcriptase (RT) synthesizes a cDNA strand by extending the 3'-end of the primer using the target nucleic acid as a template. The second or "reverse" amplification oligomer is a promoter primer or promoter provider having a target-hybridizing sequence configure to hybridize to a target-sequence contained within the synthesized cDNA strand. Where the second amplification oligomer is a promoter primer, RT extends the 3' end of the promoter primer using the cDNA strand as a template to create a second, cDNA copy of the target sequence strand, thereby creating a dsDNA that contains a functional promoter sequence. Amplification then continues essentially as described above for initiation of transcription from the promoter sequence utilizing an RNA polymerase. Alternatively, where the second amplification oligomer is a promoter provider, a terminating oligonucleotide, which hybridizes to a target sequence that is in the vicinity to the 5'-end of the target region, is typically utilized to terminate extension of the priming oligomer at the 3'-end of the terminating oligonucleotide, thereby providing a defined 3'-end for the initial cDNA strand synthesized by extension from the priming oligomer. The target-hybridizing sequence of the promoter provider then hybridizes to the defined 3'-end of the initial cDNA strand, and the 3'-end of the cDNA strand is extended to add sequence complementary to the promoter sequence of the promoter provider, resulting in the formation of a double-stranded promoter sequence. The initial cDNA strand is then used as a template to transcribe multiple RNA transcripts complementary to the initial cDNA strand, not including the promoter portion, using an RNA polymerase that recognizes the double-stranded promoter and initiates transcription therefrom. Each of these RNA transcripts is then available to serve as a template for further amplification from the first priming amplification oligomer.

In certain embodiments comprising an amplification-based detection assay, a combination of at least two amplification oligomers is utilized for the detection of a *Lactobacillus* sp. 16S rRNA or a gene encoding a *Lactobacillus* sp. 16S rRNA. The oligomer combination may include first and second amplification oligomers for amplifying a L. crispatus 16S rRNA region corresponding to a region of SEQ ID NO: 1 from about nucleotide position 40 to about nucleotide position 265, a L. *jensenii* 16S rRNA region corresponding to a region of SEQ ID NO:2 from about nucleotide position 43 to about nucleotide position 247, and/or a L. gasseri 16S rRNA region corresponding to a region of SEQ ID NO:3 from about nucleotide position 93 to about nucleotide position 298. For example, in some embodiments, the first amplification oligomer includes a target-hybridizing sequence substantially corresponding to the nucleotide sequence of residues 28-45 of SEQ ID NO:10 and the second amplification oligomer includes a target-hybridizing sequence substantially corresponding to the nucleotide of SEQ ID NO:7. SEQ ID NO:8, or SEQ ID NO:9: in some such variations, the first amplification oligomer includes a target-hybridizing sequence substantially corresponding to the nucleotide sequence of residues 28-45 of SEQ ID NO: 10, the second amplification oligomer includes a target-hybridizing sequence substantially corresponding to the nucleotide sequence of SEQ ID NO:7, and the oligomer combination further includes third and fourth amplification oligomers, where the third amplification oligomer includes a target-hybridizing sequence substantially corresponding to the nucleotide sequence of SEQ ID NO: 8 and the fourth amplification oligomer includes a target-hybridizing sequence substantially corresponding to the nucleotide sequence of SEQ ID NO:9. In more particular variations, the first amplification oligomer includes a target-hybridizing sequence comprising or consisting of the nucleotide sequence of residues 28-45 of SEQ ID NO: 10 and the second amplification oligomer includes a target-hybridizing comprising or consisting of the nucleotide sequence of SEQ ID NO:7. SEQ ID NO:8, or SEQ ID NO:9; in some such embodiments, the first amplification oligomer includes a target-hybridizing sequence substantially corresponding to the nucleotide sequence of residues 28-45 of SEQ ID NO:10, the second amplification oligomer includes a target-hybridizing sequence substantially corresponding to the nucleotide sequence of SEQ ID NO:7, and the oligomer combination further includes a third and fourth amplification oligomers, wherein the third amplification oligomer includes a target-hybridizing sequence comprising or consisting of the nucleotide sequence of SEQ ID NO:8 and the fourth amplification oligomer includes a target-hybridizing sequence comprising or consisting of the nucleotide sequence of SEQ ID NO:9. In some embodiments as above, at least one amplification oligomer is a promoter primer or promoter provider further comprising a promoter sequence located 5' to the respective target-hybridizing sequence (e.g., a T7 promoter sequences such as, for example, the nucleotide sequence of residues 1-27 of SEQ ID NO: 10); in some such embodiments, the first amplification oligomer is a promoter primer or promoter provider. In more specific variations, the first amplification oligomer consists of the nucleotide sequence of SEQ ID NO: 10 and the second amplification oligomer consists of the nucleotide sequence of SEQ ID NO: 7. SEQ ID NO:8, or SEQ ID NO:9; in some such embodiments, the first amplification oligomer consists of the nucleotide sequence of SEQ ID NO:10 and the second amplification oligomer consists of the nucleotide sequence of SEQ ID NO:7, and the oligomer combination further includes third and fourth amplification oligomers, where the third amplification oligomer consists of the nucleotide sequence of SEQ ID NO:8 and the fourth amplification oligomer consists of the nucleotide sequence of SEQ ID NO:9.

In certain embodiments comprising an amplification-based detection assay, a combination of at least two amplification oligomers is utilized for the detection of a A. vaginae 16S rRNA or a gene encoding a A. vaginae 16S rRNA. The oligomer combination may include first and second amplification oligomers for amplifying a A. vaginae nucleic acid target region corresponding to a region of SEQ ID NO:4 from about nucleotide position 540) to about nucleotide position 625. For example, in some embodiments, the first amplification oligomer includes a target-hybridizing sequence substantially corresponding to the nucleotide sequence of SEQ ID NO: 17 and/or the second amplification oligomer includes a target-hybridizing sequence substantially corresponding to the nucleotide sequence of residues 28-45 of SEQ ID NO:18. In more particular variations, the first amplification oligomer includes a target-hybridizing sequence comprising or consisting of the nucleotide sequence of SEQ ID NO: 17 and/or the second amplification oligomer includes a target-hybridizing sequence comprising or consisting of the nucleotide sequence of residues 28-45 of SEQ ID NO:18. In some embodiments as above, at least one amplification oligomer is a promoter primer or promoter provider further comprising a promoter sequence located 5' to the respective target-hybridizing sequence (e.g., a T7 promoter sequences such as, for example, the nucleotide sequence of residues 1-27 of SEQ ID NO: 18): in some such embodiments, the first amplification oligomer is a promoter primer or promoter provider. In more specific variations, the first amplification oligomer consists of the nucleotide sequence of SEQ ID NO: 17 and/or the second amplification oligomer consists of the nucleotide sequence of SEQ ID NO: 18.

In certain embodiments comprising an amplification-based detection assay, a combination of at least two amplification oligomers is utilized for the detection of a G. vaginalis 16S rRNA or a gene encoding a G. vaginalis 16S IRNA. The oligomer combination may include first and second amplification oligomers for amplifying a G. vaginalis nucleic acid target region corresponding to a region of SEQ ID NO:5 from about nucleotide position 172 to about nucleotide position 227. For example, in some embodiments, the first amplification oligomer includes a target-hybridizing sequence substantially corresponding to the nucleotide sequence of SEQ ID NO: 14 and/or the second amplification oligomer includes a target-hybridizing sequence substantially corresponding to the nucleotide sequence of residues 36-52 of SEQ ID NO: 15. In more particular variations, the first amplification oligomer includes a target-hybridizing sequence comprising or consisting of the nucleotide sequence of SEQ ID NO: 14 and/or the second amplification oligomer includes a target-hybridizing sequence comprising or consisting of the nucleotide sequence of residues 36-52 of SEQ ID NO: 15. In some embodiments as above, at least one amplification oligomer is a promoter primer or promoter provider further comprising a promoter sequence located 5' to the respective target-hybridizing sequence (e.g., a T7 promoter sequences such as, for example, the nucleotide sequence of residues 9-35 of SEQ ID NO: 15): in some such embodiments, the first amplification oligomer is a promoter primer or promoter provider. In more specific variations, the first amplification oligomer consists of the nucleotide sequence of SEQ ID NO:14 and/or the second amplification oligomer comprises the nucleotide sequence of residues 9-52 of SEQ ID NO: 15 (e.g., the second amplification oligomer consists of the nucleotide sequence of SEQ ID NO: 15).

Detection of the amplified products may be accomplished by a variety of methods to detect a signal specifically associated with the amplified target sequence. The nucleic acids may be associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid detection probes that are configured to specifically hybridize to a sequence in the amplified product and detecting the presence of the probe: product complex, or by using a complex of probes that may amplify the detectable signal associated with the amplified products (e.g., U.S. Pat. Nos. 5,424,413; 5,451, 503; and 5,849,481: each incorporated by reference herein). Directly or indirectly labeled probes that specifically associate with the amplified product provide a detectable signal that indicates the presence of the target nucleic acid in the sample. For example, if the target nucleic acid is the 16S rRNA of *Lactobacillus* sp., A. vaginae, and/or *G. vaginalis*, the amplified product will contain a target sequence in or complementary to a sequence in the 16S rRNA, and a probe will bind directly or indirectly to a sequence contained in the amplified product to indicate the presence of the 16S rRNA of *Lactobacillus* sp., A. vaginae, and/or *G. vaginalis* in the tested sample.

Detection probes that hybridize to the complementary amplified sequences may be DNA or RNA oligomers, or oligomers that contain a combination of DNA and RNA nucleotides, or oligomers synthesized with a modified backbone, e.g., an oligomer that includes one or more 2'-methoxy substituted ribonucleotides. Probes used for detection of the amplified sequences may be unlabeled and detected indirectly (e.g., by binding of another binding partner to a moiety on the probe) or may be labeled with a variety of detectable labels. In some embodiments of the method for diagnosing BV, such as in certain embodiments using transcription-mediated amplification (TMA), the detection probe is a linear chemiluminescently labeled probe such as, e.g., a linear acridinium ester (AE) labeled probe.

The detection step may also provide additional information on the amplified sequence, such as, e.g., all or a portion of its nucleic acid base sequence. Detection may be performed after the amplification reaction is completed, or may be performed simultaneously with amplifying the target region, e.g., in real time. In one embodiment, the detection step allows homogeneous detection, e.g., detection of the hybridized probe without removal of unhybridized probe from the mixture (see. e.g., U.S. Pat. Nos. 5,639,604 and 5,283,174, each incorporated by reference herein).

In embodiments that detect the amplified product near or at the end of the amplification step, a linear detection probe may be used to provide a signal to indicate hybridization of the probe to the amplified product. One example of such detection uses a luminescently labeled probe that hybridizes to target nucleic acid. Luminescent label is then hydrolyzed from non-hybridized probe. Detection is performed by chemiluminescence using a luminometer. (see, e.g., International Patent Application Pub. No. WO 89/002476, incorporated by reference herein). In other embodiments that use real-time detection, the detection probe may be a hairpin probe such as, for example, a molecular beacon, molecular torch, or hybridization switch probe that is labeled with a reporter moiety that is detected when the probe binds to amplified product. Such probes may comprise target-hybridizing sequences and non-target-hybridizing sequences. Various forms of such probes have been described previously (see. e.g., U.S. Pat. Nos. 5,118,801; 5,312,728; 5,925,517; 6,150,097; 6,849,412; 6,835,542; 6,534,274; and 6,361,945; and US Patent Application Pub. Nos. 20060068417A1 and 20060194240A1: each incorporated by reference herein).

In certain embodiments comprising an amplification-based detection assay targeting a *Lactobacillus* sp., A. vaginae, and/or *G. vaginalis* 16S rRNA or a gene encoding a *Lactobacillus* sp., A. vaginae, and/or *G. vaginalis* 16S rRNA, the method utilizes one or more detection probes that specifically hybridizes to a *Lactobacillus* sp., A. vaginae, and/or *G. vaginalis* 16S rRNA amplification product. In particular variations, (A) a *Lactobacillus*-specific detection probe specifically hybridizes to (1) a nucleic acid target region corresponding to a region of SEQ ID NO: 1 from about nucleotide position 40 to about nucleotide position 265, (2) a nucleic acid target region corresponding to a region of SEQ ID NO: 2 from about nucleotide position 43 to about nucleotide position 247, and/or (3) a nucleic acid target region corresponding to a region of SEQ ID NO:3 from about nucleotide position 93 to about nucleotide position 298: (B) a A. vaginae-specific detection probe specifically hybridizes to a nucleic acid target region corresponding to a region of SEQ ID NO:4 from about nucleotide position 540 to about nucleotide position 625; and/or (C) a *G. vaginalis*-specific detection probe specifically hybridizes to a nucleic acid target region corresponding to a region of SEQ ID NO:5 from about nucleotide position 172 to about nucleotide position 227. For example, in some variations, a first probe for detection of a *Lactobacillus* sp. amplification product includes a target-hybridizing sequence that specifically hybridizes to a target region of each of L. crispatus and L. *jensenii* target nucleic acid, and a second probe for detection of *Lactobacillus* sp. amplification product includes a target-hybridizing sequence that specifically hybridizes to a target region of L. gasseri target nucleic acid: in some such embodiments, a first *Lactobacillus*-specific detection probe includes a target-hybridizing sequence substantially corresponding to the sequence of residues 1-17 of SEQ ID NO: 11 and/or a second *Lactobacillus*-specific detection probe includes a target-hybridizing sequence substantially corresponding to the sequence of residues 7-23 of SEQ ID NO: 12 (e.g., a first probe that comprises the target-hybridizing sequence of residues 1-17 of SEQ ID NO: 11 and/or a second probe that comprises the target-hybridizing sequence of residues 7-23 of SEQ ID NO: 12). In some variations, a probe for detection of a A. vaginae amplification product includes a target-hybridizing sequence substantially corresponding to the sequence of residues 6-21 of SEQ ID NO: 19 (e.g., a probe that comprises the target-hybridizing sequence of residues 6-21 of SEQ ID NO: 19). In some variations, a probe for detection of a *G. vaginalis* amplification product includes a target-hybridizing sequence substantially corresponding to the sequence of residues 1-18 of SEQ ID NO:16 (e.g., a probe that comprises the target-hybridizing sequence of residues 1-18 of SEQ ID NO:16). In certain embodiments, a first probe for detection of a *Lactobacillus* sp. amplification product comprises or consists of the sequence of SEQ ID NO:11: a second probe for detection of a *Lactobacillus* sp. amplification product comprises or consists of the sequence of SEQ ID NO: 12: a probe for detection of a A. vaginae amplification product comprises or consists of the sequence of SEQ ID NO: 19; and/or a probe for detection of a *G. vaginalis* amplification product comprises or consists of the sequence of SEQ ID NO: 16.

In some embodiments of a method comprising the use of a nucleic-acid-based detection assay, a non-amplification-based assay is used to detect *Lactobacillus* sp., A. vaginae, and/or *G. vaginalis*. In some such embodiments, the non-amplification-based assay is a hybridization assay comprising the hybridization of a specific detection probe to a target nucleic acid. Methods for conducting polynucleotide hybridization assays have been well developed in the art. Hybridization assay procedures and conditions will vary depending on the application and are selected in accordance with the general binding methods known, including those referred to in, e.g., Maniatis et al., Molecular Cloning: A Laboratory Manual (3rd ed. Cold Spring Harbor, N.Y., 2002), and Berger and Kimmel, Methods in Enzymology. Vol. 152. Guide to Molecular Cloning Techniques (Academic Press, Inc., San Diego, Calif., 1987). Generally, the probe and sample are mixed under conditions that will permit specific nucleic acid hybridization, and specific hybridization of the probe to its respective target is then detected. Nucleic acid hybridization is adaptable to a variety of assay formats. One suitable format is the sandwich assay format, which is particularly adaptable to hybridization under non-denaturing conditions. A primary component of a sandwich-type assay is a solid support, which has adsorbed to it or covalently coupled to it immobilized nucleic acid probe that is unlabeled and complementary to one portion of the DNA sequence. Target nucleic acid is hybridized to the immobilized probe, and a second, labeled detection probe-which is complementary to a second and different region of the same DNA strand to which the immobilized, unlabeled nucleic acid probe is hybridized—is hybridized to the |target nucleic acid|: [immobilized probe] duplex to detect the target nucleic acid. Another exemplary format utilizes electrochemical detection of target nucleic acids hybridized to unlabeled detection probes immobilized on a suitable electrode surface as a signal transducer. See. e.g., Drummond et al., Nat. Biotechnol. 21:1192, 2003; Gooding, Electroanalysis 14:1149, 2002: Wang, Anal. Chim. Acta 469:63, 2002: Cagnin et al., Sensors 9:3122, 2009; Katz and Willner, Electroanalysis 15:913, 2003; Daniels and Pourmand, Electroanalysis 19:1239, 2007.

In certain embodiments comprising a hybridization assay, a detection probe is utilized for the detection of a *Lactobacillus* sp., A. vaginae, and/or *G. vaginalis* 16S rRNA or a gene encoding a *Lactobacillus* sp., A. vaginae, and/or *G. vaginalis* 16S rRNA. In some such embodiments, (A) a probe for detecting a *Lactobacillus* sp. 16S rRNA or gene encoding a *Lactobacillus* sp. 16S rRNA specifically hybridizes to (1) a nucleic acid target region corresponding to a region of SEQ ID NO: 1 from about nucleotide position 40 to about nucleotide position 265, (2) a nucleic acid target region corresponding to a region of SEQ ID NO: 2 from about nucleotide position 43 to about nucleotide position 247, and/or (3) a nucleic acid target region corresponding to a region of SEQ ID NO:3 from about nucleotide position 93 to about nucleotide position 298: (B) a probe for detecting a A. vaginae 16S rRNA or gene encoding a A. vaginae 16S rRNA specifically hybridizes to a nucleic acid target region corresponding to a region of SEQ ID NO:4 from about nucleotide position 540 to about nucleotide position 625; and/or (C) a probe for detecting a *G. vaginalis* 16S rRNA or gene encoding a *G. vaginalis* 16S rRNA specifically hybridizes to a nucleic acid target region corresponding to a region of SEQ ID NO:5 from about nucleotide position 172 to about nucleotide position 227. For example, in some variations, a first probe for detection of a *Lactobacillus* sp. 16S rRNA or gene encoding a *Lactobacillus* sp. 16S rRNA includes a target-hybridizing sequence that specifically hybridizes to a target region of each of L. crispatus and L. jensenii target nucleic acid, and a second a probe for detection of a *Lactobacillus* sp. 16S rRNA or gene encoding a *Lactobacillus* sp. 16S IRNA includes a target-hybridizing sequence that specifically hybridizes to a target region of L. gasseri target nucleic acid: in some such embodiments, a first *Lactobacillus*-specific detection probe includes a target-hybridizing sequence substantially corresponding to the sequence of residues 1-17 of SEQ ID NO: 11 and/or a second *Lactobacillus*-specific detection probe includes a target-hybridizing sequence substantially corresponding to the sequence of residues 7-23 of SEQ ID NO:12 (e.g., a first probe that comprises the target-hybridizing sequence of residues 1-17 of SEQ ID NO:11 and/or a second probe that comprises the target-hybridizing sequence of residues 7-23 of SEQ ID NO: 12). In some variations, a probe for detection of a A. vaginae 16S rRNA or gene encoding a A. vaginae 16S rRNA includes a target-hybridizing sequence substantially corresponding to the sequence of residues 6-21 of SEQ ID NO: 19 (e.g., a probe that comprises the target-hybridizing sequence of residues 6-21 of SEQ ID NO:19). In some variations, a probe for detection of a *G. vaginalis* 16S rRNA or gene encoding a *G. vaginalis* 16S rRNA includes a target-hybridizing sequence substantially corresponding to the sequence of residues 1-18 of SEQ ID NO: 16 (e.g., a probe that comprises the target-hybridizing sequence of residues 1-18 of SEQ ID NO:16). In certain embodiments, a first probe for detection of a *Lactobacillus* sp. 16S rRNA or gene encoding a *Lactobacillus* sp. 16S rRNA comprises or consists of the sequence of SEQ ID NO: 11: a second probe for detection of a *Lactobacillus* sp. 16S rRNA or gene encoding a *Lactobacillus* sp. 16S rRNA comprises or consists of the sequence of SEQ ID NO: 12: a probe for detection of a A. vaginae 16S rRNA or gene encoding a A. vaginae 16S rRNA comprises or consists of the sequence of SEQ ID NO: 19; and/or a probe for detection of a *G. vaginalis* 16S rRNA or gene encoding a *G. vaginalis* 16S rRNA comprises or consists of the sequence of SEQ ID NO: 16.

In some embodiments, a non-amplification-based assay for detection of *Lactobacillus* sp., A. vaginae, and/or *G. vaginalis* is a cleavage-based assay, in which a probe oligonucleotide containing a non-target-hybridizing flap region is cleaved in an overlap-dependent manner by a flap endonuclease to release a cleavage product that is then detected. Exemplary cleavage-based assay reagents are described in, e.g., Lyamichev et al. (Nat. Biotechnol. 17:292-296, 1999), Ryan et al. (Mol. Diagn. 4:135-144, 1999), and Allawi et al. (J. Clin. Microbiol. 44:3443-3447, 2006). Appropriate conditions for flap endonuclease reactions are either known or can be readily determined using methods known in the art (see. e.g., Kaiser et al., J. Biol. Chem. 274:2138-721394, 1999). Exemplary flap endonucleases that may be used in the method include *Thermus aquaticus* DNA polymerase I, *Thermus thermophilus* DNA polymerase I, mammalian FEN-1, *Archaeoglobus fulgidus* FEN-1, Methanococcus jannaschii FEN-1, *Pyrococcus furiosus* FEN-1, *Methanobacterium* thermoautotrophicum FEN-1, *Thermus thermophilus* FEN-1, CLEAVASE® (Hologic, Inc., Madison, WI), *S. cerevisiae* RTH1, *S. cerevisiae* RAD27, *Schizosaccharomyces pombe* rad2, bacteriophage T5 5'-3' exonuclease, *Pyrococcus horikoshii* FEN-1, human endonuclease 1, calf thymus 5'-3' exonuclease, including homologs thereof in eubacteria, eukaryotes, and archaea, such as members of the class II family of structure-specific enzymes, as well as enzymatically active mutants or variants thereof. Descriptions of flap endonucleases can be found in, for example, Lyamichev et al., Science 260:778-783, 1993; Eis et al., Nat. Biotechnol. 19:673-676, 2001: Shen et al., Trends in Bio. Sci. 23:171-173, 1998: Kaiser et al., J. Biol. Chem. 274: 21387-21394, 1999; Ma et al., J. Biol. Chem. 275:24693-24700, 2000; Allawi et al., J. Mol. Biol. 328:537-554, 2003; Sharma et al., J. Biol. Chem. 278:23487-23496, 2003; and Feng et al., Nat. Struct. Mol. Biol. 11:450-456, 2004.

In certain variations, a cleavage-based assay detects an RNA target nucleic acid of *Lactobacillus* sp., A. vaginae, and/or *G. vaginalis*, and the cleavage-based assay utilizes a flap endonuclease that is capable of cleaving an RNA: DNA linear duplex structure. In some alternative embodiments, a cleavage-based assay detects a DNA target nucleic acid of *Lactobacillus* sp., A. vaginae, and/or *G. vaginalis*, and the cleavage-based assay utilizes a flap endonuclease that is capable of cleaving a DNA: DNA linear duplex structure. Exemplary flap endonucleases capable of cleaving RNA: DNA duplexes include polymerase-deficient 5' nucleases of the genus *Thermus* as well as certain CLEAVASE® enzymes (Hologic, Inc.) such as, for example, CLEAVASE® BN (BstX-NotI deletion of Taq polymerase, see U.S. Pat. No. 5,614,402), CLEAVASER II ("AG" mutant of full length Taq polymerase, see U.S. Pat. No. 5,614,402), CLEAVASE® VII (synthesis-deficient mutation of full length *Thermus thermophilus* polymerase), CLEAVASE® IX (polymerase deficient mutant of the Tth DNA polymerase), and CLEAVASE® XII (polymerase deficient chimeric polymerase constructed from fragments of taq DNA polymerase and Tth DNA polymerase). Exemplary flap endonucleases capable of cleaving DNA: DNA duplexes include the flap endonucleases indicated above, as well as CLEAVASE® 2.0 (*Archaeoglobus fulgidus* FEN-1), CLEAVASE® 2.1 (*Archaeoglobus fulgidus* FEN-1 with 6 histidines on the C-terminus), CLEAVASE® 3.0 (*Archaeoglobus veneficus* FEN-1), and CLEAVASE® 3.1 (*Archaeoglobus veneficus* FEN-1 with 6 histidines on the C-terminus).

In some embodiments, a cleavage-based assay detects an RNA target nucleic acid of *Lactobacillus* sp., A. vaginae, and/or *G. vaginalis*, and the assay includes a step for synthesizing a DNA complement of an RNA target region, which cDNA strand is then hybridized to overlapping first and second probe oligonucleotides to form a linear duplex cleavage structure for cleavage by the flap endonuclease. Reaction conditions for synthesizing cDNA from an RNA template, using an RNA-dependent DNA polymerase (reverse transcriptase), are well-known in the art.

In certain embodiments utilizing a nucleic-acid-based detection assay, the method further includes purifying the *Lactobacillus* sp., A. vaginae, and/or *G. vaginalis* target nucleic acid from other components in the sample. Such purification may include may include methods of separating and/or concentrating organisms contained in a sample from other sample components. In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains *Lactobacillus* sp., A. vaginae, and/or *G. vaginalis* nucleic acid and other sample components.

In some embodiments, a target nucleic acid (e.g., a 16S rRNA target nucleic or a gene encoding the 16S rRNA) of *Lactobacillus* sp., A. vaginae, and/or *G. vaginalis* is separated from other sample components by hybridizing the target nucleic acid to a capture probe oligomer. The capture probe oligomer comprises a target-hybridizing sequence configured to specifically or non-specifically hybridize to a target nucleic acid so as to form a [target nucleic acid]:[capture probe] complex that is separated from other sample components. Capture probes comprising target-hybridizing sequences suitable for non-specific capture of target nucleic acids are described in, e.g., International PCT Publication WO 2008/016988, incorporated by reference herein. In some variations, a step for separating a target nucleic acid from other sample components includes contacting the sample with (i) a first capture probe oligomer comprising a target-hybridizing sequence that specifically hybridizes to a target sequence within *Lactobacillus* sp. target nucleic acid (e.g., a target-hybridizing sequence that specifically hybridizes to a target sequence within each of L. crispatus, L. *jensenii*, and L. gasseri target nucleic acid) and (ii) a second capture probe oligomer comprising a target-hybridizing sequence that specifically hybridizes to a target sequence within each of A. vaginae and *G. vaginalis* target nucleic acids. In some specific variations comprising first and second capture probe oligomers of (i) and (ii) above, a first capture probe oligomer comprises a target-hybridizing sequence substantially corresponding to the nucleotide sequence of residues 1-19 of SEQ ID NO:6 (e.g., a capture probe that comprises the target-hybridizing sequence of residues 1-19 of SEQ ID NO:6), and/or a second capture probe oligomer comprises a target-hybridizing sequence substantially corresponding to the nucleotide sequence of residues 1-20 of SEQ ID NO: 13 (e.g., a capture probe that comprises the target-hybridizing sequence of residues 1-20 of SEQ ID NO:13). In a preferred variation, the capture probe binds the [target nucleic acid]:[capture probe] complex to an immobilized probe to form a [target nucleic acid]:[capture probe]:[immobilized probe] complex that is separated from the sample and, optionally, washed to remove non-target sample components (see. e.g., U.S. Pat. Nos. 6,110,678; 6, 280,952; and 6,534,273: each incorporated by reference herein). In such variations, the capture probe oligomer further comprises a sequence or moiety that attaches the capture probe, with its bound target sequence, to an immobilized probe attached to a solid support, thereby permitting the hybridized target nucleic acid to be separated from other sample components.

In more specific embodiments, the capture probe oligomer includes a tail portion (e.g., a 3' tail) that is not complementary to target nucleic acid but that specifically hybridizes to a sequence on the immobilized probe, thereby serving as the moiety allowing the target nucleic acid to be separated from other sample components, such as previously described in, e.g., U.S. Pat. No. 6,110,678, incorporated herein by reference. Any sequence may be used in a tail region, which is generally about 5 to 50 nt long, and preferred embodiments include a substantially homopolymeric tail of about 10 to 40 nt (e.g., Aio to A+0), more preferably about 14 to 33 nt (e.g., A14 to A30 or T3A14 to T3A30), that bind to a complementary immobilized sequence (e.g., poly-T) attached to a solid support, e.g., a matrix or particle. In some such embodiments comprising (i) a first capture probe oligomer comprising a target-hybridizing sequence that specifically hybridizes to a target sequence within each of L. crispatus, L. *jensenii*, and L. gasseri 16S rRNA target nucleic acid and/or (ii) a second capture probe oligomer comprising a target-hybridizing sequence that specifically hybridizes to a target sequence within each of A. vaginae and *G. vaginalis* 16S rRNA target nucleic acids, a first capture probe oligomer comprises or consists of the nucleotide sequence of SEQ ID NO:6 and/or the second capture probe oligomer comprises or consists of the nucleotide sequence of SEQ ID NO:13.

Target capture typically occurs in a solution phase mixture that contains one or more capture probe oligomers that hybridize to the target nucleic acid under hybridizing conditions, usually at a temperature higher than the $T_m$ of the [tail sequence]: [immobilized probe sequence] duplex. For embodiments comprising a capture probe tail, the [target nucleic acid]: [capture probe] complex is captured by adjusting the hybridization conditions so that the capture probe tail hybridizes to the immobilized probe, and the entire complex on the solid support is then separated from other sample components. The support with the attached [immobilized probe]: [capture probe]: [target nucleic acid] may be washed one or more times to further remove other sample components. Preferred embodiments use a particulate solid support, such as paramagnetic beads, so that particles with the attached [target nucleic acid]: [capture probe]: [immobilized probe] complex may be suspended in a washing solution and retrieved from the washing solution, preferably by using magnetic attraction. In embodiments of the method comprising the use of an amplification-based detection assay, to limit the number of handling steps, a target nucleic acid may be amplified by simply mixing the target nucleic acid in the complex on the support with amplification oligomers and proceeding with amplification steps.

In some embodiments of a method for diagnosing BV, where detection of *Lactobacillus* sp., A. vaginae, and/or *G. vaginalis* indicate BV in a subject, the method further includes treating BV in the subject. Treatment regimes for BV are generally known in the art and include, for example, administration of antibiotic drugs such as metronidazole (e.g., FLAGYL, METROGEL-VAGINAL), clindamycin (e.g., CLEOCIN, CLINDESSE), and tinidazole (e.g., TINDAMAX). In certain variations, the subject has not been previously diagnosed with BV. In other embodiments, the subject has been previously diagnosed with BV and is undergoing treatment for BV at the time a diagnostic method of the present disclosure is performed. Such variations are particularly useful for monitoring treatment of BV in a subject. For example, if the method indicates that BV is still present in the subject, then the subject may continue treatment. In some embodiments, the same treatment regime (i.e., the same treatment that the subject is undergoing at the time the present diagnostic method is performed) is re-administered to the subject. Alternatively, the continued presence of BV in the subject undergoing treatment may indicate that a change in the ongoing treatment is needed, and a different treatment regime (e.g., a different medication, or an increased dosage and/or frequency of a drug) is administered to the subject.

In accordance with the present invention, detecting the presence or absence of *Lactobacillus* sp., A. vaginae, and/or *G. vaginalis* may be performed separately for each target (e.g., in separate reaction vessels, sequentially or in parallel), or performed together as a multiplex reaction system. Accordingly, in some embodiments, a method as described herein (e.g., a method for diagnosing BV) utilizes a multiplex reaction, where the reaction mix contains reagents for assaying multiple (e.g., at least two, three, four, or more) different target sequences in parallel. In these cases, a reaction mix may contain multiple different target-specific oligonucleotides for performing the detection assay. For example, in a method utilizing an amplification-based detection assay, a multiplex reaction may contain multiple sets (e.g., multiple pairs) of amplification oligomers (for example, multiple pairs of PCR primers or multiple pairs of TMA amplification oligomers (e.g., for TMA, multiple pairs of promoter primer and non-promoter primer, or multiple pairs of promoter provider and non-promoter primer)). In other embodiments utilizing a cleavage-based detection assay, a multiplex reaction may contain multiple probe oligonucleotides having different flaps, multiple different overlapping probe oligonucleotides, and multiple different FRET cassettes for detecting the different flaps, once they are cleaved.

Additional microbe detection assays can be similarly performed for determining the presence and/or relative amount of a plurality of microbes implicated in BV. By way of example only, such plurality of microbes can include one or more of anaerobic gram-positive cocci: *Eggerthella* sp.: Bacterium from the order Clostridiales: *Clostridium*-like sp.: Enterobacteria: *Peptostreptococcus* micros: *Aerococcus christensenii*: Leptotrichia amnionii: Peptoniphilus sp.: Dialister sp.: *Mycoplasma hominis*: Sneathia sanguinegens: Anaerococcus *tetradius*: Mobiluncus sp.: Mobiluncus *hominis*: Eggerthella *hongkongensis: Prevotella* sp.: Megasphaera sp.: Leptotrichia sanguinegens and *Finegoldia magna*. Assays may be performed separately or multiplexed. Thus, a diagnosis of BV can include identifying a plurality of microbes and optionally determining their relative abundances in a sample.

In certain embodiments, the method for diagnosing BV includes the detection of no more than ten bacterial genera associated with BV. In other embodiments, the method includes the detection of no more than nine, no more than eight, no more than seven, no more than six, no more than five, or nor more than four bacterial genera associated with BV. In some variations, the method does not include detection of bacterial genera associated with BV other than *Lactobacillus*, Atopobium, and *Gardnerella*.

Also provided by the subject invention is an oligomer or combination thereof for determining the presence or absence of any one or more of *Lactobacillus* sp., A. vaginae, and *G. vaginalis* in a sample. In various embodiments, the oligomer or combination thereof includes oligomers as set forth herein for a method for determining the presence or absence of *Lactobacillus* sp., A. vaginae, and/or *G. vaginalis* in a sample. In some variations, an oligomer combination includes at least one *Lactobacillus*-specific oligonucleotide (e.g., at least two or three *Lactobacillus*-specific oligonucleotides, each binding to different target sequences): at least one A. vaginae-specific oligonucleotide (e.g., at least two or three A. vaginae-specific oligonucleotides, each binding to different target sequences); and/or at least one *G. vaginalis*-specific oligonucleotide (e.g., at least two or three *G. vaginalis*-specific oligonucleotides, each binding to different target sequences). In some variations, an oligomer combination includes at least two *Lactobacillus*-specific oligonucleotides (e.g., at least three *Lactobacillus*-specific oligonucleotides, each binding to different target sequences): at least two A. vaginae-specific oligonucleotides (e.g., at least three A. vaginae-specific oligonucleotides, each binding to different target sequences); and/or at least two *G. vaginalis*-specific oligonucleotides (e.g., at least three *G. vaginalis*-specific oligonucleotides, each binding to different target sequences). In some embodiments, an oligomer combination includes at least two *Lactobacillus*-specific amplification oligonucleotides for amplifying a *Lactobacillus* sp. nucleic acid target region: at least two A. vaginae-specific amplification oligonucleotides for amplifying a A. vaginae nucleic acid target region; and/or at least two *G. vaginalis*-specific amplification oligonucleotides for amplifying a *G. vaginalis* nucleic acid target region. In some embodiments, a composition of the present invention comprises one or more detection probe oligomers for detecting a *Lactobacillus* sp. target nucleic acid, a A. vaginae target nucleic acid, and/or a *G. vaginalis* target nucleic acid. An oligomer or combination thereof may be in the form of a reaction mixture or a kit comprising the oligomer(s). The reaction mixture or kit may further include a number of optional components such as, for example, capture probe nucleic acids or arrays of capture probe nucleic acids. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase), and will typically include test sample components, in which an *Lactobacillus* sp., A. vaginae, and/or *G. vaginalis* target nucleic acid may or may not be present. A kit comprising an oligomer combination for amplification of one or more target nucleic acid regions of *Lactobacillus* sp., A. vaginae, and/or *G. vaginalis* may also include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase). For an oligomer combination (e.g., reaction mixture or kit) that includes a detection probe together with an amplification oligomer combination targeting a common target nucleic acid, selection of amplification oligomers and detection probe oligomers are linked by a common target region (i.e., the combination will include a probe that binds to a sequence amplifiable by the amplification oligomer combination).

The invention is further illustrated by the following non-limiting examples.

Example 1: BV Multivariate Algorithm

1. Results Interpretion Summary

To determine BV positive or BV negative status, quantitative information for *Lactobacillus* spp. ("L.spp": negatively correlating with BV) and for *Gardnerella vaginalis* and *Atopobium vaginae* ("Gvag" and "Avag," respectively: positively correlating with BV) are combined into a single, numerical BV score using a multivariate linear predictor algorithm. This score is compared to a single cutoff value, with negative calls below the cutoff, and positive calls at or above the cutoff.

In a simplified version of this algorithm, the L.spp quantitated value (in units of LogCopies) is subtracted from the Gvag or Avag value (whichever is maximum):

Simplified score=Max (Gvag, Avag)–L.spp

As actually applied for APTIMA BV results interpretation, the formula takes on additional complexity. A negative constant is added (to bring the score at the clinical decision point to zero), an additional factor (the IC term) is added (to compensate for observed inhibition), a minimum value is imposed for L.spp (to improve reproducibility), concentrations of the three analytes are standardized (to balance participation of Gvag and Avag in the algorithm), and each of the terms is weighted.

The formula, as applied:

$$\text{Score} = C_0 + W_L * \text{Max}(L-M_L, F_L-M_L) + W_{AG} * \text{Max}(G-M_G, A-M_A, F_{GA}-M_G) + W_{IC} * \log 2(IC/\text{calIC})$$

2. Results Interpretation Details

Specimen interpretation consists of evaluating validity criteria, calculating a BV score, and interterpreting the score. The description in this example starts from the TTime value of the internal control (IC) signal and LogCopy/mL quantitated values for L.spp, Gvag and Avag (L, G, A) for each specimen to be evaluated.

2.1 Calculating the BV Score

For specimens meeting the validity criteria (not described here), the BV score is calculated. Calculating the BV score consists of three steps: 1) analyte standardization, 2) calculation of the IC ratio, and 3) application of the universal equation.

2.1.1 Analyte Standardization

In a population of clinical specimens, observed Gvag concentrations trend higher than Avag concentrations. Since the linear predictor formula utilizes only the maximum value (Gvag LogC or Avag LogC), the terms are leveled to balance the likelihood of each analyte participating in the algorithm. A robust method of leveling is to adjust the terms by a population statistic (median value). If the concentrations had been in units of copies, they would have been divided by the median values, and the relative concentrations given as the standardized values. Since the quantitative data used here are in units of Log Copies, the equivalent manipulation is to subtract the median LogC values.

Standardization serves two main functions:

1) it levels the concentration numbers (as described above), and 2) it improves confidence intervals of trained constants.

This form of standardization is applied to all of the terms that are present in units of Log Copies. This includes the three specimen analyte values (L, G, A) and the foundation values $F_L$ and $F_{GA}$. Each of these is standardized (by subtracting median population values ($M_L$, $M_G$, $M_A$) prior to use in the linear predictor formula. Standardized values are indicated with a subscript of "S" in the universal equation.

TABLE 2

Analyte Standardization

| Term | Standardized Term | Designation |
| --- | --- | --- |
| L | L-$M_L$ | $L_S$ |
| $F_L$ | $F_L$-$M_L$ | $F_{LS}$ |
| G | G-$M_G$ | $G_S$ |
| $F_{GA}$ | $F_{GA}$-$M_G$ | $F_{GAS}$ |
| A | A-$M_A$ | $A_S$ |

2.1.2 Calculation of the IC Ratio

The IC ratio is used in the universal equation as part of a term that compensates for specimen inhibition in order to reduce the probability of false negative calls. The IC ratio is the observed value for the internal control (IC) TTime divided by the expected value for the IC TTime. If the reaction is inhibited (reaction slower than expected), then the IC ratio is above 1. The expected IC TTime is calculated as the mean observed IC TTime of the valid KitCalibrator replicates.

For specimens not generating an IC TTime, the IC ratio is defined as the constant ICd. A default IC TTime can be calculated as ICd times the mean observed IC TTime of the valid KitCalibrator replicates. Any IC TTime that is not less than the default IC TTime will use ICd as the IC ratio.

$$\text{IC ratio} = \frac{\text{observed IC TTime}}{\text{expected IC TTime}} \quad \text{maximum IC ratio} = ICd$$

2.1.3 The Universal Equation

The equation coded into the PANTHER® software for APTIMA® BV results interpretation is referred to as the universal equation. In this equation, the subscript "S" refers to values that have been standardized by subtraction of population median values for the relevant analyte.

$$BV\ \text{Score} = C_0 + W_L \text{Max}(L_S, F_{LS}) + W_A \text{Max}(A_S, F_{AS}) + W_G \text{Max}(G_S, F_{GS}) + W_{GA} \text{Max}(A_S, G_S, F_{GAS}) + W_{IC} \log 2(\text{ICRatio})$$

This universal equation was implemented prior to finalizing the algorithm. Subsequently, both $W_A$ and $W_G$ have been set to zero. The equation (as applied) can therefore be simplified to the following:

$$BV\ \text{Score} = C_0 + W_L \text{Max}(L_S, F_{LS}) + W_{GA} \text{Max}(A_S, G_S, F_{GAS}) + W_{IC} \log 2(\text{ICRatio})$$

In this equation, four terms are added together to build a score.

TABLE 3

Terms in the Universal Equation

| Analyte | Term | Description |
| --- | --- | --- |
| n/a | $C_0$ | Adjustment constant to bring the decision point to zero |
| L.spp | $W_L \text{Max}(L_S, FL_S)$ | A weighting constant times the maximum value of L.spp (standardized) or the L.spp foundation value (standardized) |
| Gvag/Avag | $W_{GA}\text{Max}(A_S, G_S, F_{GAS})$ | A weighting constant times the maximum of the following 3 values: Avag (standardized), Gvag (standardized), or the combined Gvag/Avag foundation value (standardized) |
| IC | $W_{IC}\text{Log2(ICRatio)}$ | A weighting constant times the base 2 logarithm of the IC ratio |

2.2 Interpreting the BV Score

In order to determine BV positive or BV negative status (the reported call), the numerical BV score is compared to a single cutoff value (presently set to zero). If the BV score for a specimen is less than the cutoff value, the specimen is reported as BV negative. If the score is greater than or equal to the cutoff value, the specimen is reported BV positive.

3. Application of the Multivariate Algorithm to Clinical Specimen Results Interpretation For interpretation of BV clinical outcomes, the "true result" was determined by Nugent score with intermediates determined with Amsel criteria, as shown in Table 4.

TABLE 4

Determination of the BV Reference Calls

| Nugent score | Nugent Call | Clue Cells | Vaginal pH >4.5 | Whiff test | Modified Amsel Call | Reference Call |
|---|---|---|---|---|---|---|
| 0-3 | Negative | n/a | n/a | n/a | n/a | Negative |
| 7-10 | Positive | n/a | n/a | n/a | n/a | Positive |
| 4-6 | Intermediate | Positive | Positive | Any | Positive | Positive |
| 4-6 | Intermediate | Positive | Any | Positive | Positive | Positive |
| 4-6 | Intermediate | Positive | Negative | Negative | Negative | Negative |
| 4-6 | Intermediate | Negative | Any | Any | Negative | Negative |

The constants used in the algorithm are described in Table 5 and shown with the numerical values that were used for this analysis.

TABLE 5

Algorithm Constants, Values, and Descriptions

| Constant | Value | Description |
|---|---|---|
| $C_0$ | −1.541 | Adjustment constant to bring clinical decision point to zero |
| $W_L$ | −1.070 | Weighting constant for the L.spp term |
| $W_G$ | 0.000 | Weighting constant for the Gvag term (term disabled) |
| $W_A$ | 0.000 | Weighting constant for the Avag term (term disabled) |
| $W_{GA}$ | 1.678 | Weighting constant for the combined Gvag/Avag term |
| $W_{IC}$ | 3.302 | Weighting constant for the IC term |
| $F_L$ | 7.0 | L.spp foundation value: minimum value of L.spp affecting the BV score; also used in validity assessment |
| $F_G$ | 8.147 | Gvag foundation value; used in validity assessment |
| $F_A$ | 6.747 | Avag foundation value; used in validity assessment |
| $F_{GA}$ | 0.0 | Gvag/Avag foundation value; set to 8.0 for training weighting constants, then to zero in final algorithm |
| $M_L$ | 9.31 | Population median for L.spp LogC; used for standardization |
| $M_G$ | 10.23 | Population median for Gvag LogC; used for standardization |
| $M_A$ | 8.83 | Population median for Avag LogC; used for standardization |
| ICd | 1.713 | Default IC ratio: used as the IC ratio for specimens not amplifying IC |

Two sets data were assembled from BV RT-TMA PANTHER test results for the APTIMA product in development. The training set consists of 1204 test results at one test per subject. This data set was used to derive the values of the constants shown in Table 5. The validation set consists of 1076 test results at one test per subject. The population of subjects was the same, but no test results were in common between the training and validation sets. ("Training sets" and "validation sets" herein refer to clinical specimen sets tested with the same assay design to optimize the algorithm for making clinical calls (positive or negative). The training set is a group of specimens that is used to design a provisional algorithm, and the validation set is a separate specimen set to test the accuracy of the algorithm performance.)

Using the constants from Table 5 in the universal equation gives the clinical performance (sensitivity/specificity) estimates on the training set and validation set shown in Table 6.

TABLE 6

Clinical Performance Estimates

| | | Original | Bootstrap, B = 10,000 | | |
|---|---|---|---|---|---|
| | | | Mean | Lower95 | Upper95 |
| Training Set (n = 1,204) | Sensitivity | 93.1% | 93.1% | 91.1% | 94.9% |
| | Specificity | 90.0% | 90.1% | 87.7% | 91.8% |
| Validation (n = 1070) | Sensitivity | 93.1% | 93.1% | 90.3% | 95.2% |
| | Specificity | 88.9% | 88.8% | 86.3% | 91.1% |

BV can present differently in different racial and ethnic groups. The training set and the validation set are therefore being shown parsed by race/ethnicity using the following categories: Black or African American regardless of ethnicity (Black), Non-Hispanic White (White-NH), Hispanic White (White-Hisp), Asian regardless of ethnicity (Asian), and Other. The category of Other consists of Islander, Indian, Middle Eastern, Native American, and people of other, unknown, or mixed races.

TABLE 7

Training Set Clinical Outcome by Race

| Training | White-HISP | White-NH | Black | Asian | Other | ALL |
|---|---|---|---|---|---|---|
| TP | 86 | 108 | 234 | 5 | 25 | 458 |
| FP | 11 | 29 | 28 | 1 | 2 | 71 |
| TN | 156 | 257 | 181 | 16 | 31 | 641 |

TABLE 7-continued

Training Set Clinical Outcome by Race

| Training | White-HISP | White-NH | Black | Asian | Other | ALL |
|---|---|---|---|---|---|---|
| FN | 5 | 10 | 17 | 0 | 2 | 34 |
| % sensitivity | 94.5% | 91.5% | 93.2% | 100.0% | 92.6% | 93.1% |
| % specificity | 93.4% | 89.9% | 86.6% | 94.1% | 93.9% | 90.0% |
| % agreement | 93.8% | 90.3% | 90.2% | 95.5% | 93.3% | 91.3% |

TABLE 7-continued

Training Set Clinical Outcome by Race

| Training | White-HISP | White-NH | Black | Asian | Other | ALL |
|---|---|---|---|---|---|---|
| % by race | 21.4% | 33.6% | 38.2% | 1.8% | 5.0% | 100.0% |
| % refpos | 35.3% | 29.2% | 54.6% | 22.7% | 45.0% | 40.9% |
| N total | 258 | 404 | 460 | 22 | 60 | 1204 |

TABLE 8

Validation Set Clinical Outcome by Race

| Validation | White-HISP | White-NH | Black | Asian | Other | ALL |
|---|---|---|---|---|---|---|
| TP | 82 | 88 | 207 | 2 | 24 | 403 |
| FP | 11 | 28 | 28 | 2 | 2 | 71 |
| TN | 148 | 217 | 163 | 15 | 23 | 566 |
| FN | 3 | 10 | 17 | 0 | 0 | 30 |
| INVALID | 0 | 3 | 3 | 0 | 0 | 6 |
| % invalid | 0.0% | 0.9% | 0.7% | 0.0% | 0.0% | 0.6% |
| % sensitivity | 96.5% | 89.8% | 92.4% | 100.0% | 100.0% | 93.1% |
| % specificity | 93.1% | 88.6% | 85.3% | 88.2% | 92.0% | 88.9% |
| % agreement | 94.3% | 88.9% | 89.2% | 89.5% | 95.9% | 90.6% |
| % by race | 22.7% | 32.2% | 38.8% | 1.8% | 4.6% | 100.0% |
| % refpos | 34.8% | 29.2% | 54.3% | 10.5% | 49.0% | 40.8% |
| N total | 244 | 346 | 418 | 19 | 49 | 1076 |

Example 2: Amplification Interference

It is desirable that amplification oligos specifically detect 16S rRNA of the targeted species with minimal interference from other organisms which may be present in high titer in the preferred specimen type. 16S rRNA sequence alignments of G.vag with other vaginal organisms showed similarity between G.vag and Bifidobacteria sequences suggesting that interference by Bifidobacteria or other related organisms could influence detection of G.vag in some specimens. Additional G.vag amplification oligos were designed to reduce possible interference.

An initial design targeted amplification of SEQ ID NO:5, from about 964 to 1033 (region 1). Additional oligos were screened targeting a site with potentially greater specificity (SEQ ID NO:5, from approximately base 160 to 277 (region 2)).

To test interference, primer sets were tested in a manual RT-TMA format on samples containing 1E4 CFU/mL G.vag with or without higher concentrations of Bifidobacterium breve present in the samples. Each set was tested at five replicates and the mean values (RFU range, Non-normalized Ttime, and Non-normalized Tslope) shown for each condition relative to the 1E4 CFU/mL Gvag condition in the absence of B. breve.

TABLE 9

| Set (Region) Primer/Promoter | Set 1 (Region 1) SEQ ID NO: 33/ SEQ ID NO: 32 | | | Set 2 (Region 2) SEQ ID NO: 42/ SEQ ID NO: 57 | | | Set 3 (Region 2) SEQ ID NO: 60/ SEQ ID NO: 65 | | |
|---|---|---|---|---|---|---|---|---|---|
| primer Condition | RFU range | Ttime | Tslope | RFU range | Ttime | Tslope | RFU range | Ttime | Tslope |
| 1E6 CFU/mL B. breve | 93% | 107% | 67% | 98% | 104% | 98% | 99% | 103% | 98% |
| 1E7 CFU/mL B. breve | 58% | 132% | 19% | 97% | 104% | 96% | 96% | 105% | 104% |
| 1E8 CFU/mL B. breve | 20% | 186% | 7% | 95% | 107% | 93% | 93% | 107% | 98% |

Results of test for G.vag amplification interference. Both sets in Region 2 gave relatively stable G.vag detection in the presence of high titers of B. breve. Set 1 (in Region 1), in contrast, gave decreased RFU range, decreased Tslope and increased Ttime in the presence of increasing concentrations of B. breve, demonstrating G.vag amplification interference.

An initial oligo combination for detection of Lactobacillus species (L. gasseri. L. jensenii. and L. crispatus) showed reduced detection of low concentration L. gasseri in the presence of high concentrations of several other organisms. To reduce interference and improve specificity, separate forward primers were designed for each of the three targeted Lactobacillus species. The original oligo set and the modified oligo set were each used in a manual RT-TMA format for detection of 1E4 CFU/mL L. gasseri, either alone or in the presence of N. gonorrhoeae at 1E6 CFU/mL. C. difficile at 1E6 CFU/mL, A. Iwoffii at 1E6 CFU/mL, M. hominis at 5E9 copies/mL, or L. iners at 1E6 CFU/mL. The two conditions used the same promoter primer and torch combination (SEQ ID NO: 10, SEQ ID NO:259, and SEQ ID NO: 11). The forward primers used for each condition are indicated in the table below. To assess interference, mean the TTime for each sample was divided by the mean TTime for L. gasseri 1E4 CFU/mL. Ttime ratios over 100% indicate Ttime delay (amplficiation interference).

TABLE 10

| Condition Primers | Initial SEQ ID NO: 258 | Modified SEQ ID NO: 7, SEQ ID NO: 8, SEQ ID NO: 9 |
|---|---|---|
| (N. gonn + L. gass)/L. gass Ttime ratio | 105% | 102% |
| (C. diff + L. gass)/L. gass Ttime ratio | 130% | 102% |
| (A. lwoff + L. gass)/L. gass Ttime ratio | 111% | 101% |
| (M. hominis + L. gass)/L. gass Ttime ratio | 113% | 101% |
| (L. iners + L. gass)/L. gass Ttime ratio | 104% | 101% |

Results of test for Lactobacillus species amplification interference. The initial condition (with a single forwards primer for L. gasseri, L. jensenii, and L. crispatus) showed amplification interference by C. difficile, A. Iwoffi and M.

hominis, while the modified condition (with separate forwards primers for each targeted species) did not.

Example 3: *Lactobacillus* Target Capture Oligo Screen

In order to improve upon an early design (SEQ ID NO:257) for a *Lactobacillus* species target capture oligo, additional designs were made and screened in parallel with the existing design on samples containing 1E4 CFU/mL of L. crispatus, L. gasseri, or L. jensenii. The amplification and detection oligos (common to all conditions) were SEQ ID NO:258, SEQ ID NO: 10, SEQ ID NO:259, and SEQ ID NO: 11. The screen was performed in a manual RT-TMA format at three (3) replicates per condition, with mean normalized Ttime values shown.

TABLE 11

| SEQ ID NO | Condition | L. crispatus | L. gasseri | L. jensenii |
|---|---|---|---|---|
| No TCO | 1 | 32.00 | 30.18 | . |
| SEQ ID NO: 25 | 2 | 19.89 | 16.13 | 20.88 |
| SEQ ID NO: 260 | 3 | 15.89 | 12.70 | 17.56 |
| SEQ ID NO: 257 | 4 | 18.95 | 16.09 | 21.11 |
| SEQ ID NO: 67 | 5 | 15.74 | 11.68 | 15.84 |
| SEQ ID NO: 68 | 6 | 14.70 | 11.62 | 15.78 |
| SEQ ID NO: 6 | 7 | 14.60 | 11.25 | 15.48 |
| SEQ ID NO: 69 | 8 | 16.54 | 12.69 | 17.02 |

Since the conditions vary only by the target capture oligo, slower amplification (higher Ttimes) may be attributed to reduced target capture efficiency. In condition 1, no target capture oligo was utilized, and Ttimes were delayed or absent. Use of target capture oligos is expected to improve upon this by increasing capture efficiency. Each other condition utilized a single TCO for capture of the three *Lactobacillus* species. In conditions 4 through 8, the TCOs were designed to specifically capture *Lactobacillus* 16S rRNA, favoring these sequences over sequences from other genera. In conditions 2 and 3, the TCOs were designed to capture rRNA from other bacteria as well as *Lactobacillus*.

Results. Conditions 5, 6, and 7 have faster Ttimes (more efficient capture) for all three targeted *Lactobacillus* species than the earlier *Lactobacillus* TCO design (condition 4) and both of the less specific TCOs (conditions 2 and 3). Of the three preferred *Lactobacillus* TCO designs, condition 7 (TCO SEQ ID NO:6), showed the highest efficiency (lowest Ttimes) in this experiment.

Example 4: Cross-reactivity in Initial Multiplexing

A multiplex configuration of RT-TMA reagents for detection of G.vag, A.vag, and *Lactobacillus* species was assembled utilizing the oligos in Table 12.

TABLE 12

Oligomers in multiplex for initial specificity testing

| Target | NT7 | Torch | T7 | TCO |
|---|---|---|---|---|
| L. crispatus | SEQ ID NO: 7 | SEQ ID NO: 11 | SEQ ID NO: 10 | SEQ ID NO: 6 |
| L. jensenii | SEQ ID NO: 8 | | | |
| L. gasseri | SEQ ID NO: 9 | SEQ ID NO: 259 | | |
| G. vaginalis | SEQ ID NO: 14 | SEQ ID NO: 16 | SEQ ID NO: 15 | SEQ ID NO: 63 |
| A. vaginae | SEQ ID NO: 45 | SEQ ID NO: 84 | SEQ ID NO: 18 | SEQ ID NO: 54 |
| GIC | (omitted) | SEQ ID NO: 23 | (omitted) | (omitted) |

Reagents were tested on a PANTHER instrument at five replicates per specimen against pools containing from 1 to 5 untargeted organisms at high titer (in most cases 1E6 CFU/mL). Unexpected signal in the FAM channel was observed in Pool #7, which consisted of the following four organisms: Mobiluncus curtisii (5E9 copies rRNA/mL), Mycoplasma genitalium (1E6 CFU/mL), Mycoplasma hominis (5E9 rRNA copies/mL), and Neisseria gonorrhoeae (1E6 CFU/mL). Follow-up testing was conducted on samples containing the individual organisms from Pool #7. Reagents were tested on the PANTHER instrument at 2 replicates per control condition and four replicates per test condition. Mean normalized Ttimes are shown in Table 13 below.

Table 13

| Sample Type | FAM | HEX | ROX | Cy5.5 |
|---|---|---|---|---|
| Positive IVT control | 20.8 | 20.6 | 15.0 | . |
| M. curtisii 1E6 CFU_ML | . | . | . | . |
| M. genitalium 1E6 CFU_ML | 16.5 | . | . | . |
| M. hominis 1E6 CFU_ML | . | . | . | . |
| N. gonorrhoeae 1E6 CFU_ML | . | . | . | . |
| Negative control | . | . | . | . |

Unexpected FAM signal was observed only for M. genitalium. To determine which oligomers were responsible for the unexpected signal generation, an experiment was conducted in which an individual oligomer was omitted from the multiplex mixture for each condition. The multiplex utilized the oligomers in Table 12, with the omission of SEQ ID NO: 23. Each of the 8 reagent sets (a control condition containing all oligomers and seven conditions in which a single oligomer had been omitted) was tested in a manual RT-TMA format against specificity Pool #7 at three replicates per condition. Normalized FAM Ttimes are shown in Table 14 below.

TABLE 14

| Condition | Omitted | Rep 1 | Rep 2 | Rep 3 |
|---|---|---|---|---|
| All | none | 14.05 | 14.64 | 15.75 |
| L. crisp Torch | SEQ ID NO: 11 | 15.01 | 16.09 | 14.96 |
| L. gas Torch | SEQ ID NO: 259 | | | |
| Lacto T7 | SEQ ID NO: 10 | | | |
| A. vag T7 | SEQ ID NO: 18 | 15.05 | 15.43 | 14.59 |
| G. vag T7 | SEQ ID NO: 15 | 15.03 | 14.89 | 15.84 |
| A. vag NT7 | SEQ ID NO: 45 | | | |
| G. vag NT7 | SEQ ID NO: 14 | 14.89 | 15.10 | 15.24 |

This experiment indicated that SEQ ID NO:259, SEQ ID NO: 10, and SEQ ID NO: 45 are required for the unexpected FAM signal generation. To test sufficiency of these oligos for detection of M. genitalium on FAM, RT-TMA reagents were built in which these three oligomers (SEQ ID NO:259, SEQ ID NO:10, and SEQ ID NO:45) represented the only torch, promoter primer, and primer. M. genitalium was detected on FAM in all 4 replicates tested, whereas A. vag, G. vag, L. gas, and a negative control were not detected with this oligomer combination (see Table 15). This set of oligomers is therefore sufficient.

TABLE 15

| Sample | Mean RFU Range | Mean Ttime Norm |
|---|---|---|
| A. vag 1E7 copies/mL | −94 | . |
| G. vag 1E8 copies/mL | −209 | . |
| L. gas 1E6 CFU/mL | 156 | . |
| M. gen 1E6 CFU/mL | 13274 | 15.6 |
| No target | −65 | . |

The *M. genitalium* cross-reactivity risk for the multiplex described in Table 12 was not flagged in an initial bioinformatics assessment. SEQ ID NO: 10 and SEQ ID NO:259 did not meet the initial criteria for predicted hybridization to *M. genitalium*. The observed cross-reactivity was therefore unexpected.

Example 5

To increase A.vag sensitivity, multiplex testing was conducted in parallel with two A.vag systems: (1) a Lacto-A.vag-G.vag multiplex using a biphasic A.vag system with a long amplicon ("LAG-5"), and (2) a Lacto-A.vag-G.vag multiplex using a non-biphasic A.vag system with a short amplicon ("LAG-6"). These A. vag systems started with the oligos shown in Table 16.

TABLE 16

| Target | NT7 | Torch | T7 | TCO | Amplicon length |
|---|---|---|---|---|---|
| A. vag non biphasic | SEQ ID NO: 17 | SEQ ID NO: 212 | SEQ ID NO: 18 | SEQ ID NO: 13 | Short |
| A. vag biphasic | SEQ ID NO: 206 | SEQ ID NO: 84 | SEQ ID NO: 18 | SEQ ID NO: 13 | Long |

The A.vag biphasic system was too fast to provide a TTime from IVT-equivalent clinically relevant high concentrations of A.vag (≥1E11 cp/mL). Previously designed A.vag T7 oligos were rescreened. One T7 with a predicted secondary structure resulted in slower Ttimes.

Improvements to the A.vag non-biphasic system focused on improving the A.vag curve slopes. Multiple A.vag torch iterations were designed within the same region and screened in singleplex. A.vag Torch having the nucleotide sequence of SEQ ID NO:19 was selected due to the improvement in sensitivity in the multiplex context.

Analytical specificity results were similar between the two A.vag systems (LAG5 and LAG6).

The improved A. vag oligo sets are shown in Table 17 below.

TABLE 17

| Target | NT7 | Torch | T7 | TCO | Amplicon length |
|---|---|---|---|---|---|
| A. vag non biphasic | SEQ ID NO: 17 | SEQ ID NO: 19 | SEQ ID NO: 18 | SEQ ID NO: 13 | Short |
| A. vag biphasic | SEQ ID NO: 206 | SEQ ID NO: 84 | SEQ ID NO: 50 | SEQ ID NO: 13 | Long |

Clinical performance of LAG5 and LAG6 multiplex oligo combinations (differing in the A. vag design oligos as shown in Table 17 above) were compared on two small sets of vaginal clinical swab samples. Data were interpreted with two types of algorithm: a decision tree algorithm based on quantitation from L. crisp, G. vag, and A. vag standard curves as described in Example 6, and an uncalibrated Ttime ratio algorithm. In the uncalibrated Ttime ratio algorithm, specimens were called Positive if both of the two criteria were met (otherwise they were Negative): 1) the ratio of the internal control Ttime to either the G. vag Ttime or the A. vag Ttime exceeded a cutoff value, and 2) the ratio of the L. spp Ttime to either the G. vag Ttime or the A. vag Ttime exceeded a different cutoff value. Absent Ttimes were assigned a fixed value. Both LAG5 and LAG6 had similar clinical performance, however, LAG6 performed slightly better with the pre-established log c/mL cut-off values (Lacto 8.3, G.vag 10.5, and A.vag 7.4). The project moved forward using the LAG6 multiplex design, with all systems non-biphasic and the A. vag amplicon short.

Example 6

Oligomers having the nucleotide sequences shown in Table 18 were evaluated in a multiplex APTIMA® Bacterial Vaginosis (ABV) assay for amplification and detection of L. crispatus, L. *jensenii*, L. *gasseri*, G. *vaginalis*, and A. vaginae and a general internal control (GIC).

TABLE 18

| | Oligomer Sequences | | | |
|---|---|---|---|---|
| Target | NT7 | Torch | T7 | TCO |
| L. crispatus | SEQ ID NO: 7 | SEQ ID NO: 11 | | SEQ ID NO: 6 |
| L. jensenii | SEQ ID NO: 8 | | SEQ ID NO: 10 | |
| L. gasseri | SEQ ID NO: 9 | SEQ ID NO: 12 | | |
| G. vaginalis | SEQ ID NO: 14 | SEQ ID NO: 16 | SEQ ID NO: 15 | SEQ ID NO: 13 |
| A. vaginae | SEQ ID NO: 17 | SEQ ID NO: 19 | SEQ ID NO: 18 | |
| GIC | SEQ ID NO: 21 | SEQ ID NO: 23 | SEQ ID NO: 22 | SEQ ID NO: 20 |

Oligomers designed and screened for the Bacterial Vaginosis assay are shown in Table 34. Based on this screening, the oligomers shown in Table 16 were selected for further evaluation on the PANTHER® system for linearity, cross-reactivity, clinical performance, and strain inclusivity.

The following bulk liquid reagents were built:
1) TCR: HEPES Free Acid Dhihdrate (250 mM), Lithium Hydroxide Monohydrate (310 mM), Lithium Chloride (1.883 M), EDTA Free Acid (100 mM), Poly dT14 Mag Particles (0.03% w/v), Lithium Hydroxide and Hydrochloric acid to pH, and water to volume:
2) Enzyme: HEPES free acid (57.46 mM), EDTA free acid (0.98 mM), Triton X-100 (0.10 v/v), Potassium Chloride (49.61 mM), glycerol anhydrous (0.2 v/v), EDTA disodium dehydrate (0.39 mM), N-Acetyl-L-Cysteine (49.58 mM), D (+) Trehalose dehydrate (0.03 w/v), Cloned MMLV enzyme (224 MR/L), T7 RNA Polymerase enzyme (140 MU/L), water to volume:
3) Amplification and Promoter Reagent: Postassium chloride (23.3 mM), glycerol anhydrous (3.33%), zinc acetate dehydrate (0.05 mM), Pro clin 300 preservative (0.02%), Tween-20 (1%), Trizma base (11.61 mM), Trizma hydrochloride (14.94 mM), Magnesium chloride (31 mM), dATP (0.83 mM), dCTP (0.83 mM), dGTP (0.83 mM), dTTP (0.83 mM), ATP (7 mM), CTP (7 mM), GTP (7 mM), UTP (8 mM), water (to volume).

The Amp and Pro reagents from Table 19 were made by spiking oligonucleotides into aliquots of the amplification and promoter bulk reagent. The TCR reagent from Table 19 was made by spiking oligonucleotides and an internal control in vitro transcript into the TCR bulk reagent. No oligos were added to the enzyme reagent.

The surfactant Tween-20 was added to amp/promoter buffer to a final concentration of 1% in order to improve torch stability by reducing aggregation.

Testing was conducted on the PANTHER system and results were analyzed with in-house development software for interpretation of real-time curve properties.

TABLE 19

Reagent Formulation for Analytical and Clinical Testing

| Reagent | pmol/rxn | SEQ ID NO: | Type | Analyte |
|---|---|---|---|---|
| TCR | 10 | SEQ ID NO: 6 | TCO | *L. crisp, L. jen, L. gas* |
| TCR | 10 | SEQ ID NO: 13 | TCO | *G. vag, A. vag* |
| TCR | 2.5 | SEQ ID NO: 20 | TCO | GIC |
| Amp | 10 | SEQ ID NO: 7 | NT7 | *L. crisp* |
| Amp | 10 | SEQ ID NO: 8 | NT7 | *L. jen* |
| Amp | 10 | SEQ ID NO: 9 | NT7 | *L. gas* |
| Amp | 10 | SEQ ID NO: 14 | NT7 | *G. vag* |
| Amp | 7.5 | SEQ ID NO: 17 | NT7 | *A. vag* |
| Amp | 2.5 | SEQ ID NO: 21 | NT7 | GIC |
| Pro | 10 | SEQ ID NO: 10 | T7 | *L. crisp, L. jen, L. gas* |
| Pro | 5 | SEQ ID NO: 15 | T7 | *G. vag* |
| Pro | 7.5 | SEQ ID NO: 18 | T7 | *A. vag* |
| Pro | 2.5 | SEQ ID NO: 22 | T7 | GIC |
| Pro | 10 | SEQ ID NO: 11 | Torch | *L. crisp, L. jen* |
| Pro | 5 | SEQ ID NO: 12 | Torch | *L. gas* |
| Pro | 15 | SEQ ID NO: 16 | Torch | *G. vag* |
| Pro | 10 | SEQ ID NO: 19 | Torch | *A. vag* |
| Pro | 10 | SEQ ID NO: 23 | Torch | GIC |

Linearity/Dynamic Range Testing/Analytical Sensitivity

Linearity testing was conducted for each of the five assay targets (A.vag, G.vag, L.crisp, L.gas, and L.jen). For each analyte, two sets of panels were prepared. One panel was prepared by spiking culture lysates into Specimen Transport Medium, STM (sodium phosphate monobasic monohydrate (2.07 g/L), Lithium lauryl sulphate (30 g/L), EDTA disodium dehydrate (0.372 g/L), EGTA free acid (0.38 g/L), sodium phosphate dibasic (2.13 g/L)). The second panel was prepared by spiking in vitro transcript (IVT) into STM. Each panel was tested in five replicates on the PANTHER system. Panel concentrations are listed in Table 20.

TABLE 20

Culture Lysates and IVT Concentrations Tested

| | Clinical Lysate Conc. (CFU/mL) | IVT Concentration (c/mL) |
|---|---|---|
| *A. vag* | 1e7, 1e6, 1e5, 1e4, 1e3, 1e2 | 1e12, 1e11, 1e10, 1e9, 1e8, 1e7, 1e6, 1e5, 1e4 |
| *G. vag* | 1e7, 1e6, 1e5, 1e4, 1e3, 1e2 | 1e12, 1e11, 1e10, 1e9, 1e8, 1e7, 1e6 |
| *L. crisp* | 1e7, 1e6, 1e5, 1e4, 1e3, 1e2 | 1e12, 1e11, 1e10, 1e9, 1e8, 1e7, 1e6 |
| *L. gas* | 1e7, 1e6, 1e5, 1e4, 1e3, 1e2 | 1e12, 1e11, 1e10, 1e9, 1e8, 1e7, 1e6 |
| *L. jen* | 1e7, 1e6, 1e5, 1e4, 1e3, 1e2 | 1e12, 1e11, 1e10, 1e9, 1e8, 1e7, 1e6 |

TABLE 20-continued

Culture Lysates and IVT Concentrations Tested

| Clinical Lysate Conc. (CFU/mL) | IVT Concentration (c/mL) |
|---|---|

Note:
1e4 and 1e5 c/mL IVTs tested for *A. vag* only.

Table 21 shows a summary of percent positivity for all five analytes. A.vag and all three Lacto species have 100% IVT positivity down to 1E+07 c/mL. G.vag has 100% IVT positivity at 1E+08 c/mL. All lysates have 100% positivity at 1E+03 CFU/mL.

Detailed linearity results for all analytes are shown in Tables 22-26. Results shown include positivity, average RFU range, average Ttime, average Tslope, and standard deviation. All reactions were valid as indicated by the general internal control.

TABLE 21

Percent Positivity Results

| Panel | Concentration | N | *A. vag* | *G. vag* | *L. crisp* | *L. gas* | *L. jen* |
|---|---|---|---|---|---|---|---|
| Negative | 0 | 5 | 0% | 0% | 0% | 0% | 0% |
| IVT | 1E+12 c/mL | 5 | 100% | 100% | 100% | 100% | 100% |
| IVT | 1E+11 c/mL | 5 | 100% | 100% | 100% | 100% | 100% |
| IVT | 1E+10 c/mL | 5 | 100% | 100% | 100% | 100% | 100% |
| IVT | 1E+09 c/mL | 5 | 100% | 100% | 100% | 100% | 100% |
| IVT | 1E+08 c/mL | 5 | 100% | 100% | 100% | 100% | 100% |
| IVT | 1E+07 c/mL | 5 | 100% | 20% | 100% | 100% | 100% |
| IVT | 1E+06 c/mL | 5 | 20% | 0% | 60% | 0% | 0% |
| IVT | 1E+05 c/mL | 5 | 0% | NA | NA | NA | NA |
| IVT | 1E+04 c/mL | 5 | 0% | NA | NA | NA | NA |
| Lysate | 1E+07 CFU/mL | 5 | 100% | 100% | 100% | 100% | 100% |
| Lysate | 1E+06 CFU/mL | 5 | 100% | 100% | 100% | 100% | 100% |
| Lysate | 1E+05 CFU/mL | 5 | 100% | 100% | 100% | 100% | 100% |
| Lysate | 1E+04 CFU/mL | 5 | 100% | 100% | 100% | 100% | 100% |
| Lysate | 1E+03 CFU/mL | 5 | 100% | 100% | 100% | 100% | 100% |
| Lysate | 1E+02 CFU/mL | 5 | 0% | 0% | 100% | 40% | 100% |

TABLE 22

Results Summary for *A. vag*

| Panel | Concentration | N | N Positive | Positive % | Average RFU Range | Average Ttime | Average Tslope | StDev |
|---|---|---|---|---|---|---|---|---|
| Negative | 0 | 5 | 0 | 0% | 23 | — | — | — |
| IVT | 1E+12 c/mL | 5 | 5 | 100% | 5,677 | 9.52 | 0.12 | 0.23 |
| IVT | 1E+11 c/mL | 5 | 5 | 100% | 5,589 | 12.10 | 0.13 | 0.22 |
| IVT | 1E+10 c/mL | 5 | 5 | 100% | 5,637 | 14.27 | 0.12 | 0.25 |
| IVT | 1E+09 c/mL | 5 | 5 | 100% | 5,715 | 17.35 | 0.12 | 0.28 |
| IVT | 1E+08 c/mL | 5 | 5 | 100% | 5,438 | 19.89 | 0.10 | 0.29 |
| IVT | 1E+07 c/mL | 5 | 5 | 100% | 5,022 | 23.47 | 0.05 | 0.10 |
| IVT | 1E+06 c/mL | 5 | 1 | 20% | 1,160 | 26.03 | 0.04 | — |
| IVT | 1E+05 c/mL | 5 | 0 | 0% | 144 | — | — | — |
| IVT | 1E+04 c/mL | 5 | 0 | 0% | 8 | — | — | — |
| Lysate | 1E+07 CFU/mL | 5 | 5 | 100% | 5,760 | 12.32 | 0.13 | 0.15 |
| Lysate | 1E+06 CFU/mL | 5 | 5 | 100% | 5,546 | 14.88 | 0.12 | 0.21 |
| Lysate | 1E+05 CFU/mL | 5 | 5 | 100% | 5,602 | 17.71 | 0.11 | 0.31 |
| Lysate | 1E+04 CFU/mL | 5 | 5 | 100% | 5,540 | 20.63 | 0.10 | 0.38 |
| Lysate | 1E+03 CFU/mL | 5 | 5 | 100% | 4,779 | 24.18 | 0.05 | 0.45 |
| Lysate | 1E+02 CFU/mL | 5 | 0 | 0% | 170 | — | — | — |

TABLE 23

Results Summary for *G. vag*

| Panel | Concentration | N | N Positive | Positive % | Average RFU Range | Average Ttime | Average Tslope | StDev |
|---|---|---|---|---|---|---|---|---|
| Negative | 0 | 5 | 0 | 0% | −902 | — | — | — |
| IVT | 1E+12 c/mL | 5 | 5 | 100% | 3,011 | 12.30 | 0.11 | 0.06 |
| IVT | 1E+11 c/mL | 5 | 5 | 100% | 3,288 | 15.44 | 0.11 | 0.19 |
| IVT | 1E+10 c/mL | 5 | 5 | 100% | 2,955 | 18.63 | 0.11 | 0.10 |
| IVT | 1E+09 c/mL | 5 | 5 | 100% | 3,216 | 22.31 | 0.09 | 0.19 |
| IVT | 1E+08 c/mL | 5 | 5 | 100% | 3,135 | 26.66 | 0.06 | 1.15 |
| IVT | 1E+07 c/mL | 5 | 1 | 20% | 1,673 | 29.56 | 0.04 | — |
| IVT | 1E+06 c/mL | 5 | 0 | 0% | −64 | — | — | — |
| Lysate | 1E+07 CFU/mL | 5 | 5 | 100% | 3,195 | 13.92 | 0.10 | 0.24 |
| Lysate | 1E+06 CFU/mL | 5 | 5 | 100% | 3,112 | 17.56 | 0.11 | 0.14 |
| Lysate | 1E+05 CFU/mL | 5 | 5 | 100% | 3,158 | 20.87 | 0.10 | 0.38 |
| Lysate | 1E+04 CFU/mL | 5 | 5 | 100% | 3,147 | 24.63 | 0.08 | 0.50 |
| Lysate | 1E+03 CFU/mL | 5 | 5 | 100% | 2,738 | 30.42 | 0.05 | 1.06 |
| Lysate | 1E+02 CFU/mL | 5 | 0 | 0% | 572 | — | — | — |

TABLE 24

Results Summary for *L. crisp*

| Panel | Concentration | N | N Positive | Positive % | Average RFU Range | Average Ttime | Average Tslope | StDev |
|---|---|---|---|---|---|---|---|---|
| Negative | 0 | 5 | 0 | 0% | −22 | — | — | — |
| IVT | 1E+12 c/mL | 5 | 5 | 100% | 4,000 | 11.98 | 0.18 | 0.18 |
| IVT | 1E+11 c/mL | 5 | 5 | 100% | 4,098 | 13.78 | 0.17 | 0.09 |
| IVT | 1E+10 c/mL | 5 | 5 | 100% | 3,857 | 16.39 | 0.19 | 0.29 |
| IVT | 1E+09 c/mL | 5 | 5 | 100% | 3,882 | 18.58 | 0.15 | 0.16 |
| IVT | 1E+08 c/mL | 5 | 5 | 100% | 3,893 | 21.45 | 0.14 | 0.21 |
| IVT | 1E+07 c/mL | 5 | 5 | 100% | 3,702 | 24.55 | 0.10 | 0.57 |
| IVT | 1E+06 c/mL | 5 | 3 | 60% | 2,209 | 28.83 | 0.04 | 0.48 |
| Lysate | 1E+07 CFU/mL | 5 | 5 | 100% | 4,187 | 9.77 | 0.18 | 0.23 |
| Lysate | 1E+06 CFU/mL | 5 | 5 | 100% | 4,325 | 11.55 | 0.20 | 0.28 |
| Lysate | 1E+05 CFU/mL | 5 | 5 | 100% | 3,916 | 13.39 | 0.17 | 0.11 |
| Lysate | 1E+04 CFU/mL | 5 | 5 | 100% | 4,100 | 16.16 | 0.19 | 0.32 |
| Lysate | 1E+03 CFU/mL | 5 | 5 | 100% | 4,037 | 18.39 | 0.17 | 0.37 |
| Lysate | 1E+02 CFU/mL | 5 | 5 | 100% | 3,916 | 21.68 | 0.16 | 0.36 |

TABLE 25

Results Summary for *L. gas*

| Panel | Concentration | N | N Positive | Positive % | Average RFU Range | Average Ttime | Average Tslope | StDev |
|---|---|---|---|---|---|---|---|---|
| Negative | 0 | 5 | 0 | 0% | −22 | — | — | — |
| IVT | 1E+12 c/mL | 5 | 5 | 100% | 12,020 | 15.98 | 0.14 | 0.26 |
| IVT | 1E+11 c/mL | 5 | 5 | 100% | 12,368 | 18.04 | 0.12 | 0.15 |
| IVT | 1E+10 c/mL | 5 | 5 | 100% | 12,165 | 21.20 | 0.12 | 0.24 |
| IVT | 1E+09 c/mL | 5 | 5 | 100% | 11,161 | 25.43 | 0.09 | 0.41 |
| IVT | 1E+08 c/mL | 5 | 5 | 100% | 9,752 | 31.11 | 0.06 | 0.52 |
| IVT | 1E+07 c/mL | 5 | 5 | 100% | 3,423 | 34.66 | 0.04 | 0.82 |
| IVT | 1E+06 c/mL | 5 | 0 | 0% | 290 | — | — | — |
| Lysate | 1E+07 CFU/mL | 5 | 5 | 100% | 12,670 | 15.56 | 0.14 | 0.19 |
| Lysate | 1E+06 CFU/mL | 5 | 5 | 100% | 11,996 | 17.99 | 0.12 | 0.27 |
| Lysate | 1E+05 CFU/mL | 5 | 5 | 100% | 12,469 | 21.31 | 0.11 | 0.27 |
| Lysate | 1E+04 CFU/mL | 5 | 5 | 100% | 11,471 | 25.47 | 0.09 | 0.28 |
| Lysate | 1E+03 CFU/mL | 5 | 5 | 100% | 9,338 | 30.58 | 0.06 | 0.26 |
| Lysate | 1E+02 CFU/mL | 5 | 2 | 40% | 3,002 | 35.40 | 0.04 | 0.23 |

TABLE 26

Results Summary for *L. jen*

| Panel | Concentration | N | N Positive | Positive % | Average RFU Range | Average Ttime | Average Tslope | StDev |
|---|---|---|---|---|---|---|---|---|
| Negative | 0 | 5 | 0 | 0% | −22 | — | — | — |
| IVT | 1E+12 c/mL | 5 | 5 | 100% | 3,849 | 13.91 | 0.14 | 0.06 |
| IVT | 1E+11 c/mL | 5 | 5 | 100% | 3,616 | 16.05 | 0.16 | 0.10 |
| IVT | 1E+10 c/mL | 5 | 5 | 100% | 3,688 | 18.26 | 0.14 | 0.16 |
| IVT | 1E+09 c/mL | 5 | 5 | 100% | 3,820 | 21.89 | 0.13 | 0.41 |
| IVT | 1E+08 c/mL | 5 | 5 | 100% | 3,777 | 25.51 | 0.12 | 0.43 |
| IVT | 1E+07 c/mL | 5 | 5 | 100% | 3,505 | 31.70 | 0.07 | 0.66 |
| IVT | 1E+06 c/mL | 5 | 0 | 0% | 998 | — | — | — |
| Lysate | 1E+07 CFU/mL | 5 | 5 | 100% | 3,736 | 13.13 | 0.15 | 0.11 |
| Lysate | 1E+06 CFU/mL | 5 | 5 | 100% | 3,824 | 15.18 | 0.15 | 0.18 |
| Lysate | 1E+05 CFU/mL | 5 | 5 | 100% | 3,729 | 17.73 | 0.14 | 0.13 |
| Lysate | 1E+04 CFU/mL | 5 | 5 | 100% | 3,666 | 20.98 | 0.14 | 0.29 |
| Lysate | 1E+03 CFU/mL | 5 | 5 | 100% | 3,798 | 24.77 | 0.11 | 0.30 |
| Lysate | 1E+02 CFU/mL | 5 | 5 | 100% | 3,128 | 30.16 | 0.06 | 0.51 |

Cross-reactivity to Microorganisms-Neat (Analytical Specificity) and Spiked (Inhibition) Testing Seventeen pools consisting of bacterial or yeast material, representing normal flora in the urogenital tract or closely related organisms to the APTIMA BV targets were built to support cross-reactivity testing (see Table 27). The concentration of each organism was targeted at 1.00E+06 CFU/mL or cell equivalent/mL, which is at the high end of or above expected concentrations.

Pools were tested neat (not spiked with assay targets) to confirm analytical specificity. Pools were also tested spiked with lysates representing each of the assay targets (A.vag, G.vag and all three Lacto lysates) to test for assay inhibition by other microorganisms. Each condition was tested in five replicates.

TABLE 27

Cross-reactivity Panel Members

| Pool # | Organism | Conc. | Units |
|---|---|---|---|
| 1 | *Acinetobacter iwoffii* | 1.00E+06 | CFU/mL |
|  | *Actinomyces israelii* | 5.00E+09 | rRNA c/ml |
|  | *Alcaligenes faecalis* | 1.00E+06 | CFU/mL |
|  | *Bacteroides fragilis* | 1.00E+06 | CFU/mL |
| 2 | *Bifidobacterium adolescentis* | 1.00E+06 | CFU/mL |
|  | *Campylobacter jejuni* | 1.00E+06 | CFU/mL |
|  | *Chlamydia trachomatis* | 1.00E+05 | IFU/ml |
| 3 | *Clostridium difficile* | 1.00E+06 | CFU/mL |
|  | *Corynebacterium genitalium* | 1.00E+06 | CFU/mL |
|  | *Cryptococcus neoformans* | 1.00E+06 | CFU/mL |
|  | *Eggerthella lenta* | 1.00E+06 | CFU/mL |
| 4 | *Enterobacter cloacae* | 1.00E+06 | CFU/mL |
|  | *Enterococcus faecalis* | 1.00E+06 | CFU/mL |
|  | *Escherichia coli* | 1.00E+06 | CFU/mL |
|  | *Fusobacterium nucleatum* | 1.00E+06 | CFU/mL |
| 5 | *Haemophilus ducreyi* | 1.00E+06 | CFU/mL |
|  | *Klebsiella pneumoniae* | 1.00E+06 | CFU/mL |
|  | *Listeria monocytogenes* | 1.00E+06 | CFU/mL |
|  | *Lactobacillus mucosae* | 1.00E+06 | CFU/mL |
| 6 | *Leptotrichia bucalis* | 1.00E+06 | CFU/mL |
|  | *Mobiluncus curtisii* | 5.00E+09 | rRNA c/ml |
|  | *Mycoplasma genitalium* | 1.00E+06 | CFU/mL |
|  | *Mycoplasma hominis* | 5.00E+09 | rRNA c/ml |
| 7 | *Neisseria gonorrhoeae* | 1.00E+06 | CFU/mL |
|  | *Peptostreptococcus magnus* | 1.00E+06 | CFU/mL |
|  | *Prevotella bivia* | 1.00E+06 | CFU/mL |
|  | *Propionibacterium acnes* | 1.00E+06 | CFU/mL |

TABLE 27-continued

Cross-reactivity Panel Members

| Pool # | Organism | Conc. | Units |
|---|---|---|---|
| 8 | Proteus vulgaris | 1.00E+06 | CFU/mL |
|  | Staphylococcus aureus | 1.00E+06 | CFU/mL |
|  | Staphylococcus epidermidis | 1.00E+06 | CFU/mL |
|  | Streptococcus agalactiae | 1.00E+06 | CFU/mL |
| 9 | Streptococcus pyogenes | 1.00E+06 | CFU/mL |
|  | Trichomonas vaginalis | 1.00E+05 | Cells/mL |
|  | Ureaplasma Parvum | 1.00E+06 | CFU/mL |
|  | Ureaplasma urealyticum | 1.00E+06 | CFU/mL |
| 10 | Herpes simplex virus I | 1.00E+04 | TCID50/mL |
|  | Herpes simplex virus II | 1.00E+04 | TCID50/mL |
|  | HIV | 1.00E+06 | copies/mL |
| 11 | Candida dubliniensis | 1.00E+06 | CFU/mL |
|  | Candida albicans | 1.00E+06 | CFU/mL |
|  | Candida glabrata | 1.00E+06 | CFU/mL |
|  | Candida parapsilosis | 1.00E+06 | CFU/mL |
| 12 | Candida tropicalis | 1.00E+06 | CFU/mL |
|  | Candida krusei | 1.00E+06 | CFU/mL |
|  | Candida lusitaniae | 1.00E+06 | CFU/mL |
| 13 | Atopobium minutum | 5.00E+09 | rRNA c/ml |
|  | Atopobium rimae | 5.00E+09 | rRNA c/ml |
|  | Atopobium parvulum | 5.00E+09 | rRNA c/ml |
| 14 | Lactobacillus iners | 1.00E+06 | CFU/mL |
| 15 | Bifidobacterium breve | 1.00E+06 | CFU/mL |
| 16 | Lactobacillus acidophilus | 1.00E+06 | CFU/mL |
| 17 | HeLa Cells | 1.00E+04 | Cells/mL |
|  | SiHa Cells | 1.00E+04 | Cells/mL |

Neat Cross-Reactivity Results

The FAM channel (Lacto species) gave a positive signal for Pool #16 (Lacto acidophilus). This positive result was expected due to the substantial sequence identity of the test organism to L.crisp. This cross-reactivity is acceptable as *L. acidophilus* is found in the upper gastrointestinal tract and is not likely to exist in the vaginal flora.

The HEX channel (G.vag) gave negative results for all seventeen panels.

The ROX channel (A.vag) gave positive signal for Pool #13 (Atopobium species). The three Atopobium species (A.rimae, A.minimum, *A.parvulum*) that comprise Pool #13 were separated and retested. Component testing showed that all three Atopobium species gave positive signals in the ROX channel.

The Cy5.5 channel (GIC) gave positive results for all seventeen pools.

Spiked Cross-Reactivity Results

The target assay analytes (L.crisp, L.jen, L.gas, A.vag, or G.vag) were spiked into each of the seventeen pools from Table 27. The positive analytes were spiked at approximately 3xLOD concentrations and tested in five replicates per panel per pool. The analyte spike concentrations are shown in Table 28. Spiked STM (Pool 0) was tested as a control for comparison.

TABLE 28

Spike Concentrations for Positive Cross-reactivity Panels

| | L. crisp CFU/mL | A. vag CFU/mL | G. vag CFU/mL | L. jen CFU/mL | L. gas CFU/mL |
|---|---|---|---|---|---|
| Panel 1 | 3.00E+02 | 1.00E+03 | — | — | — |
| Panel 2 | — | — | 1.00E+04 | 1.00E+03 | — |
| Panel 3 | — | — | — | — | 1.00E+03 |

One set of bulk reagents was built for the spiked cross-reactivity testing. The bulk reagents were aliquoted into three 100-test reagent kits for testing. Individual bottles of enzyme were reconstituted separately for each of the three kits. When the Ttime results were plotted, Reagent Kit #2 was found to have slower Ttimes for all four channels when compared to Reagent Kits #1 and #3. This likely occurred due to recon variability from the enzyme and therefore represents variance that may occur due to kit-to-kit variability. Dividing the analyte Ttime by the GIC Ttime, normalizes data to account for kit-to-kit variability. Ttime results are listed in Table 29.

The FAM channel (Lacto species) showed faster Ttime results from L.crisp, L.jen, and L. gas in the presence of Pool #16 (*L. acidophilus*) and slightly delayed Ttimes for Pool #06 (L.bucalis. M.*curtisii*. M.*genitalium*. M.*hominis*) when compared to the control (Pool #0). Pool #16 also showed cross-reactivity during neat testing and was expected due to the closely related nature of the test organism to L.crisp in the 16S design region. Pool #06 was divided into subcomponents and retested. Retesting showed a 1.6 minute delay in L.gas Ttimes in the presence of *M.hominis*.

The HEX channel (G.vag) showed a loss in sensitivity in 4 out of 5 replicates when tested in the presence of Pool #12 (*Candida tropicalis. krusei.* and *lusitaniae*). The three *Candida* species that comprise Pool #12 were separated and retested. Component testing showed that *C.krusei* caused the loss in sensitivity. This potential interference should be noted as *C.krusei* is found in the vaginal flora, but is not common. (In the U.S. clinical study for the BD Max™ Vaginal panel the *C.krusei* rate was 4/1647, or 0.2%, BD PI ref 443710).

The ROX channel (A.vag) showed slightly faster Ttimes for Pool #13 (Atopobium species) when compared to the control (Pool 0). This is the same pool that caused cross reactivity in the neat testing and was expected due to the closely related nature of the test organisms to the APTIMA BV target, A.vag.

The Cy5.5 channel (GIC) showed slightly delayed Ttimes for Pool #6 (L.bucalis. M.*curtisii*. M.*genitalium*. M.*hominis*). Component testing of these four microorganisms shows that the *M.hominis* delays GIC Ttimes by just over 1 minute and slightly changes the GIC emergence curve shape. *Mycoplasma hominis* is commonly found in BV subjects. Using the BV multivariate algorithm described in Example 1. Ttime delays of the GIC raise the BV score through the IC ratio term, thus increasing the probability of a BV positive call. This can mitigate the effect of reaction inhibition caused by the presence of organisms associated with BV. including *M.hominis*.

| Sample | FAM (*Lacto* species) | | | HEX (*G. vag*) | | | ROX (*A. vag*) | | | Cy5.5 (GIC) | | |
|---|---|---|---|---|---|---|---|---|---|---|---|---|
| Type | Panel 1 | Panel 2 | Panel 3 | Panel 1 | Panel 2 | Panel 3 | Panel 1 | Panel 2 | Panel 3 | Panel 1 | Panel 2 | Panel 3 |
| Pool 00 | 18.65 | 21.30 | 22.81 | . | 28.27 | . | 19.73 | . | . | 20.07 | 19.62 | 19.38 |
| Pool 01 | 18.62 | 21.56 | 22.94 | . | 28.95 | . | 20.11 | . | . | 20.32 | 19.78 | 19.56 |
| Pool 02 | 18.57 | 21.23 | 22.79 | . | 27.97 | . | 19.80 | . | . | 19.95 | 19.94 | 19.56 |
| Pool 03 | 18.32 | 21.26 | 23.16 | . | 28.55 | . | 19.86 | . | . | 19.77 | 19.55 | 19.46 |
| Pool 04 | 18.76 | 21.16 | 22.47 | . | 28.36 | . | 19.98 | . | . | 20.05 | 19.70 | 19.32 |
| Pool 05 | 18.35 | 21.18 | 22.83 | . | 27.44 | . | 19.00 | . | . | 19.83 | 19.33 | 19.53 |
| Pool 06 | 18.86 | 22.12[2] | 24.65[2] | . | 30.81 | . | 19.60 | . | . | 21.51[5] | 21.76[5] | 21.51[5] |
| Pool 07 | 18.42 | 21.39 | 22.64 | . | 28.25 | . | 19.14 | . | . | 19.69 | 19.25 | 19.15 |
| Pool 08 | 18.34 | 21.18 | 22.62 | . | 27.84 | . | 18.92 | . | . | 19.56 | 19.49 | 19.32 |
| Pool 09 | 18.64 | 21.57 | 23.21 | . | 28.44 | . | 19.64 | . | . | 19.78 | 19.46 | 19.35 |
| Pool 10 | 18.41 | 21.08 | 22.76 | . | 27.48 | . | 18.99 | . | . | 19.57 | 19.25 | 19.20 |
| Pool 11 | 18.51 | 21.12 | 26.66 | . | 27.06 | . | 19.07 | . | . | 19.79 | 19.50 | 22.28 |
| Pool 12 | 21.82 | 24.86 | 26.83 | . | 30.29[3] | . | 22.21 | . | . | 22.72 | 22.60 | 22.02 |
| Pool 13 | 22.11 | 24.43 | 26.61 | . | 31.56 | . | 21.01[4] | 21.20[4] | 21.33[4] | 22.67 | 22.00 | 22.01 |
| Pool 14 | 21.45 | 24.40 | 26.14 | . | 31.67 | . | 21.85 | . | . | 22.10 | 22.07 | 21.93 |
| Pool 15 | 21.73 | 24.22 | 26.20 | . | 31.56 | . | 22.15 | . | . | 22.12 | 21.89 | 21.95 |
| Pool 16 | 18.47[1] | 18.51[1] | 19.26[1] | . | 33.46 | . | 22.17 | . | . | 23.13 | 23.30 | 22.79 |
| Pool 17 | 21.96 | 24.16 | 26.30 | . | 31.40 | . | 21.95 | . | . | 22.44 | 21.81 | 21.98 |

[1] Faster FAM Ttimes in the presence of Pool #16 (*L. acidophilus*)
[2] Slightly slower FAM Ttimes in the presence of Pool #06 (*M. hominis*)
[3] 1/5 replicates positive in HEX in the presence of Pool #12 (*C. krusei*)
[4] Faster ROX Ttimes for Pool #13 (*Atopobium* species) and cross-reaction in panels 2 and 3.
[5] Slightly delayed Ttimes in the presence of Pool #06 (*M. hominis*)

Assessment of Clinical Samples

Clinical specimen testing was conducted with a set of 100 clinical vaginal swab specimens collected in STM. Samples from symptomatic women from 10 clinical sites were tested with the APTIMA BV assay on the PANTHER instrument. One replicate was tested per sample.

Clinical samples were run along with 20 calibrators (5 single-analyte calibrator levels for L.crisp, A.vag, and G.vag and 5 mixed-analyte calibrator levels containing all three analytes). Each single-analyte calibrator was tested in four replicates; each mixed-analyte calibrator was tested in five replicates.

Of 100 clinical specimen replicates tested, 93 replicates were valid. The remaining 7 replicates were invalid due to insufficient sample volume.

Clinical sample quantification was calculated based on L.crisp, G.vag. and A.vag standard curves.

Diagnosis of BV status was based on a quantitation and decision tree algorithm. The decision tree algorithm can be summarized as follows (where L, A, and G are the measured LogCopy values for L.crisp, A.vag, and G.vag, respectively; and X, Y, and Z are the cutoff values for L.crisp, A.vag, and G.vag, respectively): if L>X, then BV Negative: if not, then if A>Y or G>Z, then BV Positive, otherwise BV Negative. In this analysis, the following cutoff values were used for L.crisp. G.vag. and A.vag, respectively: 8.3, 10.4 and 7.4 log c/mL.

The clinical reference standard used in this example is Nugent score with intermediates determined by 3 of 4 Amsel criteria.

The single-analyte and mixed-analyte calibrators gave identical sensitivity results (90.2%) and similar specificity results (88.5% and 86.5%, respectively), with one sample changing call due to quantitation differences (see Table 30).

TABLE 30

Clinical Specimen Results

| | Single-Analyte Calibrator | Mixed-Analyte Calibrator |
|---|---|---|
| True Negative | 46 | 45 |
| False Positive | 6 | 7 |
| True Positive | 37 | 37 |
| False Negative | 4 | 4 |
| Sensitivity | 90.2% | 90.2% |
| Specificity | 88.5% | 86.5% |

Inclusivity Testing

Inclusivity testing was done with one control strain and all available polymorphic IVT strains for each of the five assay targets. Testing was done with a low and mid concentration of each strain. Low panel results were used to determine the effect of the polymorphisms on analyte sensitivity and mid panel results were analyzed to determine the effect of the polymorphisms on analyte Ttimes.

Table 31 details the number of strains tested as well as the low and high concentrations targeted for each analyte. Results are shown in Table 32.

A.vag showed a loss in sensitivity at the low copy level for three of the four polymorphism strains tested. The mid copy level showed a 2-3.5 minute Ttime delay for two of the four strains. The two strains that showed Ttime delays have two mismatches to the A.vag T7 oligo. The two strains that showed Ttime delays have a prevalence of 21.95% and <4.87%.

G.vag showed no loss in sensitivity for the polymorphic strain tested. At the mid copy level, the polymorphic strain showed slightly more than a 2 minute Ttime delay. This polymorphism has one mismatch in the TCO and one mismatch in the T7. This G.vag strain has a very low prevalence (2.04%).

L.crisp showed only a slight loss in sensitivity at the low copy level for one of the two polymorphic strains tested. Both polymorphic strains showed a difference in Ttime. When compared to the control, one strain resulted in a faster Ttime by 3.5 minutes while the other resulted in a slower Ttime by 2 minutes. These strains both have two mismatches to T7 and both have a prevalence<2%.

L.gas had 100% sensitivity for all strains tested. The mid copy level showed minimal change in Ttime for the polymorphic strains as compared to the control.

L.jen had 100% sensitivity for all strains tested. The mid copy level showed minimal change in Ttime for the polymorphic strains as compared to the control.

TABLE 31

Inclusivity Testing

| | # Control Strains | # Polymophic Strains | Low Conc. (c/mL) | Mid Conc. (c/mL) |
|---|---|---|---|---|
| A. vag | 1 | 4 | 1.00E+07 | 1.00E+09 |
| G. vag | 1 | 1 | 1.00E+08 | 1.00E+10 |
| L. crisp | 1 | 2 | 1.00E+06 | 1.00E+08 |
| L. gas | 1 | 2 | 1.00E+07 | 1.00E+09 |
| L. jen | 1 | 2 | 1.00E+07 | 1.00E+09 |

TABLE 32

IVT Strain Variants

| Analyte | Variant | Low Panel % Reactive | Mid Panel Ttime | Clone ID | Description of Variant | N pos | total N | Prevalence (%) |
|---|---|---|---|---|---|---|---|---|
| A. vag | Control | 100% | 18.11 | 100485 | | 32 | 41 | 78.05 |
| | 7gc | 0% | 20.18 | 100930 | 2 mismatches to T7 (−15/−16) | 9 | 41 | 21.95 |
| | 7tg | 0% | 21.71 | 100931 | 2 mismatches to T7 (−8/−15) | <2* | 41 | <4.87 |
| | Nc | 80% | 18.71 | 100929 | 1 mismatch to NT7 (19) | <2* | 41 | <4.87 |
| | Nt | 100% | 18.43 | 100928 | 1 mismatch to NT7 (3) | 9 | 41 | 21.95 |
| G. vag | Control | 100% | 19.91 | 100487 | | 144 | 147 | 97.96 |
| | Tt7c | 100% | 22.12 | 100879 | 2 mismatches to T7 (−27/−47) | 3 | 147 | 2.04 |
| L. crisp | Control | 100% | 22.30 | 100486 | | 248 | 253 | 98.02 |
| | 7ct | 100% | 18.82 | 100885 | 1 mismatch to T7 (−4) | 3 | 253 | 1.19 |
| | 7tc | 80% | 24.12 | 100884 | 1 mismatch to T7 (v9) | 2 | 253 | 0.79 |
| L. gas | Control | 100% | 20.35 | 100497 | 1 mismatch to NT7 (8) | 220 | 331 | 66.47 |
| | Ng7t | 100% | 20.54 | 100881 | NT7 | 102 | 331 | 30.82 |
| | | | | | T7 | 361 | 381 | 94.75 |
| | Ng7c | 100% | 20.20 | 100880 | 1 mismatch to T7 (−9) | 18 | 381 | 4.72 |
| | Control | 100% | 22.69 | 100498 | 1 mismatch to NT7 (13) | 18 | 81 | 22.22 |
| L. jen | Nc7a | 100% | 23.56 | 100882 | 1 mismatch to T7 (−13) | <2* | 98 | <2.04 |
| | Nc7g | 100% | 23.00 | 100883 | NT7 | 63 | 81 | 77.78 |
| | | | | | T7 | 98 | 98 | 100.00 |

*Variants were not identified in Bioinformatics in silico analysis. This indicates there were fewer than 2 instances identified.

Sequences

TABLE 33

Bacterial Reference Sequences

| SEQ ID NO: | Description | Sequence |
|---|---|---|
| 1 | Lactobacillus crispatus strain ATCC 33820 16S ribosomal RNA gene | gacgaacgctggcggcgtgcctaatacatgcaagtcgagcgagcgga actaacagatttacttcggtaatgacgttaggaaagcgagcggcgga tgggtgagtaacacgtggggaacctgccccatagtctgggataccac ttggaaacaggtgctaataccggataagaaagcagatcgcatgatca gcttttaaaaggcggcgtaagctgtcgctatgggatggccccgcggt gcattagctagttggtaaggtaaaggcttaccaaggcgatgatgcat agccgagttgagagactgatcggccacattgggactgagacacggcc caaactcctacgggaggcagcagtagggaatcttccacaatggacgc aagtctgatggagcaacgccgcgtgagtgaagaaggttttcggatcg taaagctctgttgttggtgaagaaggatagaggtagtaactggcctt tatttgacggtaatcaaccagaaagtcacggctaactacgtgccagc agccgcggtaatacgtaggtggcaagcgttgtccggatttattgggc |

TABLE 33-continued

Bacterial Reference Sequences

| SEQ ID NO: | Description | Sequence |
|---|---|---|
| | | gtaaagcgagcgcaggcggaagaataagtctgatgtgaaagccctcg gcttaaccgaggaactgcatcggaaactgttttcttgagtgcagaa gaggagagtggaactccatgtgtagcggtggaatgcgtagatatatg gaagaacaccagtggcgaaggcggctctctggtctgcaactgacgct gaggctcgaaagcatgggtagcgaacaggattagataccctggtagt ccatgccgtaaacgatgagtgctaagtgttgggaggtttccgcctct cagtgctgcagctaacgcattaagcactccgcctggggagtacgacc gcaaggttgaaactcaaaggaattgacggggcccgcacaagcggtg gagcatgtggtttaattcgaagcaacgcgaagaaccttaccaggtct tgacatctagtgccatttgtagagatacaaagttcccttcggggacg ctaagacaggtggtgcatggctgtcgtcagctcgtgtcgtgagatgt tgggttaagtcccgcaacgagcgcaacccttgttattagttgccagc attaagttgggcactctaatgagactgccggtgacaaaccggaggaa ggtggggatgacgtcaagtcatcatgccccttatgacctgggctaca cacgtgctacaatgggcagtacaacgagaagcgagcctgcgaaggca agcgaatctctgaaagctgttctcagttcggactgcagtctgcaact cgactgcacgaagctggaatcgctagtaatcgcggatcagcacgccg cggtgaatacgttcccgggccttgtacacaccgcccgtcacaccatg ggagtctgcaatgcccaaagccggtggcctaaccttcgggaaggagc cgtctaaggcagggcagatgactggggtgaagtcgtaacaaggtagc cgtaggagaactgc |
| 2 | Lactobacillus jensenii strain ATCC 25258 16S ribosomal RNA gene | tgcctaatacatgcaagtcgagcgagcttgcctatagaagttcttcg aatggaaatagatacaagctagcggcggatgggtgagtaacgcgtg ggtaacctgcccttaagtctgggataccatttggaaacagatgctaa taccggataaaagctactttcgcatgaaagaagtttaaaaggcggcg taagctgtcgtaaaggatggacttgcgatgcattagctagttggtaa ggtaacggcttaccaaggctgatgatgcatagccgagttgagagact gatcggccacattgggactgagacacggcccaaactcctacgggagg cagcagtagggaatcttccacaatggacgaaagtctgatggagcaac gccgcgtgagtgaagaaggttttcggatcgtaaagctctgttgttgg tgaagaaggatagaggtagtaactggcctttatttgacggtaatcaa ccagaaagtcacggctaactacgtgccagcagccgcggtaatacgta ggtggcaagcgttgtccggatttattgggcgtaaagcgagcgcaggc ggattgataagtctgatgtgaaagccttcggctcaaccgaagaactg catcagaaactgtcaatcttgagtgcagaagaggagagtggaactcc atgtgtagcggtggaatgcgtagatatatggaagaacaccagtggcg aaggcggctctctggtctgtaactgacgctgaggctcgaaagcatgg gtagcgaacaggattagataccctggtagtccatgccgtaaacgatg agtgctaagtgttgggaggtttccgcctctcagtgctgcagctaacg cattaagcactccgcctggggagtacgaccgcaaggttgaaactcaa aggaattgacggggcccgcacaagcggtggagcatgtggtttaatt cgaagcaacgcgaagaaccttaccaggtcttgacatcctttgaccac ctaagagattaggttttcccttcggggacaaagagacaggtggtgca tggctgtcgtcagctcgtgtcgtgagatgttgggttaagtcccgcaa cgagcgcaacccttgttaatagttgccagcattaagttgggcactct attgagactgccggtgacaaaccggaggaaggtggggatgacgtcaa gtcatcatgccccttatgacctgggctacacacgtgctacaatgggc agtacaacgagaagcgaacctgtgaaggcaagcggatctcttaaagc tgttctcagttcggactgtaggctgcaactcgcctacacgaagctgg aatcgctagtaatcgcggatcagcacgccgcggtgaatacgttcccg ggccttgtacacaccgcccgtcacaccatgagagtttgtaacaccca aagtcggtgaggtaacctttggagccagccgcctaaggtgggacaga tgattagggtgaagtcgtaacaaggtagccgtaggagaa |
| 3 | Lactobacillus gasseri strain ATCC 33323 16S ribosomal RNA gene | aaaatgagagtttgatcctggctcaggacgaacgctggcggcgtgcc taatacatgcaagtcgagcgagcttgcctagtagaatttggtgcttg caccagatgaaactagatacaagcgagcggcggacgggtgagtaaca cgtgggtaacctgcccaagagactgggataacacctggaaacagatg ctaataccggataacaacactagacgcatgtctagagtttaaaagat ggttctgctatcactcttggatgacctgcggtgcattagctagttg gtaaggtaacggcttaccaaggcaatgatgcatagccgagttgagag actgatcggccacattgggactgagacacggcccaaactcctacggg aggcagcagtagggaatcttccacaatggacgcaagtctgatggagc aacgccgcgtgagtgaagaagggtttcggctcgtaaagctctgttgg tagtgaagaaagatagaggtagtaactggcctttatttgacggtaat tacttagaaagtcacggctaactacgtgccagcagccgcggtaatac gtaggtggcaagcgttgtccggatttattgggcgtaaagcgagtgca ggcggttcaataagtctgatgtgaaagccttcggctcaaccggagaa ttgcatcagaaactgttgaacttgagtgcagaagaggagagtggaac tccatgtgtagcggtggaatgcgtagatatatggaagaacaccagtg gcgaaggcggctctctggtctgcaactgacgctgaggctcgaaagca tgggtagcgaacaggattagataccctggtagtccatgccgtaaacg atgagtgctaagtgttgggaggtttccgcctctcagtgctgcagcta |

TABLE 33-continued

Bacterial Reference Sequences

| SEQ ID NO: | Description | Sequence |
|---|---|---|
|  |  | acgcattaagcactccgcctggggagtacgaccgcaaggttgaaact caaaggaattgacgggggcccgcacaagcggtggagcatgtggttta attcgaagcaacgcgaagaaccttaccaggtcttgacatccagtgca aacctaagagattaggtgttcccttcgggacgctgagacaggtggt gcatggctgtcgtcagctcgtgtcgtgagatgttgggttaagtcccg caacgagcgcaaccettgtcattagttgccatcattaagttgggcac tctaatgagactgccggtgacaaaccggaggaaggtggggatgacgt caagtcatcatgcccttatgacctgggctacacacgtgctacaatg gacggtacaacgagaagcgaacctgcgaaggcaagcggatctctgaa agccgttctcagttcggactgtaggctgcaactcgcctacacgaagc tggaatcgctagtaatcgcggatcagcacgccgcggtgaatacgttc ccgggccttgtacacaccgcccgtcacaccatgagagtctgtaacac ccaaagccggtgggataacctttataggagtcagccgtctaaggtag gacagatgattagggtgaagtcgtaacaaggtagccgtaggagaacc tgcggctggatcacctcctttt |
| 4 | *Atopobium vaginae* 16S ribosomal RNA gene, partial sequence | gatgaacgctggcggcgcgcctaacacatgcaagtcgaacggttaaa gcatcttcggatgtgtataaagtggcgaacggctgagtaacacgtgg gcaacctgcccttttgcactgggatagcctcgggaaaccgaggttaat accggatactccatatttgtcgcatggcgaatatgggaaagctccgg cggcaaaggatgggcccgcggcctgttagctagttggtggggtagtg gcctaccaaggcaatgatgggtagccgggttgagagaccgaccggcc agattgggactgagacacggcccagactcctacgggaggcagcagtg gggaatcttgcacaatgggcgaaagcctgatgcagcgacgccgcgtg cgggatgaaggccttcgggttgtaaaccgctttcagcagggacgagg ccgcaaggtgacggtacctgcagaagaagccccggctaactacgtgc cagcagccgcggtaatacgtaggggcaagcgttatccggattcatt gggcgtaaagcgcgcgtaggcggtctgttaggtcaggagttaaatct gggggctcaaccccctatccgctcctgataccggcaggcttgagtctg gtagggaagatggaattccaagtgtagcggtgaaatgcgcagatat ttggaagaacaccggtggcgaaggcggtcttctgggccatgactgac gctgaggcgcgaaagctagggagcgaacaggattagataccctggt agtcctagctgtaaacgatggacactaggtgtggggagattatactt tccgtgccgcagctaacgcattaagtgtcccgcctggggagtacggt cgcaagactaaaactcaaaggaattgacgggggcccgcacaagcagc ggagcatgtggcttaattcgaagcaacgcgaagaaccttaccaggcc ttgacatttaggtgaagcagtggaaacactgtggccgaaaggagcct aaacaggtggtgcatggctgtcgtcagctcgtgtcgtgagatgttgg gttaagtcccgcaacgagcgcaacccttgtcgcatgttgccagcggt tcggccgggcacccatgcgagaccgccggcgttaagccggaggaagg tggggacgacgtcaagtcatcatgccccttatgtcctgggctgcaca cgtgctacaatggccggcacagagggctgctactgcgcgagcagaag cgaatccctaaagccggtcccagttcggattggaggctgcaactcgc ctccatgaagtcggagttgctagtaatcgcggatcagcacgccgcgg tgaatgcgttcccgggccttgtacacaccgcccgtcacaccacccga gtcgtctgcacccgaagtcgtcggcctaacccgcaagggagggaggc gccgaaggtgtggagggtaaggggggt |
| 5 | *Gardnerella vaginalis* strain 594 16S ribosomal RNA gene | tttcgtggagggttcgattctggctcaggatgaacgctggcggcgtg cttaacacatgcnagtcgaacgggatctgaccagcttgctggttggt gagagtggcgaacgggtgagtaatgcgtgaccaacctgccccatgct ccagaatagctcttggaaacgggtggtaatgctggatgctccaactt gacgcatgtcttgttgggaaagtgtttagtggcatgggatgggtcg cgtcctatcagcttgtaggcgggtaatggcccacctaggcttcgac gggtagccggcctgagagggcggacggccacattgggactgagatac ggcccagactnctacgggaggcagcagtggggaatattgcgcaatgg gggaaaccctgacgcagcgacgncgcgtgcgggatgaaggccttcgg gttgtaaaccgcttttgattgggagcaagccttttgggtgagtgtac ctttcgaataagcgccggctaactacgtgccagcagccgcggtaata cgtagggcgcaagcgttatccggaattattgggcgtaaagagcttgt aggcggttcgtcgcgtctggtgtgaaagcccatcgcttaacggtgg nttgcgccgggtacgggcgggctagagtgcagtaggggagactggaa ttctcggtgtaacggtggaatgtgtagatatcgggaagaacaccaat ggcgaaggcaggtctctgggctgttactgacgctgagaagcgaaagc gtgggagcgaacaggattagataccctggtagtccacgccgtaaac ggtggacgctggatgtggggcccattccacgggttctgtgtcggagc taacgcgttaagcgtcccgcctggggagtacggccgcaaggctaaaa ctcaaagaaattgacggggconcgcacaagcggcggagcatgcggat taattcgatgnaacgcgaagaaccttacctgggcttgacatgtgcct gacgactgcagagatgtgnttcconttcggggcaggttcacaggtgg tgcatggtcgtcgtcagctcgtgtcgtgagatgttgggttaagtccc gcaacgagcgcaaccctcgccctgtgttgccagcgggttatgccggg aactcacggggaccgccggggttacocnggaggaaggtgggngatga cgtcagatcatcatgccccttacgtccagggcttcacgcatgctaca |

TABLE 33-continued

Bacterial Reference Sequences

| SEQ ID NO: | Description | Sequence |
|---|---|---|
| | | atggccagtacaacgggttgcttcatggtgacatggtgctaatccct taaaactngtctcagttcggatcgtagtctgcaactcgactacgtga aggcggagtcgctagtaatcgcgaatcagcaacgtcgcggtgaatgc gttcccgggccttgtacacaccgcccgtcaagtcatgaaagtgggca gcacccgaagccggtggcctaaccctttgggatggagccgtctaag gtgaggctcgtgattggg |

TABLE 34

Oligomers Screened for the Bacterial Vaginosis Assay

| SEQ ID NO: | Sequence | Type |
|---|---|---|
| 6 | GUCUCUCAACUCGGCUAUGUUUAAAAAAAAAAAAAAAAAAAAAAAAAAAAA | TCO |
| 7 | CGAGCGGAACTAACAG | NT7 |
| 8 | CTTCGGAATGGACATAGA | NT7 |
| 9 | TGCACCAGATGAAACTAG | NT7 |
| 10 | AATTTAATACGACTCACTATAGGGAGATAAGCCGTTACCTTACCA | T7 |
| 11 | GUCUGGGAUACCACUUGCAGAC | Torch |
| 12 | CAGGUGGACUGGGAUAACACCUG | Torch |
| 13 | UCUCUCAAGCCGGCUACCCGUUUAAAAAAAAAAAAAAAAAAAAAAAAAAAA | TCO |
| 14 | GCTGGATGCTCCAACTTG | NT7 |
| 15 | TGTTTAGTAATTTAATACGACTCACTATAGGGAGATCCCATGCCACTAAACA | T7 |
| 16 | CGCAUGUCUUGUUGGGAAUGCG | Torch |
| 17 | GTCTGTTAGGTCAGGAGTT | NT7 |
| 18 | AATTTAATACGACTCACTATAGGGAGACCATCTTCCCCTACCAGA | T7 |
| 19 | CUGCCCUCCUGAUACCGGCAG | Torch |
| 20 | CGUUCACUAUUGGUCUCUGCAUUCUUUAAAAAAAAAAAAAAAAAAAAAAAAAAAAA | TCO |
| 21 | GATTATATAGGACGACAAG | NT7 |
| 22 | aatttaatacgactcactatagggagaGATGATTGACTTGTGATTCCGC | T7 |
| 23 | GCAUGGUGCGAAUUGGGACAUGC | Torch |
| 24 | AATTTAATACGACTCACTATAGGGAGATATCAGGAGCGGATAGGGGTTGAG | T7 |
| 25 | GGACUACCAGGGUAUCUAAUCCUGUUUAAAAAAAAAAAAAAAAAAAAAAAAAAAA | TCO |
| 26 | GTAGGGGCAAGCGTTATCCGGATTC | NT7 |
| 27 | AGGUCAGGAGUUAAAUCUGGGUCCU | Torch |
| 28 | GTAGGTGGCAAGCGTTATCCGGATTC | NT7 |
| 29 | GGCAGGUUGGUCACGCAUUACUCUUUAAAAAAAAAAAAAAAAAAAAAAAAAAAA | TCO |
| 30 | AGGUCAGGAGUUAAAUCUGGGACCU | Torch |
| 31 | AATTTAATACGACTCACTATAGGGAGATAAGCCGTTACCTTACCA | T7 |

TABLE 34-continued

Oligomers Screened for the Bacterial Vaginosis Assay

| SEQ ID NO: | Sequence | Type |
|---|---|---|
| 32 | AATTTAATACGACTCACTATAGGGAGACACCACCTGTGAACCTGC | T7 |
| 33 | CTTACCTGGGCTTGACATGTGCCTG | NT7 |
| 34 | CCUGCAGAGAUGUGGUUUCGCAGG | Torch |
| 35 | AATTTAATACGACTCACTATAGGGAGATCCCATGCCACTAAACAC | T7 |
| 36 | GTAATGCTGGATGCTCCAAC | NT7 |
| 37 | GACGCAUGUCUUGUUGGGCGUC | Torch |
| 38 | CAAGAGCUAUUCUGGAGCAUGGUUUAAAAAAAAAAAAAAAAAAAAAAAAAAA | TCO |
| 39 | GAAACGGGTGGTAATGCTG | NT7 |
| 40 | AAATTTAATACGACTCACTATAGGGAGACCATCCCATGCCACTAAAC | T7 |
| 41 | CCAACUUGACGCAUGUCUUGUUGG | Torch |
| 42 | CTGGATGCTCCAACTTGACG | NT7 |
| 43 | AATTTAATACGACTCACTATAGGGAGATCGAAGCCTAGGTGGGCCAT | T7 |
| 44 | CGGGAAAGUGUUUAGUGGCAUCCCG | Torch |
| 45 | TCCGGATTCATTGGGCGTAA | NT7 |
| 46 | TATCCGGATTCATTGGGCGTAAAG | NT7 |
| 47 | CGGATTCATTGGGCGTAAAGCG | NT7 |
| 48 | GGUCUGUUAGGUCAGAGACC | Torch |
| 49 | CCUGUUAGGUCAGGAGUACAGG | Torch |
| 50 | AATTTAATACGACTCACTATAGGGAGACGGTATCAGGAGCGGATAGG | T7 |
| 51 | AATTTAATACGACTCACTATAGGGAGACTACCAGACTCAAGCCTGCC | T7 |
| 52 | CCGACGACCGUGCAUTTTAAAAAAAAAAAAAAAAAAAAAAAAAAAAA | TCO |
| 53 | GGCUGCUGGCACGUATTTAAAAAAAAAAAAAAAAAAAAAAAAAAA | TCO |
| 54 | CCGGUGUUCUUCCAAAUAUCUGCGCAUUUCTTTAAAAAAAAAAAAAAAAAAAAAAAAAAAA | TCO |
| 55 | TGGTAAGAATTTAATACGACTCACTATAGGGAGATAAGCCGTTACCTTACCA | T7 |
| 56 | CCCACCAACUAGCUAACATTTAAAAAAAAAAAAAAAAAAAAAAAAAAAA | TCO |
| 57 | AATTTAATACGACTCACTATAGGGAGAAGCCTAGGTGGGCCAT | T7 |
| 58 | AATTTAATACGACTCACTATAGGGAGATCAGTCCCAATGTGGCCGTC | T7 |
| 59 | AATTTAATACGACTCACTATAGGGAGAGTCCCAATGTGGCCGTC | T7 |
| 60 | ACGGGTGGTAATGCTG | NT7 |
| 61 | TGCTCCAGAATAGCTCTTG | NT7 |
| 62 | TCCAGAATAGCTCTTG | NT7 |
| 63 | AGGUUGGUCACGCAUUACTTTAAAAAAAAAAAAAAAAAAAAAAAAAAAA | TCO |
| 64 | AATTTAATACGACTCACTATAGGGAGACATGCCACTAAACAC | T7 |
| 65 | GTTTAGAATTTAATACGACTCACTATAGGGAGATCCCATGCCACTAAAC | T7 |
| 66 | GTGTTTAGAATTTAATACGACTCACTATAGGGAGATCCCATGCCACTAAACAC | T7 |
| 67 | CAACUCGGCUAUGCAUCAUTTTAAAAAAAAA | TCO |

TABLE 34-continued

Oligomers Screened for the Bacterial Vaginosis Assay

| SEQ ID NO: | Sequence | Type |
|---|---|---|
| 68 | CUCUCAACUCGGCUAUGCUUUAAAAAAAAAAAAAAAA | TCO |
| 69 | ACCGUCAAAUAAAGGCCAGUUUAAAAAAAAAAAAAA | TCO |
| 70 | AGGUCAGGAGUUAAAUCUGGGACCU | Torch |
| 71 | GGTGAAGAAAGATAGAGG | NT7 |
| 72 | CCGUCCUGGCCUUUAUUUGACGG | Torch |
| 73 | AATTTAATACGACTCACTATAGGGAGAGTGACTTTCTGGTTGAT | T7 |
| 74 | AATTTAATACGACTCACTATAGGGAGACCGTGACTTTCTAAGTAAT | T7 |
| 75 | ACGCUUGCCACCUACGUUUAAAAAAAAAAAAAAAAAAAAAAAAAAAA | TCO |
| 76 | CGGAACTAACAGATTTAC | NT7 |
| 77 | CTTGCACCAGATGAAACT | NT7 |
| 78 | GCTTGCACCAGATGAAACTAG | NT7 |
| 79 | GTGCTTGCACCAGATGAAACT | NT7 |
| 80 | GTGAAGAAAGATAGAG | NT7 |
| 81 | ATGCTGGATGCTCCAACTT | NT7 |
| 82 | CCAGAAGGUCAGGAGUUAAAUCUGG | Torch |
| 83 | GGUCAGGAGUUAAAUCUGGGACC | Torch |
| 84 | ACUCCCUGUUAGGUCAGGAGU | Torch |
| 85 | ACUCCGUUAGGUCAGGAGU | Torch |
| 86 | AGGUCAGGAGUUAAAUCUGGACCU | Torch |
| 87 | GGUCAGGAGUUAAAUCUUGACC | Torch |
| 88 | UCAGGAGUUAAAUCUCCUGA | Torch |
| 89 | ACAAATCACCGTACCCTAGAGGGATATCACTCAGCATAATTTAATGATTTGT | T7 |
| 90 | ACAAATCACCGTACCCTAGAGGGATATCACTCAGCATAATTTAAGTGATTTGT | T7 |
| 91 | AATTTAATACGACTCACTATAGGGAGATACCCGTCGAAGCCTA | T7 |
| 92 | GATGCTCCAACTTGACG | NT7 |
| 93 | TGCTCCAACTTGACG | NT7 |
| 94 | CGTCAGATGCTCCAACTTGACG | NT7 |
| 95 | AATTTAATACGACTCACTATAGGGAGACTGATCATGCGATCTGC | T7 |
| 96 | GACUGGGAUAACACCUGCCAGUC | Torch |
| 97 | AATTTAATACGACTCACTATAGGGAGACCGTGACTTTCTGGT | T7 |
| 98 | AATTTAATACGACTCACTATAGGGAGACGTGACTTTCTAAGTAA | T7 |
| 99 | GATCTGCGTACAGTTCTCAAGAGGGATATCACTCAGCATAATTTAA | T7 |
| 100 | AATTTAATACGACTCACTATAGGGAGACTTCTTTCATGCGAAAGTAGCTT | T7 |
| 101 | AATTTAATACGACTCACTATAGGGAGACTTCTTTCATGCGATAGTAGCTT | T7 |
| 102 | TGTTTAGTGAATTTAATACGACTCACTATAGGGAGATCCCATGCCACTAAACA | T7 |

TABLE 34-continued

Oligomers Screened for the Bacterial Vaginosis Assay

| SEQ ID NO: | Sequence | Type |
|---|---|---|
| 103 | GGCAGAATTTAATACGACTCACTATAGGGAGACTACCAGACTCAAGCCTGCC | T7 |
| 104 | GGCAGGAATTTAATACGACTCACTATAGGGAGACTACCAGACTCAAGCCTGCC | T7 |
| 105 | GGCAGGCAATTTAATACGACTCACTATAGGGAGACTACCAGACTCAAGCCTGCC | T7 |
| 106 | GGCAGGCTAATTTAATACGACTCACTATAGGGAGACTACCAGACTCAAGCCTGCC | T7 |
| 107 | GGCAGGCTTAATTTAATACGACTCACTATAGGGAGACTACCAGACTCAAGCCTGCC | T7 |
| 108 | AATTTAATACGACTCACTATAGGGAGATCCCATGCCACTAAACA | T7 |
| 109 | AATTTAATACGACTCACTATAGGGAGACCATCCCATGCCACTA | T7 |
| 115 | CCAUGUCUUGUUGGGAAAGCAUGG | Torch |
| 116 | CCAGUGUUUAGUGGCAUGGGAUGCACUGG | Torch |
| 117 | GAGCTTGCCTAGATGAATTTG | NT7 |
| 118 | GCTTGCCTAGATGAATTTGGT | NT7 |
| 119 | GAGCTTGCCTAGATGACTTTG | NT7 |
| 120 | GCTTGCCTAGATGACTTTGGT | NT7 |
| 121 | TGCTTGCACCACATGAAACTAG | NT7 |
| 122 | CGAGUAACACGUGGGUAACCUGUACUCG | Torch |
| 123 | CAGGUUGAGUAACACGUGGGUAACCUG | Torch |
| 124 | CUGGAAACAGGUGCUAAUACCGGAUUCCAG | Torch |
| 125 | CUGCAUUAGCUAGUUGGUAAGGUAUGCAG | Torch |
| 126 | CTTCGGAATGGAAATAGA | NT7 |
| 127 | CTTCGGAATGGATATAGA | NT7 |
| 128 | CTTCGGAATGGAGATAGA | NT7 |
| 129 | TGCACCAAATGAAACTAG | NT7 |
| 130 | TGCACCATATGAAACTAG | NT7 |
| 131 | TGCACCATATGAAACTAG | NT7 |
| 132 | TCAGGAGTTAAATCTGG | NT7 |
| 133 | GTTAGGTCAGGAGTTAAATCTGG | NT7 |
| 134 | CGGCCUCGUCCUGCUGAAAGUUUAAAAAAAAAAAAAAAAAAA | TCO |
| 135 | GUACCGUCACCUUGCGGCCUCGUCCCUGUUUAAAAAAAAAAAAAAAAAAAAAAAAAA | TCO |
| 136 | AUCCGCUCCUGAUCGGAU | Torch |
| 137 | UAUCCGCUCCUGAUGGAUA | Torch |
| 138 | AUCCGCUCCUGAUACCCGGAU | Torch |
| 139 | CCCUAUCCGCUCCUUAGGG | Torch |
| 140 | AGGAGCUAUCCGCUCCU | Torch |
| 141 | CGGUACCUAUCCGCUCCUGAUACCG | Torch |

TABLE 34-continued

Oligomers Screened for the Bacterial Vaginosis Assay

| SEQ ID NO: | Sequence | Type |
|---|---|---|
| 142 | CGGUACUAUCCGCUCCUGAUACCG | Torch |
| 143 | CGGUAUAUCCGCUCCUGAUACCG | Torch |
| 144 | CCCUAUCCGCUCCUGAUUAGGG | Torch |
| 145 | GCUCCUGAUACCGGCAGGGAGC | Torch |
| 146 | AATTTAATACGACTCACTATAGGGAGAATCAGGAGCGGATAGGG | T7 |
| 147 | AATCTTGCACAATGGGCGAAA | NT7 |
| 148 | CUUGCGACGAGGCCGCAAG | Torch |
| 149 | GCAGGGACGAGGCCGCCUGC | Torch |
| 150 | CUUGCGGACGAGGCCGCAAG | Torch |
| 151 | UCAGCAGGGACGAGGCCGCUGA | Torch |
| 152 | AATTTAATACGACTCACTATAGGGAGACCGGGGCTTCTTCTGCAGGTAC | T7 |
| 153 | GUCUGGGAUACCACUUGCAGAC | Torch |
| 154 | CGAGUAACUCGUGGGIAACCUGUACUCG | Torch |
| 155 | TGTTTAGAATTTAATACGACTCACTATAGGGAGATCCCATGCCACTAAACA | T7 |
| 156 | TGTTTAGTGGAATTTAATACGACTCACTATAGGGAGATCCCATGCCACTAAACA | T7 |
| 157 | TGTTTAGTGGCAATTTAATACGACTCACTATAGGGAGATCCCATGCCACTAAACA | T7 |
| 158 | CGCAUGUCUUGUUGGGAAUGCG | Torch |
| 159 | CCAUGUCUUGUUGGGAAAGCAUGG | Torch |
| 160 | CAUGUCUUGUUGGGAAAGGACAUG | Torch |
| 161 | ACGCAUGUCUAGAGUUGCGU | Torch |
| 162 | TCTGGAATTTAATACGACTCACTATAGGGAGACCATCTTCCCCTACCAGA | T7 |
| 163 | AATTTAATACGACTCACTATAGGGAGAACATGCGTCTAGTGTTGT | T7 |
| 164 | AATTTAATACGACTCACTATAGGGAGAACAAGCGTCTAGTGTTGT | T7 |
| 165 | CTTTCAGCAGGGACGAGGCC | NT7 |
| 166 | GGTACCTGCAGAAGAAGC | NT7 |
| 167 | ACCTGCAGAAGAAGCCCC | NT7 |
| 168 | GGTACCTGCAGAAGAAGCCCCGG | NT7 |
| 169 | ACCTGCAGAAGAAGCCCCGG | NT7 |
| 170 | AATTTAATACGACTCACTATAGGGAGAGTATCGGCTCAACTCTCTG | T7 |
| 171 | CAGAGAATTTAATACGACTCACTATAGGGAGAGTATCGGCTCAACTCTCTG | T7 |
| 172 | TGCCTAGATGAATTTGGTGC | NT7 |
| 173 | TGCTTGCACCAAATGAAAC | NT7 |
| 174 | TGCCTATAGAAGTTCTTC | NT7 |
| 175 | TTCTTCGGAATGGAAA | NT7 |
| 176 | CGGAACTAACAGATTTACTTCG | NT7 |
| 177 | TACTTCGGTAATGACGT | NT7 |

TABLE 34-continued

Oligomers Screened for the Bacterial Vaginosis Assay

| SEQ ID NO: | Sequence | Type |
|---|---|---|
| 178 | CCAUCAGCGAGCGGCGGAUGG | Torch |
| 179 | CAUCCGCGAGCGGCGGAUG | Torch |
| 180 | GCCGUAGAUACAAGCUAGCGGC | Torch |
| 181 | GCCGUAGGAAAGCGAGCGGC | Torch |
| 182 | CUGCCCAAGAGUCUGGGGCAG | Torch |
| 183 | CUGCCCUUUAGUCUGGGGCAG | Torch |
| 184 | GGUAUCCCCAUAGUCUGGGAUACC | Torch |
| 185 | GUUAUCCCAAGAGACUGGGAUAAC | Torch |
| 186 | ACCUGCCCAAGAGACUGGGAGGU | Torch |
| 187 | CCUGCCCCAUAGUCUGGGCAGG | Torch |
| 188 | ACCUGCCCCAUAGUCUGGGAGGU | Torch |
| 189 | AATTTAATACGACTCACTATAGGGAGACTTGGTAAGCCTTTACCTT | T7 |
| 190 | AATTTAATACGACTCACTATAGGGAGACTTGGTAAGCCGTTACCTT | T7 |
| 191 | AATTTAATACGACTCACTATAGGGAGATAGCGACAGCTTACGC | T7 |
| 192 | AATTTAATACGACTCACTATAGGGAGACAGAACCATCTTTTAAACTCTAG | T7 |
| 193 | AATTTAATACGACTCACTATAGGGAGATCCAAATGGTATCCCAGACT | T7 |
| 194 | AATTTAATACGACTCACTATAGGGAGAGTTTCCAGGTGGTATCCCAGAC | T7 |
| 195 | AATTTAATACGACTCACTATAGGGAGATCCAGGTGTTATCCCAGTC | T7 |
| 196 | AATTTAATACGACTCACTATAGGGAGAGTTTCCAGGTGGTATCCCAGTCT | T7 |
| 197 | AATTTAATACGACTCACTATAGGGAGAGTGATAGCAGAACCATC | T7 |
| 198 | AATTTAATACGACTCACTATAGGGAGAAGTGATAGCAGAACCAT | T7 |
| 199 | AATTTAATACGACTCACTATAGGGAGATTTCATGCGAAAGTAGCTTT | T7 |
| 200 | AATTTAATACGACTCACTATAGGGAGAAAAGTAGCTTTTATCCGGTA | T7 |
| 201 | AATTTAATACGACTCACTATAGGGAGAGCTTACGCCGCCTTTTAAA | T7 |
| 202 | AATTTAATACGACTCACTATAGGGAGAACAGCTTACGCCGCCT | T7 |
| 203 | AATTTAATACGACTCACTATAGGGAGAGCTTACGCCGCCTTTTAAAA | T7 |
| 204 | AATTTAATACGACTCACTATAGGGAGAATCTGCTTTCTTATCC | T7 |
| 205 | AATTTAATACGACTCACTATAGGGAGATTTTAAAAGCTGATCAT | T7 |
| 206 | GGACGAGGCCGCAAGG | NT7 |
| 207 | AGGGACGAGGCCGCAAG | NT7 |
| 208 | TAGGCGGTCTGTTAGGTCA | NT7 |
| 209 | CGTAGGCGGTCTGTTAG | NT7 |
| 210 | CCUAUCCGCUCCUGAUACGAUAGG | Torch |
| 211 | CGGUAUCCUAUCCGCUCCUGAUACCG | Torch |
| 212 | CUGCCGCUCCUGAUACCGGCAG | Torch |
| 213 | AATTTAATACGACTCACTATAGGGAGAAGTCATGGCCCAGAAGACC | T7 |
| 214 | CAGGUGCAAGAGACUGGGAUAACACCUG | Torch |

TABLE 34-continued

Oligomers Screened for the Bacterial Vaginosis Assay

| SEQ ID NO: | Sequence | Type |
|---|---|---|
| 215 | CCAAGAGACUGGGAUAACACUCUUGG | Torch |
| 216 | CAGGUGAGAGACUGGGAUAACACCUG | Torch |
| 217 | CAGAUGCUAAUACCGGAUACAUCUG | Torch |
| 218 | CGGAUAACAACACUAGACGUAUCCG | Torch |
| 219 | CGUCUACGGAUAACAACACUAGACG | Torch |
| 220 | AATTTAATACGACTCACTATAGGGAGAGTAAGCCGTTACCTTAC | T7 |
| 221 | AAGCGGUUUACAACCCGAAGGCCUUTTAAAAAAAAAAAAAAAAAAAAAAAAAAAA | TCO |
| 222 | UCCAUCAGACUUGCGUCCAUUTAAAAAAAAAAAAAAAAAAAAAAAAAAAA | TCO |
| 223 | GGTAGTGAAGAAAGATAGA | NT7 |
| 224 | TCTATCTGGTAGTGAAGAAAGATAGA | NT7 |
| 225 | AGTGAAGAAGGTTTTCGGAT | NT7 |
| 226 | ATCCGAGTGAAGAAGGTTTTCGGAT | NT7 |
| 227 | CCTCTATGGTGAAGAAAGATAGAGG | NT7 |
| 228 | CUUGCGACGAGGCCGCAAG | Torch |
| 229 | AATTTAATACGACTCACTATAGGGAGATCCATCTTCCCCTACCAGACT | T7 |
| 230 | AATTTAATACGACTCACTATAGGGAGATTCCATCTTCCCCTACCAGACTCA | T7 |
| 231 | AATTTAATACGACTCACTATAGGGAGAATTCCATCTTCCCCTACCAGACT | T7 |
| 232 | TGTTAGGTCAGGAGTTAAATCT | NT7 |
| 233 | GCUCCUGAUACCGGCAGGGGAGC | Torch |
| 234 | CUCCUGAUACCGGCAGAGGAG | Torch |
| 235 | GCUCCUGAUACCGGCAGGAGC | Torch |
| 236 | UGCCGCUCCUGAUACCGGCA | Torch |
| 237 | UGCCGGCUCCUGAUACCGGCA | Torch |
| 238 | CGGUAUAUCCGCUCCUGAUACCG | Torch |
| 239 | GGUAUUAUCCGCUCCUGAUACCG | Torch |
| 240 | GGUAUUAUCCGCUCCUGAUACC | Torch |
| 241 | CUGCCUCCUGAUACCGGCAG | Torch |
| 242 | CGGUACUAUCCGCUCCUGAUACCG | Torch |
| 243 | AUCCGCUCCUGAUACCCGGAU | Torch |
| 244 | TCTGGAAATTTAATACGACTCACTATAGGGAGAACCATCTTCCCCTATCCAGA | T7 |
| 245 | TCTGGATAATTTAATACGACTCACTATAGGGAGAACCATCTTCCCCTATCCAGA | T7 |
| 246 | TCTGGATAAATTTAATACGACTCACTATAGGGAGAACCATCTTCCCCTATCCAGA | T7 |
| 247 | TCTGGATAGAATTTAATACGACTCACTATAGGGAGAACCATCTTCCCCTATCAGA | T7 |
| 248 | TCTGGTAATTTAATACGACTCACTATAGGGAGACCATCTTCCCCTACCAGA | T7 |

TABLE 34-continued

Oligomers Screened for the Bacterial Vaginosis Assay

| SEQ ID NO: | Sequence | Type |
|---|---|---|
| 249 | TCTGGTAAATTTAATACGACTCACTATAGGGAGACCATCTTCCCCTACCAGA | T7 |
| 250 | TCTGGTAGAATTTAATACGACTCACTATAGGGAGACCATCTTCCCCTACCAGA | T7 |
| 251 | TCTGGTAGGAATTTAATACGACTCACTATAGGGAGACCATCTTCCCCTACCAGA | T7 |
| 252 | AATTTAATACGACTCACTATAGGGAGAGGTATCAGGAGCGGATAG | T7 |
| 253 | AATTTAATACGACTCACTATAGGGAGAGGTATCAGGAGCGGATA | T7 |
| 254 | GAUCCGCUCCUGAUACCCGGAUC | Torch |
| 255 | GCGGUACUAUCCGCUCCUGAUACCGC | Torch |
| 256 | CUCCUGAUACCGGCAGAGGAG | Torch |
| 257 | UCUGUUAGUUCCTTTAAAAAAAAAAAAAAAAAAAAAAAAAAAA | TCO |
| 258 | CGGATGGGTGAGTAAC | NT7 |
| 259 | CACUCACGCAUGUCUAGAGUG | Torch |
| 260 | CAUGCUCCGCCGCUUGUTTTAAAAAAAAAAAAAAAAAAAAAAAAAAAA | TCO |
| 261 | CCUGCAGAGAUGUGGUUUCGCAGG | Torch |

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes. To the extent that any material incorporated by reference is inconsistent with the express content of this disclosure, the express content controls.

The instant application contains a Sequence Listing which has been submitted electronically in ASCII format and is hereby incorporated by reference in its entirety. Said ASCII copy, created on Aug. 20, 2019, is named 2019 Aug. 20_01159-0039-60PCT_Seq List_ST25.txt and is 66.8 kilobytes in size.

What is claimed is:

1. A method for determining the presence or absence of Bacterial Vaginosis (BV) in a subject, the method comprising:
   (a) providing a sample from a subject suspected of having BV;
   (b) performing a nucleic-acid-based detection assay for the detection of Lactobacillus sp., A. vaginae, and G. vaginalis in the sample, wherein the detection assay is an amplification-based assay comprising an in vitro nucleic acid amplification reaction, and wherein performing the detection assay comprises contacting the sample with
      (i) first, second, third, and fourth Lactobacillus-specific amplification oligomers for amplifying a target region of a Lactobacillus sp. target nucleic acid, wherein each of the first, second, third, and fourth Lactobacillus-specific amplification oligomers comprises a target-hybridizing sequence for hybridizing to the target region of the Lactobacillus sp. target nucleic acid, wherein
         the first Lactobacillus-specific amplification oligomer comprises a first target-hybridizing sequence consisting of the nucleotide sequence of residues 28-45 of SEQ ID NO: 10, wherein the first Lactobacillus-specific amplification oligomers is a promoter primer or a promoter provider further comprising a promoter sequence located 5' to the target-hybridizing sequence;
         the second Lactobacillus-specific amplification oligomer comprises a second target-hybridizing sequence consisting of the nucleotide sequence of SEQ ID NO:7;
         the third Lactobacillus-specific amplification oligomer comprises a third target-hybridizing sequence consisting of the nucleotide sequence of SEQ ID NO:8; and
         the fourth Lactobacillus-specific amplification oligomer comprises a fourth target-hybridizing sequence consisting of the nucleotide sequence of SEQ ID NO:9;
      (ii) first and a second A. vaginae-specific amplification oligomers for amplifying a target region of a A. vaginae target nucleic acid, wherein each of the first and second A. vaginae-specific amplification oligomers comprises a target-hybridizing sequence for hybridizing to the target region of the A. vaginae target nucleic acid; and
      (iii) first and a second G. vaginalis-specific amplification oligomers for amplifying a target region of a G. vaginalis target nucleic acid, wherein each of the first and second G. vaginalis-specific amplification oligomers comprises a target-hybridizing sequence for hybridizing to the target region of the G. vaginalis target nucleic acid;
   (c) for each of Lactobacillus sp., A. vaginae, and G. vaginalis, assigning a quantitative value based on the detection assay;
   (d) subtracting the Lactobacillus sp. quantitative value from the greater of the A. vaginae quantitative value and the G. vaginalis quantitative value, wherein step (d) further comprises adding an internal control (IC) adjustment factor that compensates for sample inhibition of the detection assay, wherein the IC adjustment factor is based on a ratio of (i) an observed internal control (IC) value generated from the detection assay to (ii) an expected IC value for the detection assay;
   (e) assigning a single BV score based on step (d); and
   (f) determining the presence or absence of BV in the subject based on a comparison of the BV score to a cutoff value.

2. The method of claim 1, wherein the in vitro nucleic acid amplification reaction is an isothermal amplification reaction.

3. The method of claim 2, wherein the isothermal amplification reaction is a transcription-mediated amplification (TMA) reaction.

4. The method of claim 2, wherein the isothermal amplification reaction is a real-time amplification reaction.

5. The method of claim 1, wherein (i) the first A. vaginae-specific amplification oligomer comprises a first A. vaginae-specific target-hybridizing sequence consisting of the nucleotide sequence of residues 28-45 of SEQ ID NO:18 and (ii) the second A. vaginae-specific amplification oligomer comprises a second A. vaginae-specific target-hybridizing sequence consisting of the nucleotide sequence of SEQ ID NO:17.

6. The method of claim 5, wherein the first A. vaginae-specific amplification oligomer is a promoter primer or a promoter provider further comprising a promoter sequence located 5' to the target hybridizing sequence.

7. The method of claim 1, wherein (i) the first G. vaginalis-specific amplification oligomer comprises a first G. vaginalis-specific target-hybridizing sequence consisting of the nucleotide sequence of residues 36-52 of SEQ ID NO:15 and (ii) the second G. vaginalis-specific amplification oligomer comprises a second G. vaginalis-specific target-hybridizing sequence consisting of the nucleotide sequence of SEQ ID NO:14.

8. The method of claim 7, wherein the first G. vaginalis-specific amplification oligomer is a promoter primer or a promoter provider further comprising a promoter sequence located 5' to the target hybridizing sequence.

9. The method of claim 1, wherein the promoter sequence is a T7 promoter sequence.

10. The method of claim 9, wherein the T7 promoter sequence has a nucleotide sequence of residues 1-27 of SEQ ID NO:10.

11. The method of claim 1, wherein the BV score is assigned using the equation $$BV\ score = C_0 + W_L \text{Max}(L_S, F_{LS}) + W_{GA}\text{Max}(As, Gs, F_{GAS}) + W_{IC} \text{Log } 2(\text{ICRatio}),$$

wherein $C_0$ is an adjustment constant;

$W_L$ is a weighting constant for *Lactobacillus* sp.; Max $(L_S, F_{LS})$ is the greater of $L_S$ and $F_{LS}$, wherein $L_S$ is an observed standardized quantitative value for *Lactobacillus* sp. and $F_{LS}$ is an imposed minimum standardized quantitative value for *Lactobacillus* sp.;

$W_{GA}$ is a weighting constant for *A. vaginae* and *G. vaginalis*;

Max (As, Gs, $F_{GAS}$) is the greater of As, Gs, and $F_{GAS}$, wherein As is an observed standardized quantitative value for *A. vaginae*, Gs is an observed standardized quantitative value for *G. vaginalis*, and $F_{GAS}$ is an imposed minimum standardized quantitative value for *A. vaginae* and *G. vaginalis*;

$W_{IC}$ is an internal control (IC) weighting constant; and

ICRatio is the ratio of (i) the observed internal control (IC) value generated from the detection assay to (ii) the expected IC value for the detection assay.

* * * * *

UNITED STATES PATENT AND TRADEMARK OFFICE
CERTIFICATE OF CORRECTION

PATENT NO. : 12,291,753 B2
APPLICATION NO. : 17/182861
DATED : May 6, 2025
INVENTOR(S) : Getman et al.

It is certified that error appears in the above-identified patent and that said Letters Patent is hereby corrected as shown below:

On the Title Page

Item (56), under "OTHER PUBLICATIONS", in Column 2, Line 1, replace "possible ?."" with -- possible?. " --.

Item (56), under "OTHER PUBLICATIONS", in Column 2, Line 28, replace "Gerdnerella" with -- Gardnerella --.

Item (57), under "ABSTRACT", in Column 2, Line 4, replace "Gardneralla" with -- Gardnerella --.

Item (57), under "ABSTRACT", in Column 2, Line 6, replace "Gardneralla" with -- Gardnerella --.

In the Specification

Column 1, Lines 20-21, replace "20 01159-0039-OOPCT_Seq_List_ST25.txt" with -- 20_01159-0039-00PCT_Seq_List_ST25.txt --.

Column 1, Line 34, replace "partners. See" with -- partners. (See --.

Column 1, Line 53, replace "later" with -- latter --.

Column 2, Line 32, replace "BV:" with -- BV; --.

Column 2, Line 33, replace "vaginae." with -- vaginae, --.

Column 2, Line 34, replace "sample:" with -- sample; --.

Signed and Sealed this
Twenty-seventh Day of January, 2026

John A. Squires
*Director of the United States Patent and Trademark Office*

Column 2, Line 35, replace "vaginae." with -- vaginae, --.

Column 2, Line 36, replace "assay:" with -- assay; --.

Column 2, Line 39, replace "value:" with -- value; --.

Column 2, Line 45, replace "vaginae." with -- vaginae, --.

Column 2, Line 48, replace "vaginae." with -- vaginae, --.

Column 2, Lines 60-61, replace "BV score=$C_0+W_L$Max ($L_S$, $F_{LS}$)+$W_{GA}$Max (As, Gs, $F_{GAS}$)+$W_{IC}$ Log 2 (ICRatio)," with -- BV score=$C_0+W_L$Max($L_S$, $F_{LS}$)+$W_{GA}$Max($A_S$, $G_S$, $F_{GAS}$)+$W_{IC}$Log2(ICRatio), --.

Column 2, Line 62, replace "constant: WL" with -- constant; $W_L$ --.

Column 2, Lines 62-63, replace "sp.: Max ($L_S$, $F_{LS}$)" with -- sp.; Max($L_S$, $F_{LS}$) --.

Column 2, Line 66, replace "sp.:" with -- sp.; --.

Column 2, Line 67, replace "vaginalis: Max (As, Gs," with -- vaginalis; Max($A_S$, $G_S$, --.

Column 3, Line 1, replace "As, Gs," with -- $A_S$, $G_S$, --.

Column 3, Line 1, replace "As is" with -- $A_S$ is --.

Column 3, Line 2, replace "Gs" with -- $G_S$ --.

Column 3, Line 5, replace "(e.g., 0):" with -- (e.g., 0); --.

Column 3, Line 19, replace "IRNA" with -- rRNA --.

Column 3, Line 23, replace "265:" with -- 265; --.

Column 3, Line 26, replace "247:" with -- 247; --.

Column 3, Line 28, replace "298:" with -- 298; --.

Column 3, Line 47, replace "NO: 10:" with -- NO: 10; --.

Column 3, Line 51, replace "NO:7:" with -- NO:7; --.

Column 3, Line 59, replace "NO:9:" with -- NO:9; --.

Column 4, Line 15, replace "14:" with -- 14; --.

Column 4, Line 17, replace "vaginae." with -- vaginae, --.

Column 4, Line 21, replace "vaginae." with -- vaginae, --.

Column 4, Line 35, replace "target-hy bridizing" with -- target-hybridizing --.

Column 4, Line 37, replace "18:" with -- 18; --.

Column 4, Line 39, replace "17:" with -- 17; --.

Column 4, Line 46, replace "10:" with -- 10; --.

Column 4, Line 48, replace "NO:7:" with -- NO:7; --.

Column 4, Line 54, replace "18:" with -- 18; --.

Column 4, Line 56, replace "17:" with -- 17; --.

Column 5, Line 9, replace "NO:10:" with -- NO:10; --.

Column 5, Line 35, replace "probe:" with -- probe; --.

Column 5, Line 38, replace "L . . . gasseri" with -- L. gasseri --.

Column 6, Line 2, replace "16:" with -- 16; --.

Column 6, Line 15, replace "acid:" with -- acid; --.

Column 6, Line 21, replace "12:" with -- 12; --.

Column 6, Line 23, replace "target-hy bridizing" with -- target-hybridizing --.

Column 7, Line 15, replace "vaginae." with -- vaginae, --.

Column 7, Line 18, replace "vaginae." with -- vaginae, --.

Column 7, Line 65, replace "vaginae." with -- vaginae, --.

Column 8, Line 2, replace "vaginae." with -- vaginae, --.

Column 8, Line 6, replace "vaginae." with -- vaginae, --.

Column 8, Line 13, replace "NO:7:" with -- NO:7; --.

Column 8, Line 13, replace "target-hy bridizing" with -- target-hybridizing --.

Column 8, Line 15, replace "NO:8:" with -- NO:8; --.

Column 8, Line 19, replace "18:" with -- 18; --.

Column 8, Line 21, replace "17:" with -- 17; --.

Column 8, Line 28, replace "10:" with -- 10; --.

Column 8, Line 30, replace "NO:7:" with -- NO:7; --.

Column 8, Line 32, replace "NO:8:" with -- NO:8; --.

Column 8, Line 36, replace "NO: 18:" with -- NO:18; --.

Column 8, Line 38, replace "NO: 17:" with -- NO:17; --.

Column 8, Line 57, replace "10:" with -- 10; --.

Column 9, Line 15, replace "probe:" with -- probe; --.

Column 9, Lines 35-36, replace "hy bridizes" with -- hybridizes --.

Column 9, Line 47, replace "16:" with -- 16; --.

Column 9, Line 61, replace "acid:" with -- acid; --.

Column 9, Line 67, replace "12:" with -- 12; --.

Column 10, Line 48, replace "vaginae." with -- vaginae, --.

Column 10, Line 62, replace "NO:7:" with -- NO:7; --.

Column 11, Line 2, replace "NO:9:" with -- NO:9; --.

Column 11, Line 30, replace "NO:7:" with -- NO:7; --.

CERTIFICATE OF CORRECTION (continued)
U.S. Pat. No. 12,291,753 B2

Column 11, Line 32, replace "NO:8:" with -- NO:8; --.

Column 11, Line 36, replace "18:" with -- 18; --.

Column 11, Line 38, replace "NO:17:" with -- NO:17; --.

Column 11, Line 45, replace "10:" with -- 10; --.

Column 11, Line 47, replace "NO:7:" with -- NO:7; --.

Column 11, Line 48, replace "target-hy bridizing" with -- target-hybridizing --.

Column 11, Line 49, replace "NO:8:" with -- NO:8; --.

Column 11, Line 53, replace "NO: 18:" with -- NO:18; --.

Column 11, Line 55, replace "17:" with -- 17; --.

Column 12, Line 7, replace "10:" with -- 10; --.

Column 12, Line 28, replace "probe:" with -- probe; --.

Column 12, Line 57, replace "16:" with -- 16; --.

Column 13, Line 3, replace "acid:" with -- acid; --.

Column 13, Line 9, replace "12:" with -- 12; --.

Column 13, Line 25, replace "quencher:" with -- quencher; --.

Column 13, Line 58, replace "NO:7:" with -- NO:7; --.

Column 13, Line 64, replace "NO:9:" with -- NO:9; --.

Column 14, Line 10, replace "target-hy bridizing" with -- target-hybridizing --.

Column 14, Line 11, replace "NO:7:" with -- NO:7; --.

Column 14, Line 17, replace "10:" with -- 10; --.

Column 14, Line 19, replace "target-hy bridizing" with -- target-hybridizing --.

Column 14, Line 46, replace "acid:" with -- acid; --.

Column 14, Line 49, replace "NO:6:" with -- NO:6; --.

Column 14, Line 56, replace "hy bridizes" with -- hybridizes --.

Column 14, Line 65, replace "acid:" with -- acid; --.

Column 15, Line 4, replace "12:" with -- 12; --.

Column 17, Line 2, replace "NO:14:" with -- NO:14; --.

Column 17, Line 29, replace "15:" with -- 15; --.

Column 18, Line 24, replace "vaginae." with -- vaginae, --.

Column 18, Line 27, replace "vaginae." with -- vaginae, --.

Column 18, Line 40, replace "NO:7:" with -- NO:7; --.

Column 18, Line 47, replace "NO:9:" with -- NO:9; --.

Column 19, Line 2, replace "NO:14:" with -- NO:14; --.

Column 19, Line 4, replace "vaginae." with -- vaginae, --.

Column 19, Line 8, replace "vaginae." with -- vaginae, --.

Column 19, Line 12, replace "vaginae." with -- vaginae, --.

Column 19, Line 20, replace "NO:7:" with -- NO:7; --.

Column 19, Line 46, replace "NO:7:" with -- NO:7; --.

Column 19, Line 49, replace "NO:8:" with -- NO:8; --.

Column 19, Line 52, replace "NO:9:" with -- NO:9; --.

Column 22, Line 40, replace "vaginae." with -- vaginae, --.

Column 22, Line 53, replace "NO:7:" with -- NO:7; --.

Column 22, Line 60, replace "NO:9:" with -- NO:9; --.

Column 23, Line 21, replace "NO:10:" with -- NO:10; --.

Column 23, Line 24, replace "NO:7:" with -- NO:7; --.

Column 23, Line 27, replace "NO:8:" with -- NO:8; --.

Column 23, Line 30, replace "NO:9:" with -- NO:9; --.

Column 23, Line 33, replace "NO: 18:" with -- NO:18; --.

Column 23, Line 58, replace "NO:18:" with -- NO:18; --.

Column 26, Line 35, replace "BV:" with -- BV; --.

Column 26, Line 37, replace "vaginae." with -- vaginae, --.

Column 26, Line 37, replace "sample:" with -- sample; --.

Column 26, Line 38, replace "vaginae." with -- vaginae, --.

Column 26, Line 40, replace "assay:" with -- assay; --.

Column 26, Line 43, replace "value:" with -- value; --.

Column 26, Line 56, replace "vaginae." with -- vaginae, --.

Column 26, Line 59, replace "vaginae." with -- vaginae, --.

Column 27, Lines 11-12, replace
"BV score=$C_0+W_L Max(L_S,F_{LS})+W_{GA}Max(A_S,G_S,F_{GAS})+W_{IC} Log\ 2(ICRatio)$," with
-- BV score=$C_0+W_L Max(L_S,F_{LS})+W_{GA}Max(A_S,G_S,F_{GAS})+W_{IC}Log2(ICRatio)$, --.

Column 27, Line 15, replace "constant:" with -- constant; --.

Column 27, Line 16, replace "WL" with -- $W_L$ --.

Column 27, Line 16, replace "sp.:" with -- sp.; --.

Column 27, Line 17, replace "Max ($L_S$, $F_{LS}$)" with -- Max($L_S$, $F_{LS}$) --.

Column 27, Line 20, replace "sp.:" with -- sp.; --.

Column 27, Line 23, replace "Max ($A_S$, $G_S$," with -- Max($A_S$, $G_S$, --.

Column 27, Line 23, replace "$A_S$, $G_S$," with -- $A_S$, $G_S$, --.

Column 27, Line 24, replace "As" with -- $A_S$ --.

Column 27, Line 25, replace "Gs" with -- $G_S$ --.

Column 27, Line 28, replace "vaginalis:" with -- vaginalis; --.

Column 27, Line 37, replace "vaginae." with -- vaginae, --.

Column 27, Line 41, replace "vaginae." with -- vaginae, --.

Column 27, Line 49, replace "247:" with -- 247; --.

Column 28, Line 19, replace "NO:7:" with -- NO:7; --.

Column 28, Line 26, replace "NO:9:" with -- NO:9; --.

Column 28, Line 50, replace "vaginae." with -- vaginae, --.

Column 28, Line 54, replace "vaginae." with -- vaginae, --.

Column 28, Line 61, replace "NO:10:" with -- NO:10; --.

Column 29, Line 6, replace "18:" with -- 18; --.

Column 29, Line 19, replace "10:" with -- 10; --.

Column 29, Line 25, replace "NO:8:" with -- NO:8; --.

Column 29, Line 31, replace "18:" with -- 18; --.

Column 32, Line 56, replace "NO:7:" with -- NO:7; --.

Column 33, Line 10, replace "NO: 7:" with -- NO:7; --.

Column 33, Line 21, replace "NO: 7:" with -- NO:7; --.

Column 34, Line 45, replace "label" with -- label. --.

Column 36, Line 54, replace "14:" with -- 14; --.

Column 38, Line 43, replace "endpoints":" with -- endpoints"; --.

Column 38, Line 46, replace "4x," with -- 4π, --.

Column 38, Line 51, replace "vaginae." with -- vaginae, --.

Column 38, Lines 55-56, replace "vaginae." with -- vaginae, --.

Column 39, Line 23, replace "isoguanine:" with -- isoguanine; --.

Column 39, Line 26, replace "N+-methyl" with -- $N^4$-methyl --.

Column 39, Line 31, replace "06-methylguanine," with -- $O^6$-methylguanine, --.

Column 39, Line 33, replace "0+-alkyl-pyrimidines," with -- $O^4$-alkyl-pyrimidines, --.

Column 39, Lines 34-35, replace "pyrazolo[3,4-d]pyrimidine:" with -- pyrazolo[3,4-d]pyrimidine; --.

Column 41, Line 26, replace "vaginae." with -- vaginae, --.

Column 41, Line 31, replace "vaginae." with -- vaginae, --.

Column 41, Line 35, replace "vaginae." with -- vaginae, --.

Column 41, Line 54, replace "vaginae." with -- vaginae, --.

Column 41, Line 57, replace "vaginae." with -- vaginae, --.

Column 41, Line 60, replace "vaginae." with -- vaginae, --.

Column 41, Line 62, replace "vaginae." with -- vaginae, --.

Column 42, Line 7, replace "vaginae." with -- vaginae, --.

Column 42, Line 10, replace "vaginae." with -- vaginae, --.

Column 42, Line 18, replace "refer" with -- to refer --.

Column 42, Line 41, replace "reagent:" with -- reagent; --.

Column 42, Line 46, replace "polymerase:" with -- polymerase; --.

Column 43, Line 58, replace "forming" with -- of forming --.

Column 44, Line 50, replace "5,422,252:" with -- 5,422,252; --.

Column 45, Line 43, replace ""TaqManR" with -- "TaqMan® --.

Column 45, Line 43, replace "detection" with -- detection of --.

Column 46, Line 35, replace "oligonucleotide."" with -- oligonucleotide," --.

Column 46, Line 51, replace "(see." with -- (see, --.

Column 46, Line 54, replace "Aio" with -- $A_{10}$ --.

Column 46, Line 55, replace "A40)," with -- $A_{40}$), --.

Column 46, Line 55, replace "T3A14 to T3A30)," with -- $T_3A_{14}$ to $T_3A_{30}$), --.

Column 46, Line 59, replace "To4A1040" with -- $T_{0-4}A_{10-40}$ --.

Column 47, Line 10, replace "size+" with -- size ± --.

Column 48, Line 10, replace "quatitative" with -- quantitative --.

Column 48, Line 17, replace "Quatitative" with -- Quantitative --.

Column 48, Line 24, replace "that" with -- than --.

Column 48, Lines 52-53, replace "BV score=$C_0$+$W_L$Max ($L_S$, $F_{LS}$)+$W_{GA}$Max (As, Gs, $F_{GAS}$)+$W_{IC}$ Log 2 (ICRatio)," with -- BV score=$C_0$+$W_L$Max($L_S$, $F_{LS}$)+$W_{GA}$Max($A_S$, $G_S$, $F_{GAS}$)+$W_{IC}$Log2(ICRatio), --.

Column 49, Line 14, replace "(FGA)" with -- ($F_{GA}$) --.

Column 49, Line 28, replace "sp.:" with -- sp.; --.

Column 49, Line 29, replace "vaginalis: Candida sp.:" with -- vaginalis; Candida sp.; --.

Column 49, Lines 30-31, replace "Clostridiales: Clostridium-like sp.: Eggerthella sp.: Enterobacteria:" with -- Clostridiales; Clostridium-like sp.; Eggerthella sp.; Enterobacteria; --.

Column 49, Line 31, replace "micros:" with -- micros; --.

Column 49, Lines 31-32, replace "christensenii:" with -- christensenii; --.

Column 49, Line 32, replace "amnionii: Peptoniphilus sp.:" with -- amnionii; Peptoniphilus sp.; --.

Column 49, Line 33, replace "sp.: Mycoplasma hominis: Sneathia sanguinegens:" with -- sp.; Mycoplasma hominis; Sneathia sanguinegens; --.

Column 49, Line 34, replace "tetradius: Mobiluncus sp.: Mobiluncus hominis:" with -- tetradius; Mobiluncus sp.; Mobiluncus hominis; --.

Column 49, Line 35, replace "sp.: Prevotella sp.:" with -- sp.; Prevotella sp.; --.

Column 49, Line 38, replace "one of" with -- one or --.

Column 49, Line 47, replace "265:" with -- 265; --.

Column 49, Line 48, replace "IRNA" with -- rRNA --.

Column 49, Line 50, replace "247:" with -- 247; --.

Column 49, Line 52, replace "298:" with -- 298; --.

Column 49, Line 53, replace "IRNA" with -- rRNA --.

Column 50, Line 13, replace "12:" with -- 12; --.

Column 50, Line 31, replace "12:" with -- 12; --.

Column 51, Line 7, replace "(see." with -- (see, --.

Column 51, Line 19, replace "3‴" with -- 3' --.

Column 51, Line 61, replace "configure" with -- configured --.

Column 52, Line 43, replace "NO:7." with -- NO:7, --.

Column 52, Line 44, replace "NO:9:" with -- NO:9; --.

Column 52, Line 62, replace "NO:7." with -- NO:7, --.

Column 53, Line 19, replace "NO: 7." with -- NO:7, --.

Column 53, Line 36, replace "540)" with -- 540 --.

Column 53, Line 55, replace "18):" with -- 18); --.

CERTIFICATE OF CORRECTION (continued)

U.S. Pat. No. 12,291,753 B2

Column 53, Line 65, replace "IRNA." with -- rRNA. --.

Column 54, Line 20, replace "15):" with -- 15); --.

Column 54, Line 44, replace "5,849,481:" with -- 5,849,481; --.

Column 54, Lines 45-46, replace "associate" with -- associated --.

Column 55, Line 11, replace "(see." with -- (see, --.

Column 55, Line 30, replace "(see." with -- (see, --.

Column 55, Line 33, replace "20060194240A1:" with -- 20060194240A1; --.

Column 55, Line 50, replace "298:" with -- 298; --.

Column 55, Line 64, replace "acid:" with -- acid; --.

Column 56, Line 20, replace "NO:11:" with -- NO:11; --.

Column 56, Line 22, replace "12:" with -- 12; --.

Column 56, Line 40, replace "Enzymology. Vol. 152." with -- Enzymology, Vol. 152, --.

Column 56, Lines 57-58, replace "|target nucleic acid|:" with -- [target nucleic acid]: --.

Column 56, Line 62, replace "See." with -- See, --.

Column 56, Line 64, replace "2002: Wang," with -- 2002; Wang, --.

Column 56, Line 64, replace "2002:" with -- 2002; --.

Column 57, Line 16, replace "298:" with -- 298; --.

Column 57, Line 30, replace "a probe" with -- probe --.

Column 57, Line 32, replace "IRNA" with -- rRNA --.

Column 57, Line 34, replace "acid:" with -- acid; --.

Column 57, Line 58, replace "11:" with -- 11; --.

Column 57, Line 61, replace "12:" with -- 12; --.

Column 58, Line 13, replace "(see." with -- (see, --.

Column 58, Line 30, replace "2001:" with -- 2001; --.

Column 58, Line 31, replace "1998:" with -- 1998; --.

Column 58, Line 50, replace "CLEAVASER" with -- CLEAVASE® --.

Column 59, Line 12, replace "may include may include" with -- may include --.

Column 59, Line 65, replace "(see." with -- (see, --.

Column 59, Line 66, replace "6,534,273:" with -- 6,534,273; --.

Column 60, Line 16, replace "Aio to A+0)," with -- $A_{10}$ to $A_{40}$), --.

Column 60, Lines 17-18, replace "A14 to A30 or T3A14 to T3A30)," with -- $A_{14}$ to $A_{30}$ or $T_3A_{14}$ to $T_3A_{30}$), --.

Column 61, Line 43, replace "cocci: Eggerthella sp.:" with -- cocci; Eggerthella sp.; --.

Column 61, Line 44, replace "Clostridiales: Clostridium-like sp.:" with -- Clostridiales; Clostridium-like sp.; --.

Column 61, Line 45, replace "Enterobacteria: Peptostreptococcus micros:" with -- Enterobacteria; Peptostreptococcus micros; --.

Column 61, Line 46, replace "christensenii: Leptotrichia amnionii: Peptoniphilus sp.:" with -- christensenii; Leptotrichia amnionii; Peptoniphilus sp.; --.

Column 61, Line 47, replace "sp.: Mycoplasma hominis: Sneathia sanguinegens:" with -- sp.; Mycoplasma hominis; Sneathia sanguinegens; --.

Column 61, Lines 48-49, replace "tetradius: Mobiluncus sp.: Mobiluncus hominis:" with -- tetradius; Mobiluncus sp.; Mobiluncus hominis; --.

Column 61, Line 49, replace "hongkongensis: Prevotella sp.:" with -- hongkongensis; Prevotella sp.; --.

Column 61, Line 50, replace "sp.:" with -- sp.; --.

Column 61, Line 60, replace "nor" with -- not --.

Column 62, Line 7, replace "sequences):" with -- sequences); --.

Column 62, Line 15, replace "sequences):" with -- sequences); --.

Column 62, Line 24, replace "region:" with -- region; --.

Column 62, Line 65, replace "Interpretion" with -- Interpretation --.

Column 62, Line 67, replace "("L.spp":" with -- ("L.spp"; --.

Column 63, Line 2, replace "respectively:" with -- respectively; --.

Column 63, Lines 25-26, replace "Score=$C_0+W_L*Max(L-M_L,F_L-M_L)+W_{AG}*Max(G-M_G,A-M_A,F_{GA}-M_G)+W_{IC}*log\ 2(IC/calIC)$" with -- Score=$C_0+W_L*Max(L-M_L,F_L-M_L)+W_{AG}*Max(G-M_G,A-M_A,F_{GA}-M_G)+W_{IC}*log2(IC/calIC)$ --.

Column 63, Line 30, replace "interterpreting" with -- interpreting --.

Column 63, Line 64, replace "(by" with -- by --.

Column 64, Lines 37-39, replace
"BV Score=$C_0+W_LMax(L_S,F_{LS})+W_AMax(A_S,F_{AS})+W_GMax(G_S,F_{GS})+W_{GA}Max(A_S,G_S,F_{GAS})+W_{IC}\ Log\ 2(ICRatio)$" with
-- BV Score=$C_0+W_LMax(L_S,F_{LS})+W_AMax(A_S,F_{AS})+W_GMax(G_S,F_{GS})+W_{GA}Max(A_S,G_S,F_{GAS})+W_{IC}Log2(ICRatio)$ --.

Column 64, Lines 45-46, replace
"BV Score=$C_0+W_LMax(L_S,F_{LS})+W_{GA}Max(A_S,G_S,F_{GAS})+W_{IC}\ Log\ 2(ICRatio)$" with
-- BV Score=$C_0+W_LMax(L_S,F_{LS})+W_{GA}Max(A_S,G_S,F_{GAS})+W_{IC}Log2(ICRatio)$ --.

Column 64, Line 57, replace "$FL_S$)" with -- $F_{LS}$) --.

Column 65, Line 51, replace "data" with -- of data --.

Column 68, Line 34, replace "gasseri. L. jensenii." with -- gasseri, L. jensenii, --.

Column 68, Line 42, replace "gonorrhoeae" with -- gonorrhea --.

Column 68, Line 43, replace "Iwoffii" with -- lwoffii --.

Column 68, Line 51, replace "(amplficiation" with -- (amplification --.

Column 68, Line 60, replace "(A. lwoff" with -- (A. lwoffii --.

CERTIFICATE OF CORRECTION (continued)
U.S. Pat. No. 12,291,753 B2

Column 68, Line 67, replace "Iwoffi" with -- lwoffii --.

Column 70, Lines 21-26, replace "

| Mean normalized Ttimes are shown in Table 13 below. |
| --- |
| Table 13 |

| Sample Type | FAM | HEX | ROX | Cy5.5 |
| --- | --- | --- | --- | --- |

" with

| Mean normalized Ttimes are shown in Table 13 below. |
| --- |
| TABLE 13 |

| Sample Type | FAM | HEX | ROX | Cy5.5 |
| --- | --- | --- | --- | --- |

--.

Column 72, Line 48, replace "Dhihdrate" with -- Dihydrate --.

Column 72, Line 52, replace "volume:" with -- volume; --.

Column 72, Line 59, replace "volume:" with -- volume; --.

Column 77, Line 63, replace "iwoffii" with -- lwoffii --.

Column 78, Line 60, replace "bucalis" with -- buccalis --.

Column 80, Line 30, replace "(L.bucalis. M.curtisii. M.genitalium." with -- (L.buccalis, M.curtisii, M.genitalium, --.

Column 80, Line 40, replace "tropicalis. krusei." with -- tropicalis, krusei, --.

Column 80, Line 56, replace "(L.bucalis. M.curtisii. M.genitalium." with -- (L.buccalis, M.curtisii, M.genitalium, --.

Column 80, Line 62, replace "Example 1." with -- Example 1, --.

Columns 81 & 82, in table, Lines 1-3, replace

| " Sample | FAM (*Lacto* species) | HEX (*G. vag*) | ROX (*A. vag*) | Cy5.5 (GIC) " |
| --- | --- | --- | --- | --- | with

| TABLE 29 |
| --- |
| Ttime Results for Spiked Cross-Reactivity Testing |

| Sample | FAM (*Lacto* species) | HEX (*G. vag*) | ROX (*A. vag*) | Cy5.5 (GIC) |
| --- | --- | --- | --- | --- |

--.

Column 81, Line 39, replace "replicates:" with -- replicates; --.

Column 81, Line 47, replace "G.vag." with -- G.vag, --.

Column 81, Line 55, replace "Negative:" with -- Negative; --.

Column 81, Line 58, replace "L.crisp. G.vag." with -- L.crisp, G.vag, --.

Column 84, in Table 32, under "Description of Variant", Line 14, replace "T7 (v9)" with -- T7 (-9) --.

Columns 87 & 88, in table 33-continued, under "Sequence", Line 67, replace "cong" with -- ccng --.

Columns 87 & 88, in table 33-continued, under "Sequence", Line 69, replace "contt" with -- ccntt --.

Columns 87 & 88, in table 33-continued, under "Sequence", Line 72, replace "conc" with -- ccnc --.

Columns 89 & 90, in table 34, under "Sequence", Line 17, replace "AAAAA" with -- AAAAAA --.

Columns 89 & 90, in table 34, under "Sequence", Line 26, replace "GGT" with -- GGI --.

Columns 91 & 92, in table 34-continued, under "Sequence", Line 23, replace
"GGCUGCUGGCACGUAUTTTAAAAAAAAAAAAAAAAAAAAAAAAAAAAAA" with
-- GGCUGCUGGCACGUAUTTTAAAAAAAAAAAAAAAAAAAAAAAAAAAAAA --.

Columns 91 & 92, in table 34-continued, under "Sequence", Line 39, replace
"CAACUCGGCUAUGCAUCAUTTTAAAAAAAAAA" with
-- CAACUCGGCUAUGCAUCAUTTTAAAAAAAAAAAAAAAAAAAAAAAAAAAAAA --.

Columns 93 & 94, in table 34-continued, under "Sequence", Line 1, replace
"CUCUCAACUCGGCUAUGCTTTAAAAAAAAAAAAAAAAAAA" with
-- CUCUCAACUCGGCUAUGCTTTAAAAAAAAAAAAAAAAAAAAAAAAAAAAAA --.

Columns 93 & 94, in table 34-continued, under "Sequence", Line 2, replace
"ACCGUCAAAUAAAGGCCAGTTTAAAAAAAAAAAAAAAA" with
-- ACCGUCAAAUAAAGGCCAGTTTAAAAAAAAAAAAAAAAAAAAAAAAAAAAAA --.

Columns 95 & 96, in table 34-continued, under "Sequence", Line 24, replace "ATA" with -- AIA --.

Columns 95 & 96, in table 34-continued, under "Sequence", Line 27, replace "ATAT" with
-- AIAT --.

Columns 95 & 96, in table 34-continued, under "Sequence", Lines 31-32, replace
"CGGCCUCGUCCCUGCUGAAAGTTTAAAAAAAAAAAAAAAAAAAAA" with
-- CGGCCUCGUCCCUGCUGAAAGTTTAAAAAAAAAAAAAAAAAAAAAAAAAAAAAA --.

CERTIFICATE OF CORRECTION (continued)
U.S. Pat. No. 12,291,753 B2

Columns 97 & 98, in table 34-continued, under "Sequence", Line 13, replace "CTCG" with -- CICG --.

In the Claims

Column 201, Lines 6-7, in Claim 11, replace
"BV score=$C_0+W_L$Max($L_S,F_{LS}$)+$W_{GA}$Max($A_S,G_S,F_{GAS}$)+$W_{IC}$ Log 2(ICRatio)," with
-- BV score=$C_0+W_L$Max($L_S,F_{LS}$)+$W_{GA}$Max($A_S,G_S,F_{GAS}$)+$W_{IC}$Log2(ICRatio), --.

Column 201, Lines 10-11, in Claim 11, replace "Max ($L_S$, $F_{LS}$)" with -- Max($L_S$, $F_{LS}$) --.

Column 201, Line 17, in Claim 11, replace "Max ($A_S$, $G_S$," with -- Max($A_S$, $G_S$, --.

Column 201, Line 17, in Claim 11, replace "$A_S$, $G_S$," with -- $A_S$, $G_S$, --.

Column 201, Line 18, in Claim 11, replace "As" with -- $A_S$ --.

Column 201, Line 19, in Claim 11, replace "Gs" with -- $G_S$ --.